US008088951B2

(12) United States Patent
Tsai et al.

(10) Patent No.: US 8,088,951 B2
(45) Date of Patent: Jan. 3, 2012

(54) EPIGENETIC MECHANISMS RE-ESTABLISH ACCESS TO LONG-TERM MEMORY AFTER NEURONAL LOSS

(75) Inventors: Li-Huei Tsai, Cambridge, MA (US); Andre Fischer, Goettingen (DE); Stephen Haggarty, Dorchester, MA (US); Weiping Tang, Middleton, WI (US); Stuart L. Schreiber, Boston, MA (US)

(73) Assignees: Massachusetts Institute of Technology, Cambridge, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 328 days.

(21) Appl. No.: 11/998,834

(22) Filed: Nov. 30, 2007

(65) Prior Publication Data

US 2008/0300205 A1 Dec. 4, 2008

Related U.S. Application Data

(60) Provisional application No. 60/861,883, filed on Nov. 30, 2006.

(51) Int. Cl.
*C07C 233/00* (2006.01)
(52) U.S. Cl. ........................................ 564/123; 530/300
(58) Field of Classification Search .................. 564/123; 530/300
See application file for complete search history.

(56) References Cited

U.S. PATENT DOCUMENTS

| | | | |
|---|---|---|---|
| 4,946,999 A | 8/1990 | Koseki et al. | |
| 4,970,297 A * | 11/1990 | Castelhano et al. | ........... 530/331 |
| 5,525,727 A | 6/1996 | Bodor | |
| 7,183,298 B2 * | 2/2007 | Watkins et al. | ................ 514/352 |
| 2003/0235588 A1 | 12/2003 | Richon et al. | |
| 2004/0077591 A1 | 4/2004 | Dangond | |
| 2004/0087657 A1 | 5/2004 | Richon et al. | |
| 2004/0122101 A1 | 6/2004 | Miller et al. | |
| 2005/0037992 A1* | 2/2005 | Lyons et al. | .................... 514/49 |
| 2005/0288227 A1 | 12/2005 | Marks et al. | |
| 2006/0008517 A1 | 1/2006 | Lynch et al. | |
| 2006/0018921 A1 | 1/2006 | Levenson et al. | |
| 2007/0015183 A1 | 1/2007 | Krainc | |
| 2007/0078083 A1 | 4/2007 | Barlow et al. | |
| 2007/0197438 A1 | 8/2007 | Reiser et al. | |
| 2008/0188457 A1 | 8/2008 | Barlow et al. | |
| 2010/0015130 A1 | 1/2010 | Tsai et al. | |
| 2010/0075926 A1 | 3/2010 | Tsai et al. | |

FOREIGN PATENT DOCUMENTS

| | | | |
|---|---|---|---|
| WO | WO 2005/039549 A1 | 5/2005 | |
| WO | WO 2006/052916 A2 | 5/2006 | |
| WO | WO 2007/049262 A1 | 5/2007 | |

OTHER PUBLICATIONS

Ahlijanian M. K. (Proc Natl Acad Sci 97(6) 2910-2915, 2000).*
Alkire Michael T (Anesthesiology 109(5), 768-770, 2008).*
Bian, Feng (The Journal of Comparative Neurology 446(3), 257-266, 2002).*
Cardin J. A. (Journal of Neuroscience Research 58(1), 10-23, 1999.*
Colangelo James J (Journal of Child Sexual Abuse 18(1), 103-121, 2009).*
Geraerts Elke (Acta Psychologica 127(3), 614-622, 2008).*
Levy Benjamin J. (Acta Psychologica 127(3), 623-635, 2008).*
Akirav et al., The role of the medial prefrontal cortex-amygdala circuit in stress effects on the extinction of fear. Neural Plast. 2007:30873. Epub Jan. 16, 2007. Review.
Jinnouchi et al., Administration of pigment epithelium-derived factor (PEDF) inhibits cold injury-induced brain edema in mice. Brain Res. Sep. 5, 2007;1167:92-100. Epub Jul. 10, 2007.
Myers et al., Behavioral and neural analysis of extinction. Neuron. Nov. 14, 2002;36(4):567-84.
Pandey et al., Cloning and characterization of PAK5, a novel member of mammalian p21-activated kinase-II subfamily that is predominantly expressed in brain. Oncogene. May 30, 2002;21(24):3939-48.
Sakurada et al., Synapsin I is phosphorylated at Ser603 by p21-activated kinases (PAKs) in vitro and in PC12 cells stimulated with bradykinin. J Biol Chem. Nov. 22, 2002;277(47):45473-9. Epub Sep. 16, 2002.
Sananbenesi et al., A hippocampal Cdk5 pathway regulates extinction of contextual fear. Nat Neurosci. Aug. 2007;10(8):1012-9. Epub Jul. 15, 2007.
Bates, Huntington's disease. Exploiting expression. Nature. Oct. 18, 2001;413(6857):691, 693-4.
Boutillier et al., Constitutive repression of E2F1 transcriptional activity through HDAC proteins is essential for neuronal survival. Ann N Y Acad Sci. Nov. 2002;973:438-42.
Boutillier et al., Selective E2F-dependent gene transcription is controlled by histone deacetylase activity during neuronal apoptosis. J Neurochem. Feb. 2003;84(4):814-28.
Bredy et al., The histone deacetylase inhibitor valproic acid enhances acquisition, extinction, and reconsolidation of conditioned fear. Learn Mem. Jan. 3, 2008;15(1):39-45. Print Jan. 2008.
Brettman et al., Pharmacokinetics and safety of single oral doses of VX-366 (isobutyramide) in healthy volunteers. J Clin Pharmacol. Jul. 1996;36(7):617-22.
Cerna et al., Histone deacetylation as a target for radiosensitization. Curr Top Dev Biol. 2006;73:173-204. Review.
Chen et al., The mood-stabilizing agent valproate inhibits the activity of glycogen synthase kinase-3. J Neurochem. Mar. 1999;72(3):1327-30.
Citrome, Schizophrenia and valproate. Psychopharmacol Bull. 2003;37 Suppl 2:74-88. Review.
De Ruijter et al., Histone deacetylases (HDACs): characterization of the classical HDAC family. Biochem J. Mar. 15, 2003;370(Pt 3):737-49. Review.
Fischer et al., Recovery of learning and memory is associated with chromatin remodelling. Nature. May 10, 2007;447(7141):178-82. Epub Apr. 29, 2007.

(Continued)

*Primary Examiner* — David Lukton
(74) *Attorney, Agent, or Firm* — Wolf, Greenfield & Sacks, P.C.

(57) ABSTRACT

The invention relates to methods and products for enhancing and improving recovery of lost memories. In particular the methods are accomplished through the increase of histone acetylation.

15 Claims, 42 Drawing Sheets

OTHER PUBLICATIONS

Gojo et al., Phase 1 and pharmacologic study of MS-275, a histone deacetylase inhibitor, in adults with refractory and relapsed acute leukemias. Blood. Apr. 1, 2007;109(7):2781-90.

Gould et al., Emerging experimental therapeutics for bipolar disorder: insights from the molecular and cellular actions of current mood stabilizers. Mol Psychiatry. Aug. 2004;9(8):734-55.

Gould et al., Signaling networks in the pathophysiology and treatment of mood disorders. J Psychosom Res. Aug. 2002;53(2):687-97. Review.

Guan et al., HDAC2 negatively regulates memory formation and synaptic plasticity. Nature. May 7, 2009;459(7243):55-60.

Gui et al., Histone deacetylase (HDAC) inhibitor activation of p21WAF1 involves changes in promoter-associated proteins, including HDAC1. Proc Natl Acad Sci U S A. Feb. 3, 2004;101(5):1241-6. Epub Jan. 20, 2004.

Hockly et al., Suberoylanilide hydroxamic acid, a histone deacetylase inhibitor, ameliorates motor deficits in a mouse model of Huntington's disease. Proc Natl Acad Sci U S A. Feb. 18, 2003;100(4):2041-6. Epub Feb. 7, 2003.

Hu et al., Identification of novel isoform-selective inhibitors within class I histone deacetylases. J Pharmacol Exp Ther. Nov. 2003;307(2):720-8. Epub Sep. 15, 2003.

Johannessen et al., Valproate: past, present, and future. CNS Drug Rev. 2003 Summer;9(2):199-216.

Kim et al., Inhibition of histone deacetylation enhances the neurotoxicity induced by the C-terminal fragments of amyloid precursor protein. J Neurosci Res. Jan. 1, 2004;75(1):117-24.

Lagger et al., Essential function of histone deacetylase 1 in proliferation control and CDK inhibitor repression. EMBO J. Jun. 3, 2002;21(11):2672-81.

Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50. Review.

Lattal et al., Systemic or intrahippocampal delivery of histone deacetylase inhibitors facilitates fear extinction. Behav Neurosci. Oct. 2007;121(5):1125-31.

Leng et al., Synergistic neuroprotective effects of lithium and valproic acid or other histone deacetylase inhibitors in neurons: roles of glycogen synthase kinase-3 inhibition. J Neurosci. Mar. 5, 2008;28(10):2576-88.

Liu et al., Regulation of neuron survival and death by p130 and associated chromatin modifiers. Genes Dev. Mar. 15, 2005;19(6):719-32.

Manji et al., The underlying neurobiology of bipolar disorder. World Psychiatry. Oct. 2003;2(3):136-46.

Mao et al., Disrupted in schizophrenia 1 regulates neuronal progenitor proliferation via modulation of GSK3beta/beta-catenin signaling. Cell. Mar. 20, 2009;136(6):1017-31.

Mccampbell et al., Histone deacetylase inhibitors reduce polyglutamine toxicity. Proc Natl Acad Sci U S A. Dec. 18, 2001;98(26):15179-84. Epub Dec. 11, 2001.

Monfils et al., Extinction-reconsolidation boundaries: key to persistent attenuation of fear memories. Science. May 15, 2009;324(5929):951-5. Epub Apr. 2, 2009.

Morrison et al., Neuroprotection by histone deacetylase-related protein. Mol Cell Biol. May 2006;26(9):3550-64.

Salminen et al., Neuronal apoptosis induced by histone deacetylase inhibitors. Brain Res Mol Brain Res. Oct. 30, 1998;61(1-2):203-6.

Sancar et al., Molecular mechanisms of mammalian DNA repair and the DNA damage checkpoints. Annu Rev Biochem. 2004;73:39-85. Review.

Schiller et al., Preventing the return of fear in humans using reconsolidation update mechanisms. Nature. Jan. 7, 2010;463(7277):49-53. Epub Dec. 9, 2009.

Schnurr et al., Cognitive behavioral therapy for posttraumatic stress disorder in women: a randomized controlled trial. JAMA. Feb. 28, 2007;297(8):820-30.

Steffan et al., Histone deacetylase inhibitors arrest polyglutamine-dependent neurodegeneration in Drosophila. Nature. Oct. 18, 2001;413(6857):739-43.

Sweatt, Behavioural neuroscience: Down memory lane. Nature. May 10, 2007;447(7141):151-2.

Taunton et al., A mammalian histone deacetylase related to the yeast transcriptional regulator Rpd3p. Science. Apr. 19, 1996;272(5260):408-11.

Vincent et al., Mitotic mechanisms in Alzheimer's disease? J Cell Biol. Feb. 1996;132(3):413-25.

Yamaguchi et al., Histone deacetylase 1 regulates retinal neurogenesis in zebrafish by suppressing Wnt and Notch signaling pathways. Development. Jul. 2005;132(13):3027-43.

Zarate et al., Molecular mechanisms of bipolar disorder. Drug Disc Today: Disease Mech. 2005;2(4):435-45.

Alarcón et al., Chromatin acetylation, memory, and LTP are impaired in CBP+/− mice: a model for the cognitive deficit in Rubinstein-Taybi syndrome and its amelioration. Neuron. Jun. 24, 2004;42(6):947-59.

Andorfer et al., Cell-cycle reentry and cell death in transgenic mice expressing nonmutant human tau isoforms. J Neurosci. Jun. 1, 2005;25(22):5446-54.

Bradshaw et al., Fluctuating cognition in dementia with Lewy bodies and Alzheimer's disease is qualitatively distinct. J Neurol Neurosurg Psychiatry. Mar. 2004;75(3):382-7.

Chen et al., Regulation of transcription by a protein methyltransferase. Science. Jun. 25, 1999;284(5423):2174-7.

Cruz et al., A Jekyll and Hyde kinase: roles for Cdk5 in brain development and disease. Curr Opin Neurobiol. Jun. 2004;14(3):390-4. Review.

Cruz et al., Aberrant Cdk5 activation by p25 triggers pathological events leading to neurodegeneration and neurofibrillary tangles. Neuron. Oct. 30, 2003;40(3):471-83.

Fischer et al., Cyclin-dependent kinase 5 is required for associative learning. J Neurosci. May 1, 2002;22(9):3700-7.

Fischer et al., Opposing roles of transient and prolonged expression of p25 in synaptic plasticity and hippocampus-dependent memory. Neuron. Dec. 8, 2005;48(5):825-38.

Fischer et al., Recover of learning and memory is associated with chromatin remodelling.Nature. May 10, 2007; 447(7141):151-2.

Frankland et al., The involvement of the anterior cingulate cortex in remote contextual fear memory. Science. May 7, 2004;304(5672):881-3.

Frey et al., Trifluoromethyl ketones as inhibitors of histone deacetylase. Bioorg Med Chem Lett. Dec. 2, 2002;12(23):3443-7.

Gilmore et al., Neocortical cell migration: GABAergic neurons and cells in layers I and VI move in a cyclin-dependent kinase 5-independent manner. J Neurosci. Dec. 15, 2001;21(24):9690-700.

Haggarty et al., Multidimensional chemical genetic analysis of diversity-oriented synthesis-derived deacetylase inhibitors using cell-based assays. Chem Biol. May 2003;10(5):383-96.

Horn et al., Neural network modeling of memory deterioration in Alzheimer's disease. Neural Computation. 1993;5:736-49.

Horn et al., Neuronal-based synaptic compensation: a computational study in Alzheimer's disease. Neural Comput. Aug. 15, 1996;8(6):1227-43.

Hwang et al., Systematic characterization of nuclear proteome during apoptosis: a quantitative proteomic study by differential extraction and stable isotope labeling. Mol Cell Proteomics. Jun. 2006;5(6):1131-45. Epub Mar. 14, 2006.

Kim et al., Modality-specific retrograde amnesia of fear. Science. May 1, 1992;256(5057):675-7.

Korzus et al., CBP histone acetyltransferase activity is a critical component of memory consolidation. Neuron. Jun. 24, 2004;42(6):961-72.

Kouzarides et al., Histone acetylases and deacetylases in cell proliferation. Opin Genet Dev. Feb. 1999;9(1):40-8. Review.

Kumar et al., Chromatin remodeling is a key mechanism underlying cocaine-induced plasticity in striatum. Neuron. Oct. 20, 2005;48(2):303-14.

Levenson et al., Regulation of histone acetylation during memory formation in the hippocampus. J Biol Chem. Sep. 24, 2004;279(39):40545-59. Epub Jul. 23, 2004.

Need et al., Handling and environmental enrichment do not rescue learning and memory impairments in alphaCamKII(T286A) mutant mice. Genes Brain Behav. Jun. 2003;2(3):132-9.

Ng et al., Histone deacetylases: silencers for hire. Trends Biochem Sci. Mar. 2000;25(3):121-6. Review.

Nithiananthrajah et al., Enriched environments, experience-dependent plasticity and disorders of the nervous system. Nat Rev Neurosci. Sep. 2006;7(9):697-709. Review.

Palop et al., A network dysfunction perspective on neurodegenerative diseases. Nature. Oct. 19, 2006;443(7113):768-73. Review.

Rampon et al., Effects of environmental enrichment on gene expression in the brain. Proc Natl Acad Sci U S A. Nov. 7, 2000;97(23):12880-4.

Ruppin et al., Pathogenesis of schizophrenic delusions and hallucinations: a neural model. Schizophr Bull. 1996;22(1):105-23.

Santacruz et al., Tau suppression in a neurodegenerative mouse model improves memory function. Science. Jul. 15, 2005;309(5733):476-81.

Sassone-Corsi et al., Requirement of Rsk-2 for epidermal growth factor-activated phosphorylation of histone H3. Science. Aug. 6, 1999;285(5429):886-91.

Sterner et al., Acetylation of histones and transcription-related factors. Microbiol Mol Biol Rev. Jun. 2000;64(2):435-59. Review.

Tang et al., Differential effects of enrichment on learning and memory function in NR2B transgenic mice. Neuropharmacology. Nov. 2001;41(6):779-90.

Tsankova et al., Sustained hippocampal chromatin regulation in a mouse model of depression and antidepressant action. Nature Neuroscience 9: Apr. 2006 (519-525).

Van Praag et al., Neural consequences of environmental enrichment. Nat Rev Neurosci. Dec. 2000;1(3):191-8. Review.

Voss et al., Possible axonal regrowth in late recovery from the minimally conscious state. J Clin Invest. Jul. 2006;116(7):2005-11.

Wada et al., Alpha-keto amides as inhibitors of histone deacetylase. Bioorg Med Chem Lett. Oct. 6, 2003;13(19):3331-5.

Wade et al., Histone acetylation: chromatin in action. Trends Biochem Sci. Apr. 1997;22(4):128-32. Review.

\* cited by examiner

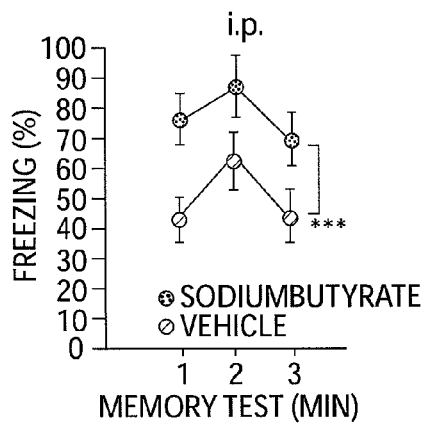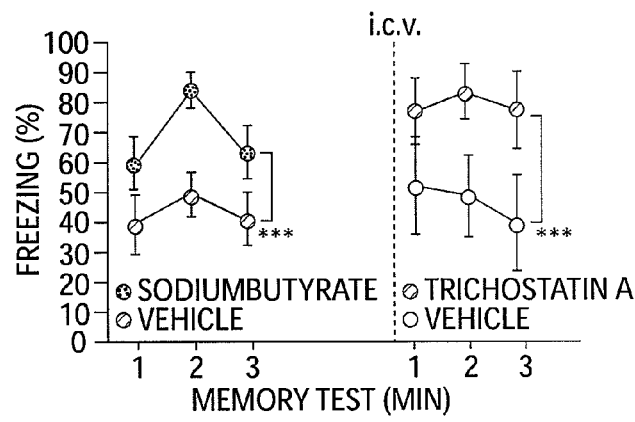
Fig. 8A  Fig. 8B
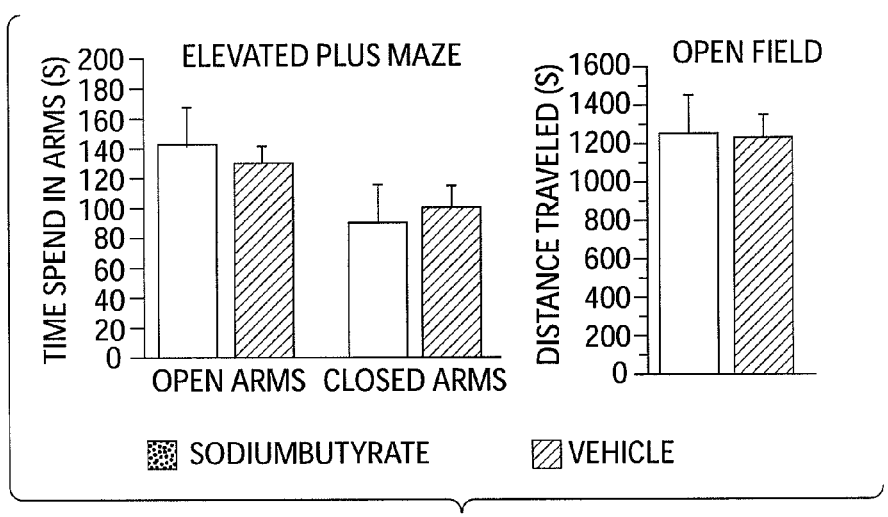
Fig. 8C

IN VITRO HISTONE DEACETYLASE ASSAY
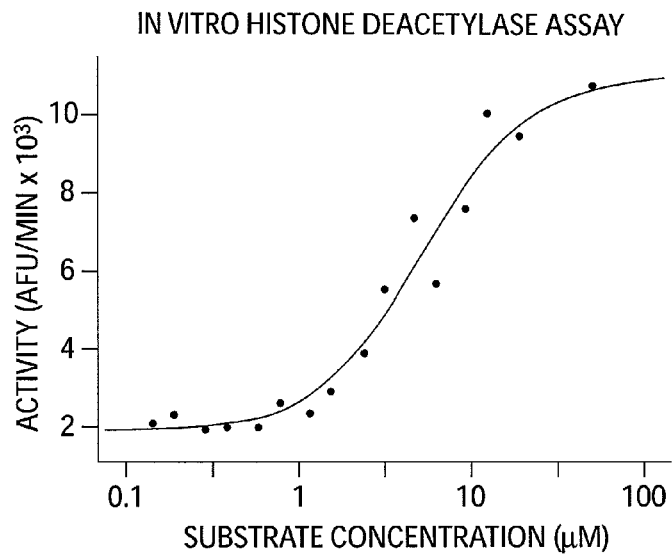
Fig. 18D
| COMPOUND | HDAC5 | HDAC3 |
|---|---|---|
| SAHA | 150 | 64 |
| TRICHOSTATIN A | 10 | 1 |
| APICIDIN | 17 | 4 |
$IC_{50}$ (nM) VALES FOR HDAC INHIBITION
Fig. 18E
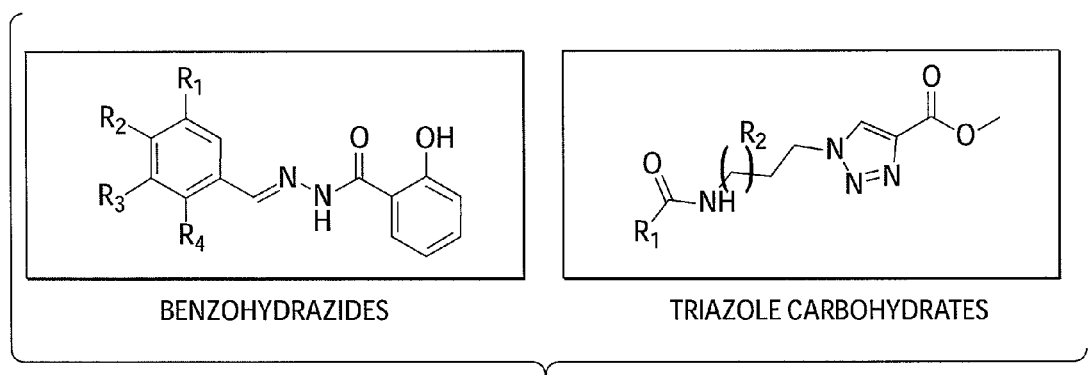
BENZOHYDRAZIDES     TRIAZOLE CARBOHYDRATES
Fig. 18F

PROTOTYPICAL HYDRAZONES

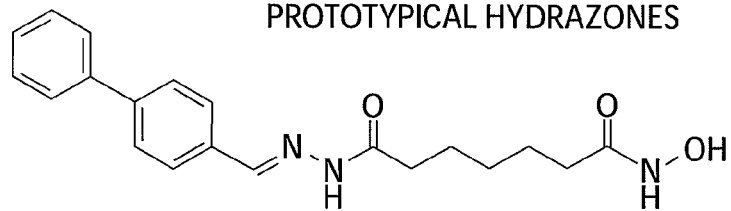

UW_WT_I_06
(2133-A15; CHDI1_000360)

CHEMICAL FORMULA: $C_{20}H_{23}N_3O_3$
MOLECULAR WEIGHT: 353.41

STRONG INHIBITOR OF RECOMBINANT
HDAC1,2,6,8,10 DEACETYLASE ACTIVITY
STRONGLY INDUCES AcH3 AND AcH4 IN
CELLS AT 20 μM
ACTIVATES CREB REPORTER GENE
INDUCES BDNF EXON IV mRNA
INDUCES DNA DEMETHYLATION

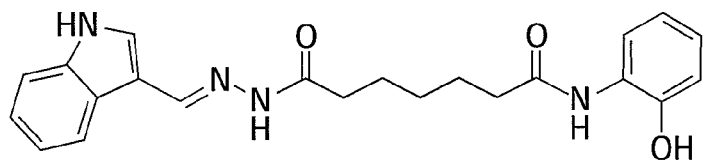

UW_WT_I_05
(2133-B11; CHDI1_000534)

CHEMICAL FORMULA: $C_{22}H_{24}N_4O_3$
MOLECULAR WEIGHT: 392.45

STRONG INHIBITOR OF RECOMBINANT
HDAC1,2,10 DEACETYLASE ACTIVITY (NOT 6,8)
WEAKLY INDUCES AcH3 AND AcH4 IN CELLS
AT 20 μM
ACTIVATES CREB REPORTER GENE
NOT TESTED
NO INDUCTION OF DNA DEMETHYLATION

Fig. 20

EPIGENETIC MECHANISMS RE-ESTABLISH ACCESS TO LONG-TERM MEMORY AFTER NEURONAL LOSS

RELATED APPLICATION

This application claims priority under 35 USC §119 to U.S. Provisional Application No. 60/861,883, filed Nov. 30, 2006, the entire contents of which is hereby incorporated by reference.

FEDERALLY SPONSORED RESEARCH

This invention was made with Government support under NIH NS051874. Accordingly, the Government has certain rights in this invention.

BACKGROUND OF INVENTION

Brain atrophy occurs during normal aging and is an early feature of neurodegenerative diseases associated with impaired learning and memory. Only recently have mouse models with extensive neurodegeneration in the forebrain been reported (1-3). One of these models is the bi-transgenic CK-p25 Tg mice where expression of p25, a protein implicated in various neurodegenerative diseases (4), is under the control of the CamKII promoter and can be switched on or off with a doxycycline diet (3,5). Post-natal induction of p25 expression for 6 weeks caused learning impairment that was accompanied by severe synaptic and neuronal loss in the forebrain. However, pre-clinical research has not yet explored strategies to recover lost memories after substantial neuronal loss had taken place.

SUMMARY OF INVENTION

Neurodegenerative diseases of the central nervous system are often associated with impaired learning and memory, eventually leading to dementia. An important aspect that has not been addressed extensively in pre-clinical research, is the loss of long-term memories and the exploration of strategies to re-establish access to those memories. In some embodiments the current invention provides methods for restoring access to long-term memory after synaptic and neuronal loss has already occurred. Environmental enrichment (EE) has been shown to reinstate learning behavior and re-establish access to long-term memories after significant brain atrophy and neuronal loss has already occurred. Also shown herein is a correlation between EE and epigenetic changes. EE increases histone-tail acetylation and changes the level of methylation. The increase in acetylation and change in level of methylation is observed in hippocampal and cortical histone 3 (H3) and histone 4 (H4). In turn, elevated histone H3 and H4 acetylation initiate rewiring of the neural network.

In some embodiments the invention provides methods for inducing an increase in histone acetylation. In some aspects the invention provides methods for the change in level of methylation in histones. One aspect of the invention is the increase in histone acetylation through the administration of inhibitors of histone-deacetylases. The administration of inhibitors of histone-deacetylases induced sprouting of dendrites, an increased number of synapses, and reinstated learning behavior and access to long-term memories. In some embodiments the invention provides epigenetic approaches as a therapeutic avenue for neurodegenerative diseases associated with learning and memory impairment including the recovery of long-term memories in patients with dementia.

In some aspects the invention provides a method for recapturing a memory comprising increasing histone acetylation in an amount effective to re-establish access to a memory in a subject having memory loss. In some embodiments the invention provides a method for accessing long-term memory in a subject having diminished access to a long-term memory comprising increasing histone acetylation in an amount effective to reestablish access to long-term memory in the subject.

In some aspects of the invention the long-term memory is impaired. In some embodiments the impairment may be age-related or injury-related. In some embodiments of the invention a synaptic network in the subject is re-established. In some embodiments re-establishing the synaptic network comprises an increase in the number of active brain synapses. In some embodiments re-establishing the synaptic network comprises a reversal of neuronal loss.

In some embodiments of the invention histone acetylation comprises acetylation of H3 or H4. A further embodiment comprises increasing histone acetylation by administering a therapeutically effective amount of HDAC inhibitor to the subject. In some embodiments the HDAC inhibitor is trichostatin A, trichostatin B, trichostatin C, trapoxin A, trapoxin B, chlamydocin, sodium salts butyrate, butyric acid, sodium salts of phenylbutyrate, phenylbutyric acid, scriptaid, FR901228, depudecin, oxamflatin, pyroxamide, apicidin B, apicidin C, *Helminthsporium carbonum* toxin, 2-amino-8-oxo-9,10-epoxy-decanoyl, 3-(4-aroyl-1H-pyrrol-2-yl)-N-hydroxy-2-propenamide, suberoylanilide hydroxamic acid, [valproic acid], FK228 or m-carboxycinnamic acid bis-hydroxamide. In some embodiments a second HDAC inhibitor is administered. In some embodiments the HDAC inhibitor is administered orally, intravenously, cutaneously, subcutaneously, nasally, intramuscularly, intraperitoneally or intracerebroventricularly.

In some embodiments the method comprises altering the methylation level of one or more genes. In some embodiments altering the methylation level of one or more genes comprises administering a DNA methylase inhibitor. In some embodiments the DNA methylation inhibitor is 5-azacytidine, 5-aza-2'deoxycytidine, 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine, and procainamide, Zebularine, or (−)-egallocatechin-3-gallate.

In some aspects the invention provides a pharmaceutical composition comprising an HDAC inhibitor and a pharmaceutically acceptable carrier in a formulation for delivery to brain tissue.

In some aspects the invention provides a method for recapturing a memory comprising increasing histone acetylation, by a method other than an HDAC inhibitor, in an amount effective to re-establish access to a lost memory in a subject having Alzheimer's disease.

In yet other aspects the invention provides a method for recapturing a memory comprising administering an HDAC inhibitor, in an amount effective to re-establish access to a lost memory, in a subject having Alzheimer's disease and monitoring the subject to identify recapture of a memory that was previously lost.

In some embodiments of the methods and compositions described herein the histone acetylase inhibitor is a binding peptide such as an antibody or antibody fragment. In other embodiments the histone acetylase inhibitor is an antisense molecule. In yet other embodiments the histone acetylase inhibitor is an siRNA. The histone acetylase inhibitor in other embodiments is an HDAC inhibitor such as for instance a compound of the formula:

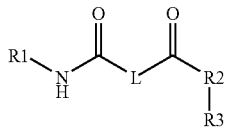

(I)

wherein R1 is selected from either an aryl ring system optionally substituted, or —N═R4; R2 is selected from either carbon or a heteroatom that is optionally substituted with at least one hydrogen, alkyl, alkenyl, aryl, halogen, and heteroatomic groups; R3 is absent or it is a carbon or heteroatom that is optionally substituted with at least one hydrogen, alkyl, alkenyl, aryl, halogen, and heteroatomic groups; R4 comprises a carbon atom bound to an optionally substituted aryl, heteroaromatic, or biaryl ring system; and L is 1 to 12 carbons optionally bonded to heteroatoms, alkyl, alkenyl, or aryl groups or a pharmaceutically acceptable salt thereof.

In some embodiments R2 and R3 are adjacent atoms within an aromatic or heteroaromatic ring system that is optionally substituted with at least one hydrogen, alkyl, alkenyl, aryl, halogen, and heteroatomic groups.

The histone acetylase inhibitor may be one or more of the following structures:

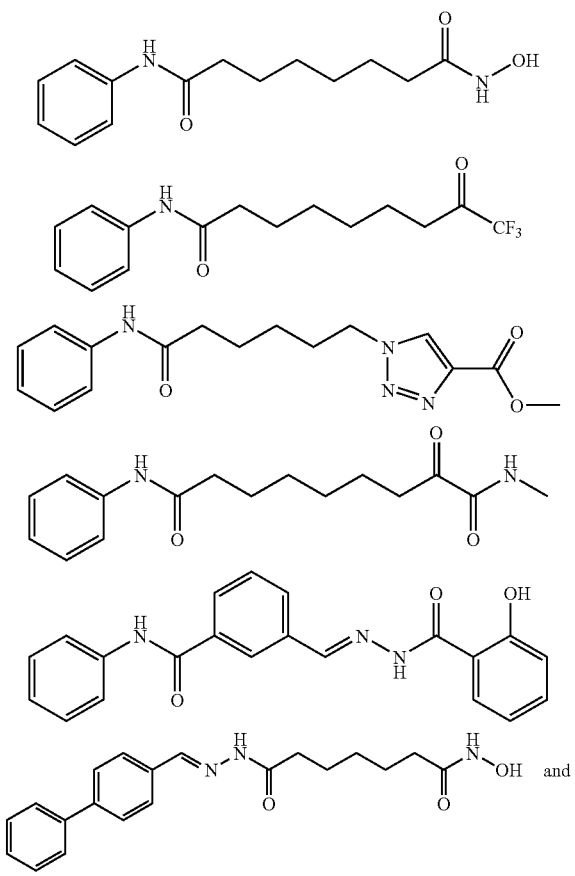

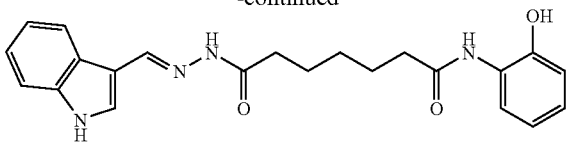

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 20 is a diagram of the structure of two new molecules UW_WT_-I_06 and UW_WT_-I_05.

DETAILED DESCRIPTION

Figure 1A:
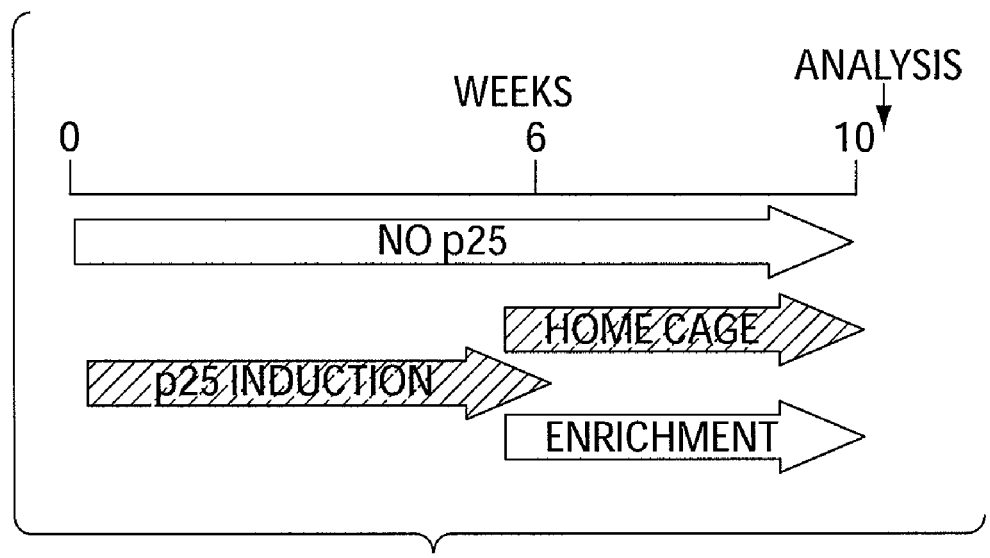
FIG. 1 shows that enrichment reinstates learning in CK-p25 Tg mice after neurodegeneration. a. Experimental design. b. Enriched and non-enriched CK-p25 Tg mice displayed similar brain atrophy. c. Fear memories (tested 24 h after the training). d. Brain weight plotted against freezing behavior. e. Escape latency in water maze test. f. Representative immunoblots from control mice, enriched and non-enriched CK-p25 Tg mice. g. Representative pictures of the hippocampal region showing staining for the synaptic marker protein synaptophysin (SVP).

The invention relates in some aspects to therapeutics for enhancing and/or retrieving memories. A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Enhancing or retrieving memories is distinct from learning. However, in some instances in the art learning is referred to as memory. The present invention distinguishes between learning and memory and is focused on enhancing memories. Learning, unlike memory enhancement, refers to the ability to create new memories that had not previously existed. Thus in order to test the ability of a therapeutic agent to effect the ability of a subject to learn rather than recall old memories, the therapeutic would be administered prior to or at the same time as the memory is created. In order to test the ability of a therapeutic to effect recall of a previously created memory the therapeutic is administered after the memory is created and preferably after the memory is lost.

In some instances the invention relates to methods for recapturing a memory in a subject. In order to recapture the memory the memory has been lost. A lost memory is one which cannot be retrieved by the subject without assistance, such as the therapeutic of the invention. In other words the subject cannot recall the memory. As used herein the term "recapture" refers to the ability of a subject to recall a memory that the subject was previously unable to recall. Generally, such a subject has a condition referred to as memory loss. A subject having memory loss is a subject that cannot recall one or more memories. The memories may be short term memories or long term memories. Methods for assessing the ability to recall a memory are known to those of skill in the art and may include routine cognitive tests.

In other instances the invention relates to a method for accessing long-term memory in a subject having diminished access to a long-term memory. A subject having diminished access to a memory is a subject that has experienced one or more long term memory lapses. The long-term memory lapse may be intermittent or continuous. Thus, a subject having diminished access to a long term memory includes but is not limited to a subject having memory loss, with respect to long term memories.

In some instances the long-term memory of the "subject having diminished access" may be impaired. An impaired long-term memory is one in which a physiological condition of the subject is associated with the long-term memory loss. Conditions associated with long-term memory loss include but are not limited to age related memory loss and injury related memory loss.

As used herein "age related memory loss" refers to refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). This term specifically excludes age-related dementias such as Alzheimer's disease and Parkinson's disease, and conditions of mental retardation such as Down's syndrome. Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517, which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and reduction of cognition.

As used herein "injury related memory loss" refers to damage which occurs to the brain, and which may result in neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus.

A subject shall mean a human or vertebrate animal or mammal including but not limited to a dog, cat, horse, cow, pig, sheep, goat, turkey, chicken, and primate, e.g., monkey. Subjects are those which are not otherwise in need of an HDAC inhibitor. Subjects specifically exclude subjects having Alzheimer's disease, except in the instance where a subject having Alzheimer's disease is explicitly recited.

The histone acetylation is preferably administered in an amount effective to re-establish access to a memory. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss. Data demonstrating evidence of re-establishment of a synaptic network is presented in the Examples below.

As used herein, the term re-establish access to long-term memory when used with respect to a disorder comprising memory loss or memory lapse refers to a treatment which increases the ability of a subject to recall a memory. In some instances the therapeutic of the invention also decreases the incidence and/or frequency with which the memory is lost or cannot be retrieved.

The methods of the invention may also be directed to the recapture of a memory in a subject having Alzheimer's disease. Alzheimer's disease is a disorder in which the cognitive systems that control memory have been damaged. Often long-term memory is retained while short-term memory is lost; conversely, memories may become confused, resulting in mistakes in recognizing people or places that should be familiar.

Methods for recapturing a memory in a subject having Alzheimer's disease by administering an HDAC inhibitor are also provided according to the invention. Such methods involve administering the inhibitor and monitoring the subject to identify recapture of a memory that was previously lost. Subjects may be monitored by routine tests known in the art. For instance some are described in books such as DSM described above or in the medical literature.

In some embodiments the method is accomplished by increasing histone acetylation, by a method other than an HDAC inhibitor. Methods for increasing histone acetylation, by a method other than a classic HDAC inhibitor include but are not limited to nucleic acid molecule inhibitors such as antisense and RNAi molecules which reduce the expression of histone deacetylase and histone acetylase activators. The invention embraces methods that regulate the function of any protein involved with histone modification, function and regulation.

A number of enzymes capable of chemical modification of histones have been described. For example, histone acetyl transferases include Gcn5p, p300/CBP-associated factor (P/CAF), p300, CREB-binding protein (CBP), HAT1, TFIID-associated factor 250 ($TAF_{II}250$), and steroid receptor coactivator-1 (SRC-1) (Wade et al. (1997) Trends Biochem. Sci. 22:128-132; Kouzarides (1999) Curr. Opin. Genet. Devel. 9:40-48; Sterner et al. (2000) Microbiol. Mol. Biol. Rev. 64:435-459). The HDAC family of proteins have been identified as histone deacetylases and include homologues to the budding yeast histone deacetylase RPD3 (e.g., HDAC1, HDAC2, HDAC3 and HDAC8) and homologues to the budding yeast histone deacetylase HDA1 (e.g., HDAC4, HDAC5, HDAC6 and HDAC7)(Ng et al. (2000) Trends Biochem. Sci. 25:121-126). The Rsk-2 (RKS90) kinase has been identified as a histone kinase. Sassone-Corsi et al. (1999) Science 285:886-891. A histone methyltransferase (CARM-1) has also been identified. Chen et al. (1999) Science 284: 2174-2177. Nucleosomes, the primary scaffold of chromatin folding, are dynamic macromolecular structures, influencing chromatin solution conformations. The nucleosome core is made up of histone proteins, H2A, H2B, H3 and H4. Histone acetylation causes nucleosomes and nucleosomal arrangements to behave with altered biophysical properties. The balance between activities of histone acetyl transferases (HAT) and deacetylases (HDAC) determines the level of histone acetylation. Acetylated histones cause relaxation of chromatin and activation of gene transcription, whereas deacetylated chromatin generally is transcriptionally inactive.

Figure 21:
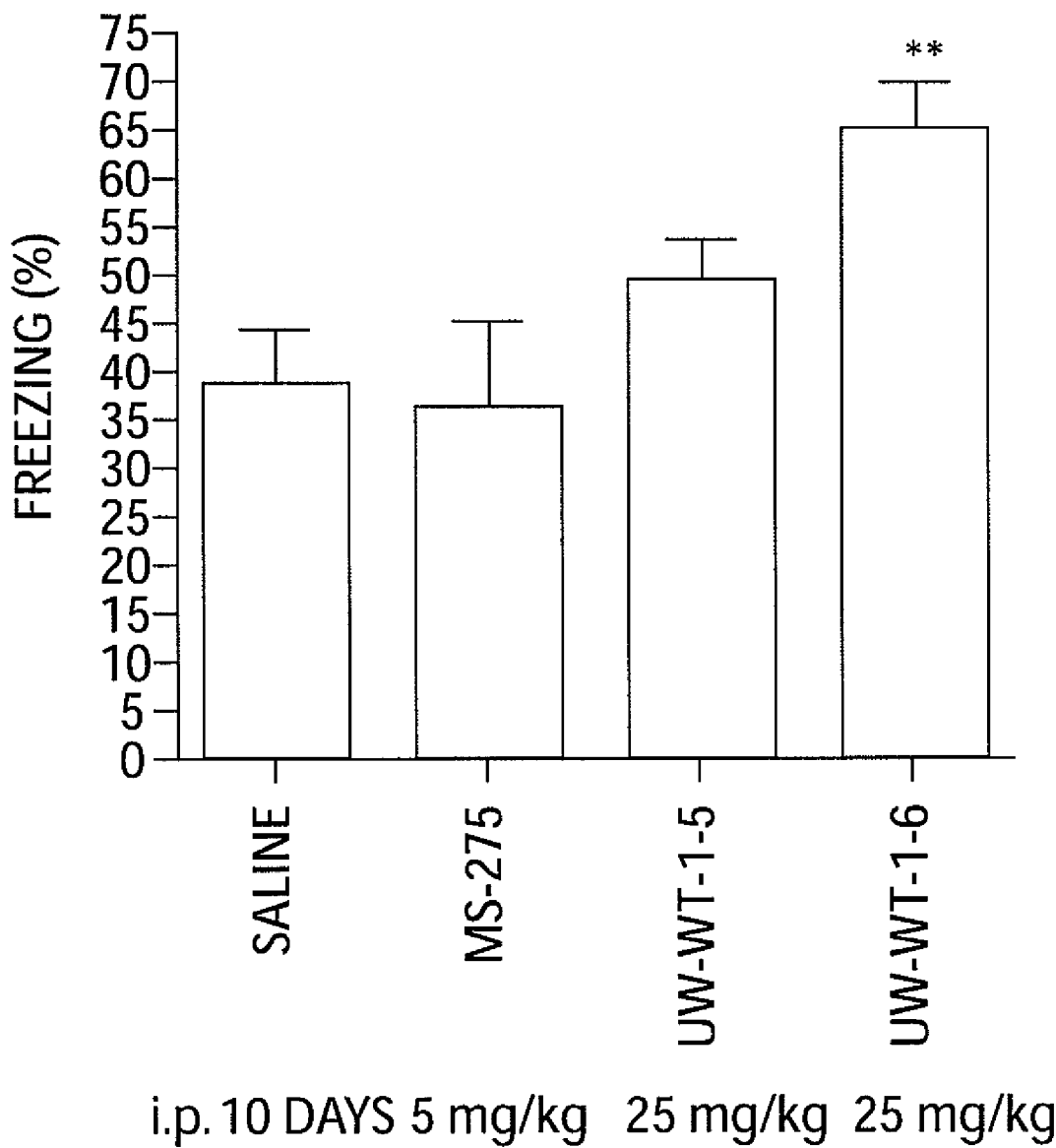
FIG. 21 is a bar graph demonstrating that UW_WT_-I_06 significantly and UW_WT_-I_05 to a lesser extent enhanced associative learning. These compounds show strong inhibitory activity toward HDAC 1,2, and 10 with UW_WT_-I_06 also inhibiting HDAC 6 and 8.

It has been demonstrated herein that general HDAC inhibitors (e.g.; sodium butyrate, SAHA, TSA) enhance learning and memory. Studies described in the Examples below were also undertaken to determine which of the 11 histone deacetylases is responsible for the observed function. It was discovered that while HDAC1 Tg mice do not show any difference in learning behavior compared to the control mice, HDAC2 Tg mice have impaired learning as evaluated by Pavlovian fear conditioning and Morris water maze tests (FIGS. 10 and 11). Remarkably, HDAC2 neuron specific knockout mice (loss of function) display enhanced learning (FIG. 12). Furthermore, it was discovered that impaired learning exhibited by HDAC2 Tg mice is accompanied by reduced neurogenesis in the adult dentate gyrus (FIG. 13), and reduced CREB expression (FIG. 14). These observations suggest that HDAC2 participates in learning and memory and that it is likely to be the target of inhibition by the general HDAC inhibitors. It was also discovered that novel inhibitors of HDAC1, 2, 6, 8, and 10 also enhance memory (FIG. 21).

A histone deacetylase inhibitor as used herein is a compound that inhibits the activity of histone deacetylase. One of ordinary skill in the art can select suitable compounds on the basis of the known structures of histone deacetylases. Examples of such compounds are binding peptides such as antibodies, preferably monoclonal antibodies, antibody fragments, scFv, etc that specifically react with the histone deacetylase, small molecule inhibitors referred to as HDAC inhibitors, and expression inhibitors such as antisense and siRNA.

HDAC inhibitors include but are not limited to the following compounds, functional analogs and salts thereof: trichostatin A (TSA), trichostatin B, trichostatin C, trapoxin A, trapoxin B, chlamydocin, sodium salts of butyrate, butyric acid, sodium salts of phenylbutyrate, phenylbutyric acid, scriptaid, FR901228, depudecin, oxamflatin, pyroxamide, apicidin B, apicidin C, *Helminthsporium carbonum* toxin, 2-amino-8-oxo-9,10-epoxy-decanoyl, 3-(4-aroyl-1H-pyrrol-2-yl)-N-hydroxy-2-propenamide, suberoylanilide hydroxamic acid (SAHA), valproic acid, FK228, or m-carboxycinnamic acid bis-hydroxamide. In preferred embodiments the HDAC inhibitor is an HDAC2 inhibitor such as sodium butyrate, SAHA or TSA. Derivatives of the inhibitors showing increased pharmacological half-life are also useful according to the invention (Brettman and Chaturvedi, J. Cli. Pharmacol. 36 (1996), 617-622).

The HDAC inhibitors include SAHA. "SAHA" as used herein refers to suberoylanilide hydroxamic acid, analogs, derivatives and polymorphs. Polymorphs of SAHA are described in US Published Patent Application No. 20040122101 which is incorporated by reference. HDAC inhibitors that are SAHA include those described by the following formula and having ability to inhibit HDAC2:

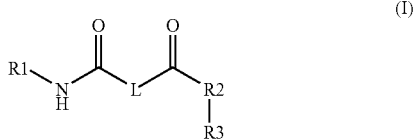

(I)

wherein R1 is selected from an aryl ring system optionally substituted; R2 is selected from either carbon or a heteroatom that is optionally substituted with at least one hydrogen, alkyl, alkenyl, aryl, halogen, and heteroatomic groups; R3 is absent or it is a carbon or heteroatom that is optionally substituted with at least one hydrogen, alkyl, alkenyl, aryl, halogen, and heteroatomic groups; and L is 1 to 12 carbons optionally bonded to heteroatoms, alkyl, alkenyl, or aryl groups.

"Alkyl" in general, refers to an aliphatic hydrocarbon group which may be straight, branched or cyclic having from 1 to about 10 carbon atoms in the chain, and all combinations and sub combinations of ranges therein. The term "alkyl" includes both "unsubstituted alkyls" and "substituted alkyls," the latter of which refers to alkyl moieties having substituents replacing a hydrogen on one or more carbons of the backbone. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure. Unless the number of carbons is otherwise specified, "lower alkyl" as used herein means an alkyl group, as defined above, but having from one to ten carbons, more preferably from one to six carbon atoms in its backbone structure, and even more preferably from one to four carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. Alkyl substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkenyl" refers to unsaturated aliphatic groups analogous in length and possible substitution to the alkyls described above, but that contain at least one double bond.

As used herein, the term "halogen" designates —F, —Cl, —Br or —I; the term "sulfhydryl" means —SH; and the term "hydroxyl" means —OH.

The term "aryl," alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl, and includes carbocyclic aryl, heterocyclic aryl and biaryl groups, all of which may be optionally substituted. The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl. The term "carbocyclic" refers to a cyclic compounds in which all of the ring members are carbon atoms. Such rings may be optionally substituted. The compound can be a single ring or a biaryl ring. The term "cycloalkyl" embraces radicals having three to ten carbon atoms, such as cyclopropyl, cyclobutyl, cyclopentyl, cyclohexyl, cycloheptyl and norbornyl. Such groups may be substituted.

"Heterocyclic" aryl or "heteroaryl" groups are groups which have 5-14 ring atoms wherein 1 to 4 heteroatoms are ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted. The term "heterocyclic" refers to cyclic compounds having as ring members atoms of at least two different elements. The compound can be a single ring or a biaryl. Heterocyclic groups include, for example, thiophene, benzothiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Figure 19:
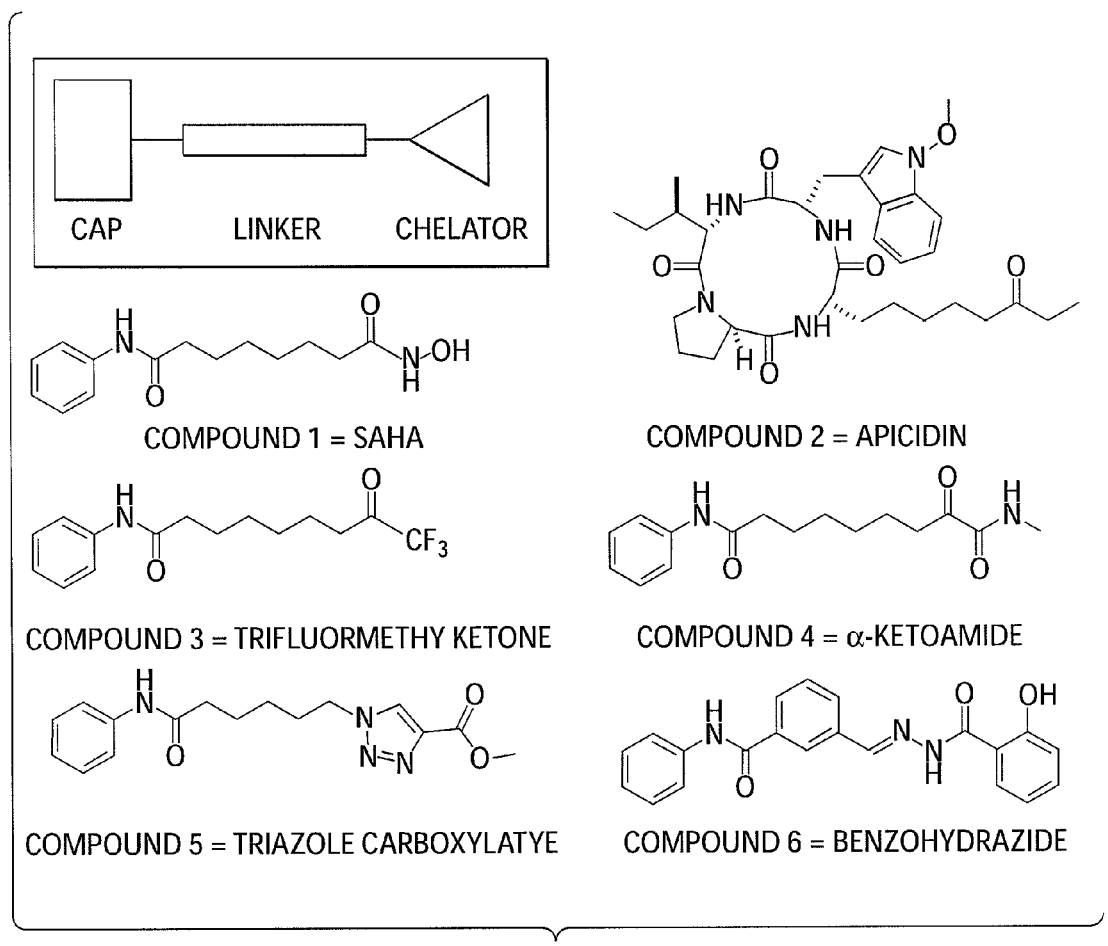
FIG. 19 depicts chemical analogs and the SAHA lead structure. Based upon the lead structure of SAHA (Compound 1), and the "cap-linker-chelator" model for the design of HDAC inhibitors, analogs of SAHA are developed to improve potency and selectivity for class II HDACs.

Based upon the lead structure of the compounds described herein such as SAHA (Compound 1, shown in FIG. 19), and the "cap-linker-chelator" model for the design of HDAC inhibitors, analogs of SAHA may be developed to improve potency and selectivity for class II HDACs. The non-hydroxamate apicidin (Compound 2, FIG. 19) may be obtained from commercial sources (Fermentek). Compound 3 (FIG. 19), an electrophilic ketone with known submicromolar HDAC inhibitory activity, may be synthesized as described by (Frey R R, et al Trifluoromethyl ketones as inhibitors of histone deacetylase. Bioorg Med Chem Lett 2002; 12:3443-3447). Compound 4 (FIG. 19), also an electrophilic ketone may be synthesized based upon the methods of (Wada C K, et al Alpha-keto amides as inhibitors of histone deacetylase. Bioorg Med Chem Lett 2003; 13:3331-3335). The purities of all compounds may be assessed by HPLC and the mass spectra are confirmed relative to anticipated product structures. Compounds may be profiled using a panel of all 11 human recombinant HDACs (BPS Biosciences) to derive selectivity profiles and to explore cofactor dependencies. In parallel, the cellular IC50 for HDAC inhibition may be determined using a panel of antibody-based assays (see e.g. Haggarty S J et al Multidimensional chemical genetic analysis of diversity-oriented synthesis-derived deacetylase inhibitors using cell-based assays. Chem Biol 2003a; 10:383-396.).

Another HDAC inhibitor is Trapoxin (cyclo-(L-phenylalanyl-L-phenylalanyl-D-pipecolinyl-L-2-amino-8-oxo-9,10-epoxy-decanoyl)). Trapoxin is a microbially derived epoxide-containing cyclotetrapeptide that inhibits histone deacetylation in vivo and causes mammalian cells to arrest in the cell cycle.

Trichostatin is another HDAC inhibitor. Trichostatins like many of the HDAC inhibitors are commercially available from sources such as Sigma, Vincibiochem (Italy) etc. Exemplary methods of preparing trichostatin are described in U.S. Pat. No. 4,946,999.

Trichostatin A, SAHA, and trapoxin stimulate histone acetylation by acting as direct inhibitors of HDAC enzyme activity. Each of these compounds possess lysine-like side chains and act as chemical analogs of lysine substrates. Molecular models based upon the x-ray crystal structure of an HDAC-like protein indicate that trichostatin A and SAHA can bind within the active site of the HDAC enzyme and interact with a zinc metal ion within the catalytic pocket that is critical for enzymatic activity.

HDAC inhibitors also include short chain fatty acids such as Sodium Butyrate, Isovalerate, Valerate, 4 Phenylbutyrate (4-PBA), Phenylbutyrate (PB), Propionate, Butyramide, Isobutyramide, Phenylacetate, 3-Bromopropionate, Tributyrin, Valproic Acid and Valproate and Pivanex™.

A DNA methylation inhibitor is an agent that directly or indirectly causes a reduction in the level of methylation of a nucleic acid molecule. DNA methylation inhibitors are well known and routinely utilized in the art and include, but are not limited to, inhibitors of methylating enzymes such as methylases and methyltransferases. Non-limiting examples of DNA methylation inhibitors include 5-azacytidine, 5-aza-2'deoxycytidine (also known as Decitabine in Europe), 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine, and procainamide, Zebularine, and (−)-egallocatechin-3-gallate.

In addition to the traditional HDAC inhibitors described above, histone deacetylase and DNA methylating enzymes can also be inhibited by expression inhibitors such as antisense and RNAi mechanisms. Thus, the invention embraces antisense oligonucleotides that selectively bind to nucleic acid molecules encoding a histone deacetylase or DNA methylating enzyme to decrease expression and activity of this protein.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense oligonucleotides that selectively bind to a nucleic acid molecule encoding a histone deacetylase are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon the nucleotide sequences of nucleic acid molecules encoding histone deacetylase, (e.g., GenBank Accession Nos NP_848512, NP_848510, NP_478057, NP_478056, NP_055522) or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al., Nat. Med. 1(11):1116-1118, 1995. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439-457, 1994) and at which proteins are not expected to bind.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acid molecules encoding a histone deacetylase, together with pharmaceutically acceptable carriers. Antisense oligonucleotides may be administered as part of a pharmaceutical composition. In this latter embodiment, it may be preferable that a slow intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a subject.

The methods of the invention also encompass use of isolated short RNA that directs the sequence-specific degradation of a histone deacetylase mRNA through a process known as RNA interference (RNAi). The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of histone deacetylase mRNAs for degradation in mammalian cells useful in the therapeutic applications discussed herein.

The methods for design of the RNA's that mediate RNAi and the methods for transfection of the RNAs into cells and animals is well known in the art and are readily commercially available (Verma N. K. et al, J. Clin. Pharm. Ther., 28(5):395-404 (2004), Mello C. C. et al. Nature, 431(7006)338-42 (2004), Dykxhoorn D. M. et al., Nat. Rev. Mol. Cell. Biol. 4(6):457-67 (2003) Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 tµmol-scale RNA synthesis provides about 1 milligram of RNA, which is sufficient for 1000 transfection experiments using a 24-well tissue culture plate format.

The histone deacetylase cDNA specific siRNA is designed preferably by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The histone deacetylase siRNA may be designed by a search for a 23-nt sequence motif AA(N19). If no suitable sequence is found, then a 23-nt sequence motif NA(N21) may be used with conversion of the 3' end of the sense siRNA to TT. Alternatively, the histone deacetylase siRNA can be designed by a search for NAR (N17)YNN. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2'hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 that are hereby incorporated by reference in their entirety.

The methods described herein are used to identify or obtain RNA molecules that are useful as sequence-specific mediators of histone deacetylase mRNA degradation and, thus, for inhibiting histone deacetylase activity. Expression of histone deacetylase can be inhibited in humans in order to prevent the protein from being translated and thus contributing to the increased recapture of memories.

The RNA molecules may also be isolated using a number of techniques known to those of skill in the art. For example, gel electrophoresis can be used to separate RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate RNAs.

Any RNA can be used in the methods of the present invention, provided that it has sufficient homology to the histone deacetylase gene to mediate RNAi. The RNA for use in the present invention can correspond to the entire histone deacetylase gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 bp in length. In another embodiment, the RNA is about 500 bp in length. In yet another embodiment, the RNA is about 22 bp in length. In certain embodiments the preferred length of the RNA of the invention is 21 to 23 nucleotides.

Further, histone deacetylase DNA methylating enzymes can also be inhibited by binding peptides such as antibodies. Numerous histone deacetylase antibodies are commercially available from sources such as Sigma, Vinci Biochem, Cell Signaling Technologies. Such antibodies can be modified to produce antibody fragments or humanized versions. Alternatively therapeutically useful antibodies can be produced using techniques known to those of ordinary skill in the art since HDACs are available.

The therapeutic compounds of the invention may be directly administered to the subject or may be administered in conjunction with a delivery device or vehicle. Delivery vehicles or delivery devices for delivering therapeutic compounds to surfaces have been described. The therapeutic compounds of the invention may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus calmatte-guerin, Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term effective amount of a therapeutic compound of the invention refers to the amount necessary or sufficient to realize a desired biologic effect. For example, as discussed above, an effective amount of a therapeutic compounds of the invention is that amount sufficient to re-establish access to a memory. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compounds of the invention without necessitating undue experimentation. Compositions of the invention include compounds as described herein, or a pharmaceutically acceptable salt or hydrate thereof.

Subject doses of the compounds described herein for delivery typically range from about 0.1 μg to 10 mg per administration, which depending on the application could be given daily, weekly, or monthly and any other amount of time therebetween. The doses for these purposes may range from about 10 μg to 5 mg per administration, and most typically from about 100 μg to 1 mg, with 2-4 administrations being spaced days or weeks apart. In some embodiments, however, parenteral doses for these purposes may be used in a range of 5 to 10,000 times higher than the typical doses described above.

In one embodiment, the composition is administered once daily at a dose of about 200-600 mg. In another embodiment, the composition is administered twice daily at a dose of about 200-400 mg. In another embodiment, the composition is administered twice daily at a dose of about 200-400 mg intermittently, for example three, four, or five days per week. In another embodiment, the composition is administered three times daily at a dose of about 100-250 mg. In one embodiment, the daily dose is 200 mg, which can be administered once-daily, twice-daily, or three-times daily. In one embodiment, the daily dose is 300 mg, which can be administered once-daily or twice-daily. In one embodiment, the daily dose is 400 mg, which can be administered once-daily or twice-daily. The HDAC inhibitor can be administered in a total daily dose of up to 800 mg once, twice or three times daily, continuously (i.e., every day) or intermittently (e.g., 3-5 days a week).

For any compound described herein the therapeutically effective amount can be initially determined from animal models. A therapeutically effective dose can also be determined from human data for HDAC inhibitors which have been tested in humans (e.g. for the treatment of cancer) and for compounds which are known to exhibit similar pharmacological activities. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compounds of the invention can be administered to a subject by any mode that delivers the therapeutic agent or compound to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, rectal and intracerebroventricular.

For oral administration, the therapeutic compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the therapeutic compounds of the invention. The therapeutic agent is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a therapeutic compound of the invention optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The therapeutic agents of the invention may be delivered with other therapeutics for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory recall.

The present invention is further illustrated by the following Examples, which in no way should be construed as further limiting.

EXAMPLES

The following examples involve the use of a CK-p25 Tg mouse model to evaluate therapeutic strategies aimed at restoring learning and the access to long-term memory after synaptic and neuronal loss had already occurred. We show that up-regulation of the plasticity and function of the remaining neurons reinstates learning and memory in a degenerated brain. CK-p25 Tg mice allow for control of the onset and extent of neurodegeneration, thereby accessing the determinants of consolidated long-term memories experimentally. It was previously shown that a single fear conditioning trial results in a stable long-term memory that is initially encoded in the hippocampus but likely transferred to the cortical network after 3-4 weeks (7). A similar time-window is reported for human long-term memories (8).

The methods show a distinction between the learning and memory aspects of neurodegenerative disease. The invention provides methods both for the treatment of long-term memory loss and memory lapse. In some embodiments these treatments are directed towards subjects with neurodegenerative disease and synaptic loss. Individuals suffering from neurodegenerative diseases can display impairments that draw a distinction between learning & memory. For example, while patients have difficulty learning new information, they also suffer from inability to recognize close relatives and other attributes of long-term memory. In some aspects the invention provides methods for the recovery of impaired learning and lost long-term memories after animals developed severe neurodegeneration and synaptic loss.

Methods

Environmental enrichment: Up to four mice were continuously housed in a cage that contained two wheels for voluntary running and a variety of toys (obtained form from Petco) to create tunnels, and climbing devices. Food and water was ad libitum. The food was hidden within the bedding. Toys and running wheels were changed on a daily basis.

Learning tests: All behavioral testing is described in Fischer et al. (3).

Cannulation and injection: Microcannula were inserted into the lateral brain ventricles as described by Fischer et al. (24). Sodiumbutyrate (Sigma; St. Louis, Mo.) was dissolved in artificial cerebrospinal fluid (aCSF). A stock solution of TSA (Sigma) was dissolved in DMSO and diluted with aCSF before injection.

Immunoblotting and staining: Lysates for immunoblotting were prepared as described by Fischer et al. (3). To isolate histones, brain tissue was homogenized in TX-buffer (50 mM Tris HCL, 150 mM NACL, 2 mM EDTA, 1% Triton-100) and incubated at 4° C. for 15 min prior to centrifugation at 200 rpm for 10 min. After a wash-step in TX-buffer the pellet was dissolved in TX-buffer containing 0.2M HCl and incubated on ice for 30 min, before a second centrifugation at 10000 rpm for 10 min. The supernatant was either dialysed or directly used for immunoblotting. Antibodies were used in 1:1000 concentrations. All antibodies detecting histones and anti-PSD-95 were form Upstate (Lake Placid, N.Y.). Anti-synaptophysin (SVP38) was from Sigma. Anti-neuronal nuclei (neuN) and anti-growth associated protein (Gap43) were from Chemicon (Temecula, Calif.) and anti-N-cadherin, anti-β-catenin were from Santa Cruz (Santa Cruz, Calif.). Immunostaining was performed as described by Fischer et al. (3). Antibodies mentioned above were used in a 1:500 dilution. Anti-MAP-2 antibody (Sigma) was used in a 1:200 dilution.

Statistical analysis: The data were analyzed by unpaired student's t test and one-way ANOVA (ANalyis OfVAriance). One-way ANOVA followed by post-hoc Scheffe's test was employed to compare means from several groups. Error bars present S.E.M.

Results

Example 1

Figure 1B:
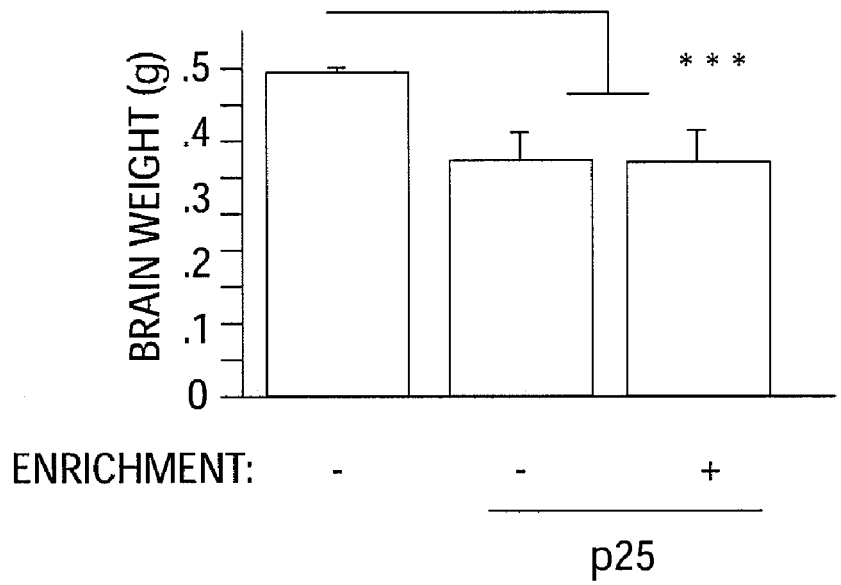
Figure 1C:
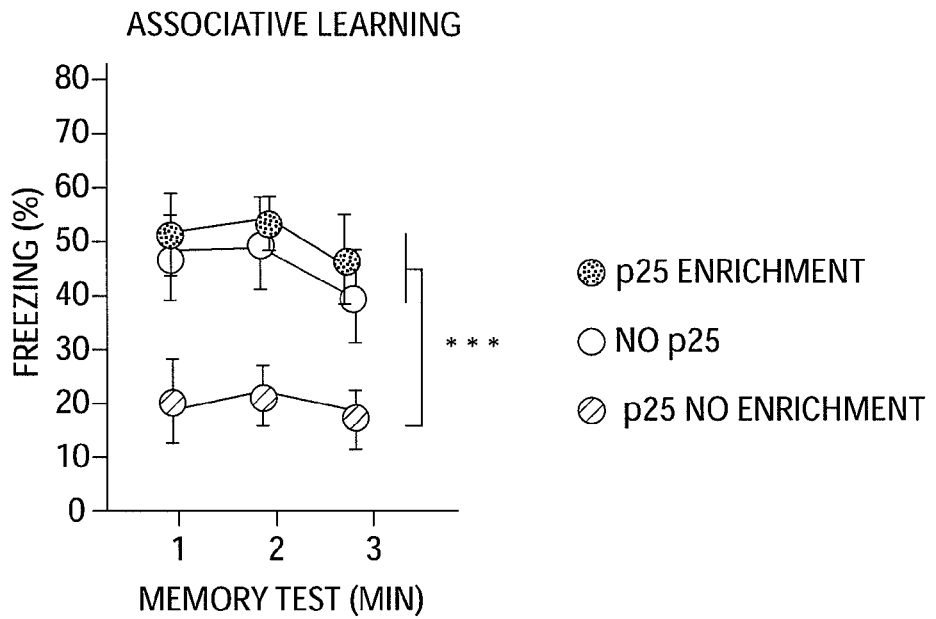
Figure 1D:
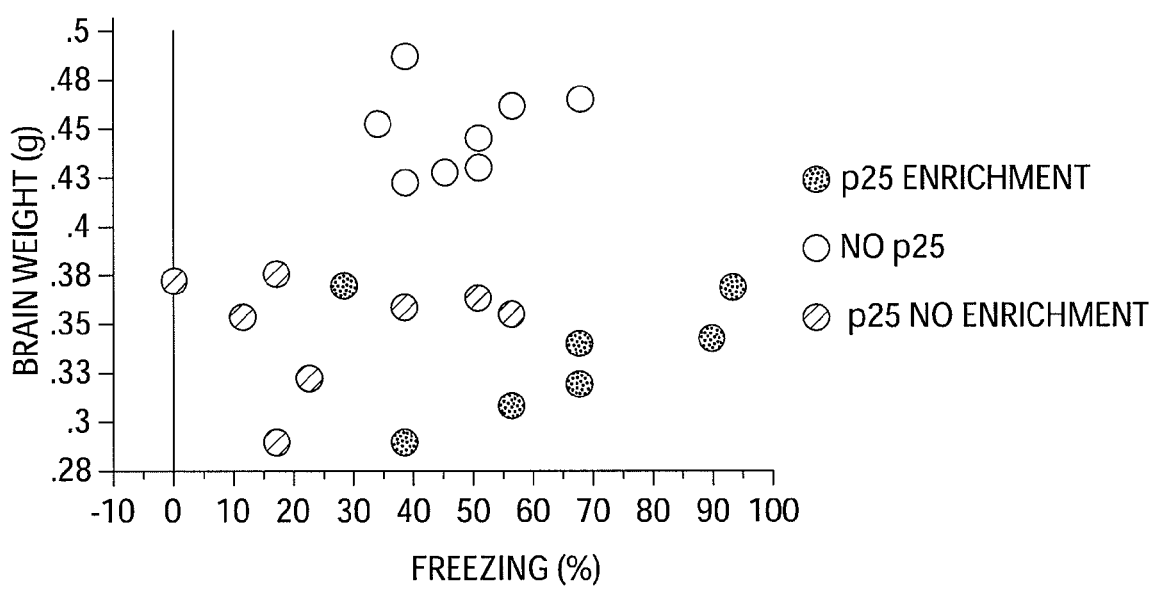
Figure 1E:
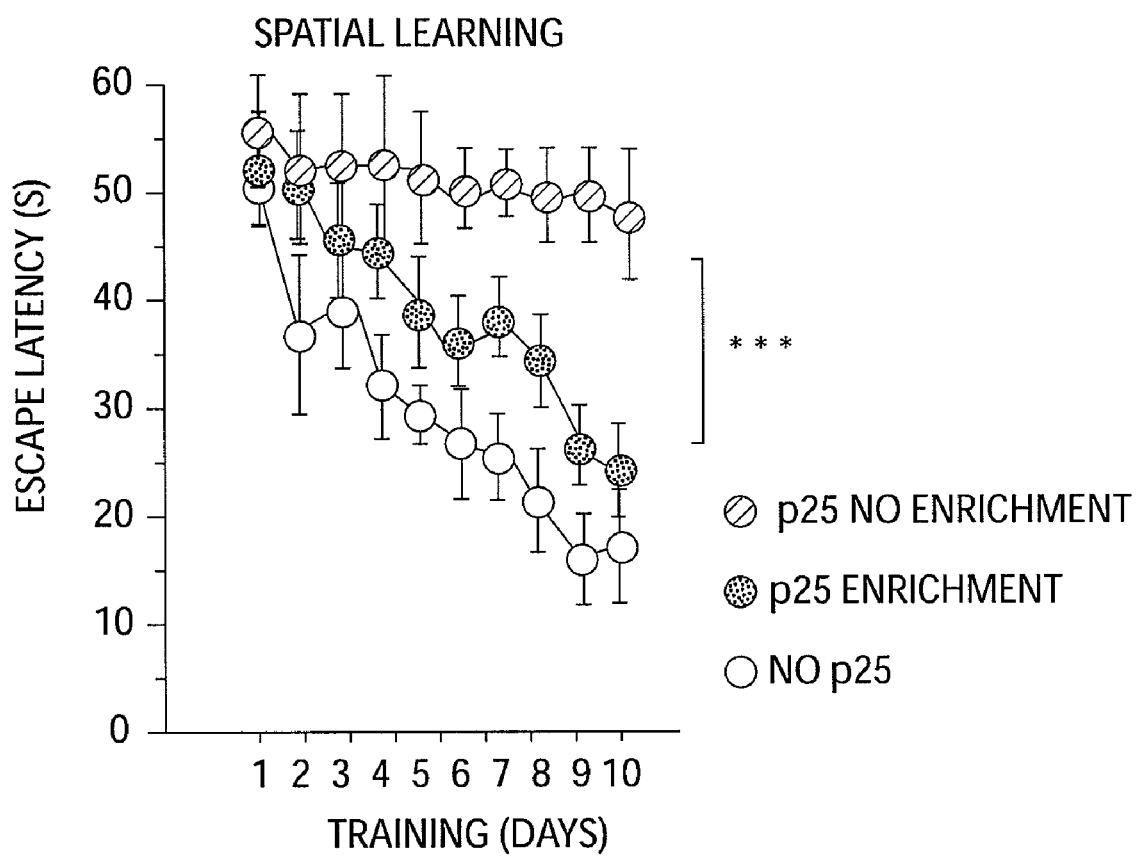
Figure 7A:
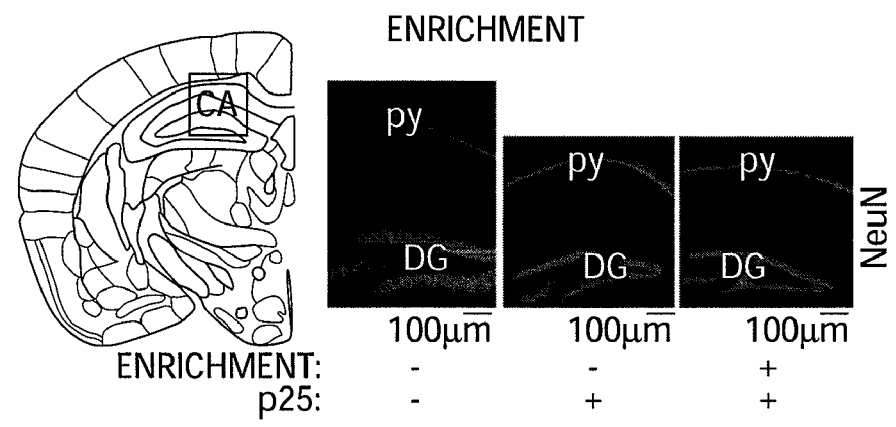
FIG. 7 shows that effects of enrichment or sodiumbutyrate treatment on plasticity factors in CK-p25 Tg mice that developed severe neurodegeneration. a-d. Enrichment of CK-p25 TG mice. a. Representative pictures showing immunostaining for NeuN in the hippocampal region. b. Brain sections immunostained for the dendritic marker protein MAP-2. c. Staining of the anterior cingulated cortex. d. Representative immunoblots from cortical lysates of control mice, enriched and non-enriched CK-p25 Tg mice. e-h. Sodiumbutyrate treatment of CK-p25 Tg mice. e. Representative images showing hippocampal NeuN staining confirming that SB and vehicle injected CK-p25 mice displayed hippocampal neuronal loss to the same degree. f. Representative images showing hippocampal MAP-2 staining. g. Representative images showing NeuN staining of the ACC. h. Representative immunoblots from the hippocampus and cortex of all groups. *P<0.05 vs. vehicle group, n=3. py, pyramidal cell layer; rad, stratum radiatum; Lmol, molecular layer; mol, lower molecular layer; GrDG, granula cell layer of the dentate gyrus, DG, dentate gyrus; CA1, hippocampal regions CA1; cg, cingulate cortex.

The effect of EE on learning behavior after neuronal loss. To investigate the effect of EE on learning behavior after neuronal loss had already occurred, p25 was induced in 11-month old CK-p25 Tg mice for 6 weeks. Afterwards p25 expression was repressed (3) and one group of CK-p25 Tg mice was subjected to EE, whereas the other group was not enriched. Subsequently all mice, including a control group that did not express p25, were subjected to fear conditioning and water maze learning (n=8/group) (FIG. 1a). Despite a comparable extent of brain atrophy (P=0.2435 enriched vs. nonenriched CK-p25 Tg mice; P<0.0001 enriched/non-enriched CK-p25 Tg mice vs. control), EE treated CK-p25 Tg mice showed markedly increased associative and spatial learning when compared to the non-enriched CK-p25 Tg mice (FIG. 1b, FIG. 7a). Non-enriched CK-p25 Tg mice displayed impaired freezing behavior, when compared to control mice (P=0.0337), indicating impaired associative learning. Enriched CK-p25 Tg mice showed significantly more freezing when compared to the non-enriched group (P<0.0001) (FIG. 1c). In addition, the escape latency in the water maze test was significantly impaired in non-enriched CK-p25 Tg mice when compared to control mice ($F_{1,568}$=154,814; P<0.001). Enriched CK-p25 Tg mice performed significantly better than non-enriched CK-p25 mice ($F_{1,568}$=77.167; P<0.0001), but still displayed impaired performance when compared to the control group ($F_{1,568}$=49.453; P<0.0001) (FIG. 1e). These data show that EE can reinstate learning ability in mice with severe neurodegeneration.

Figure 1F:
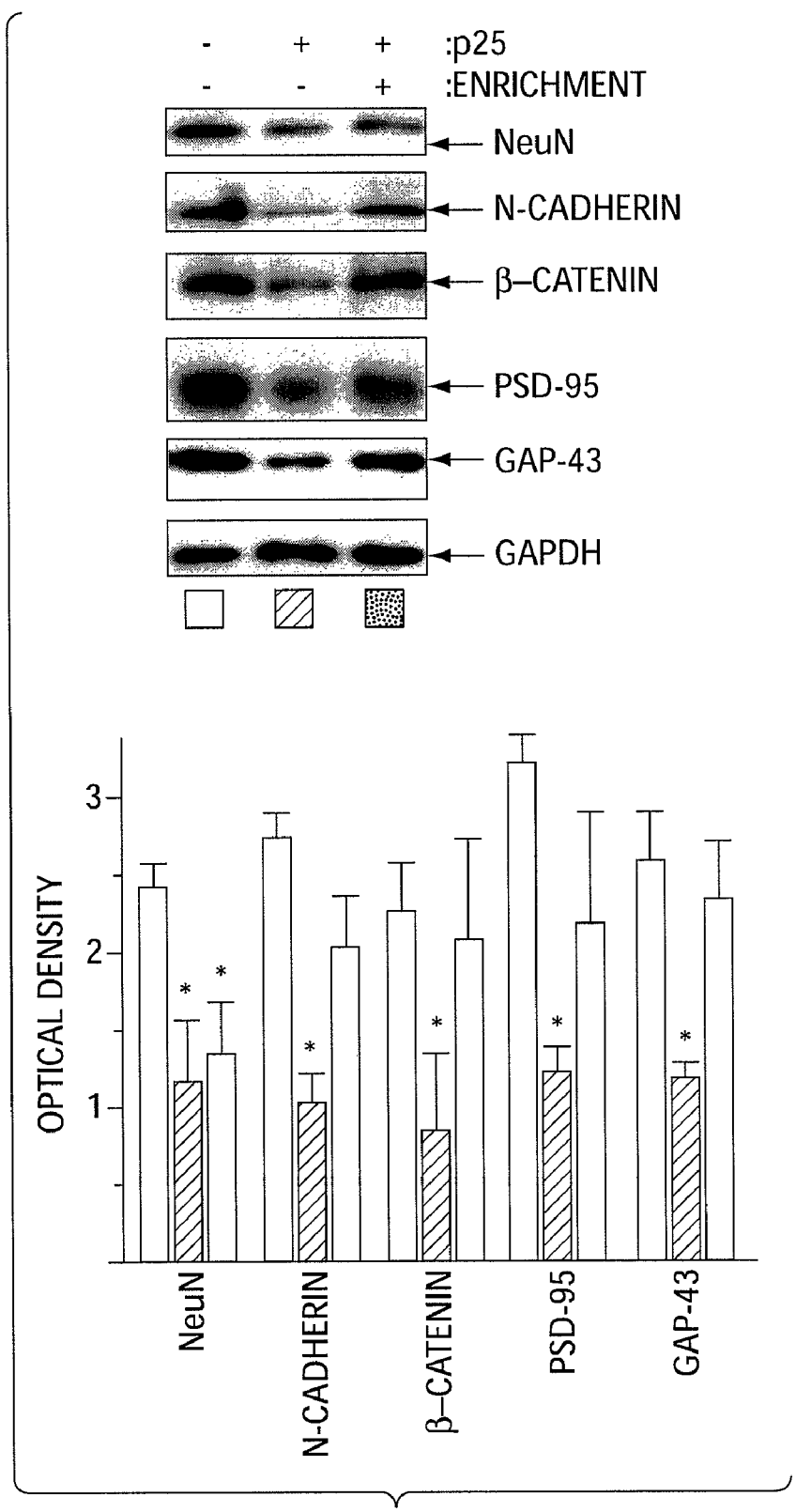
Figure 1G:
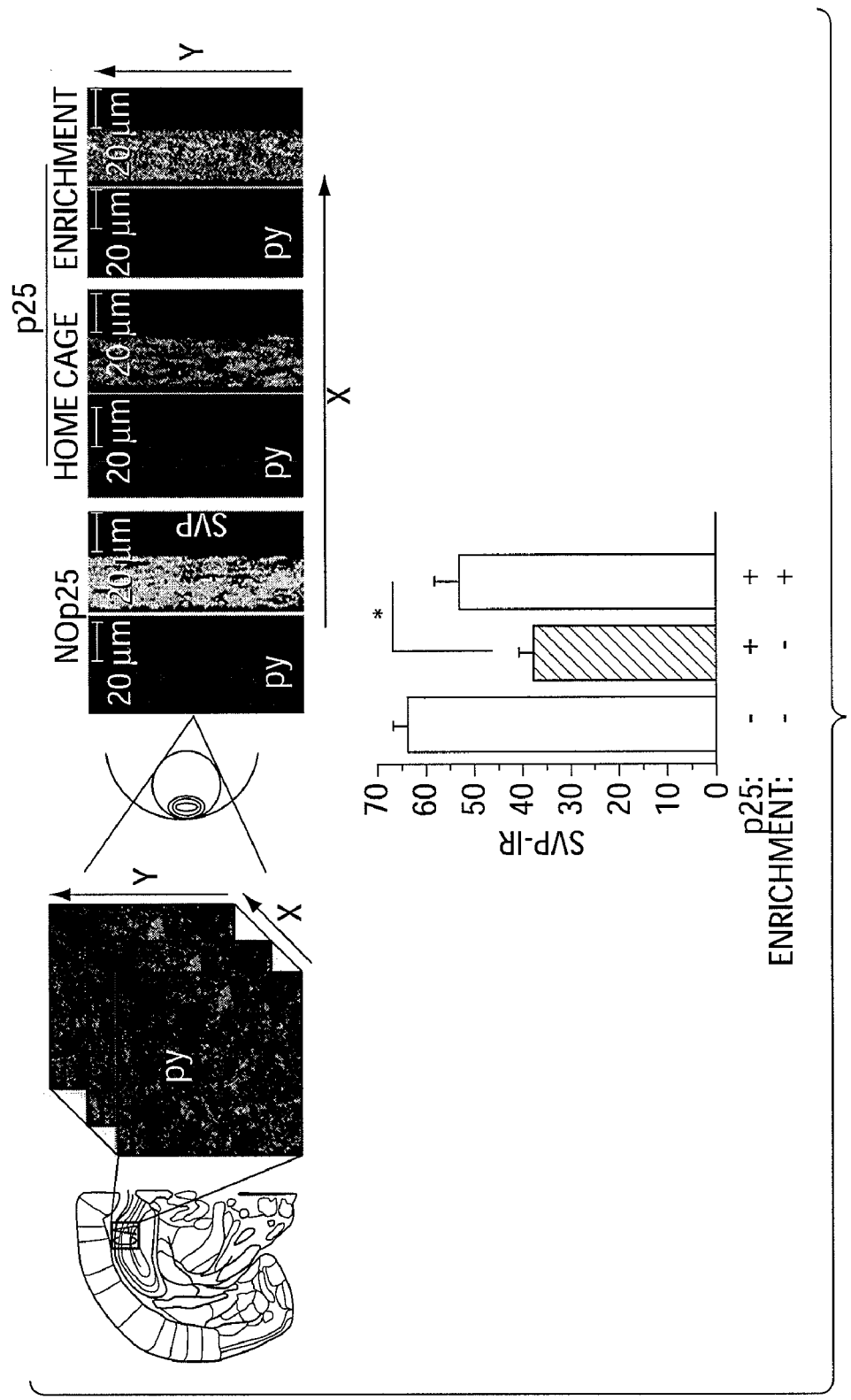

Plotting brain weight against the freezing behavior of individual mice showed that improved learning but not brain weight is associated with EE in CK-p25 Tg mice. No correlation between brain weight and freezing behavior was found (P=0.9993) reflecting that non-enriched and enriched CK-p25 Tg mice display brain atrophy to the same degree but the freezing behavior of enriched CK-p25 Tg mice is similar to the control group that shows no brain atrophy (FIG. 1d). Consistently, the neuronal marker protein NeuN was similarly reduced in EE treated and untreated CK-p25 Tg mice. Notably, levels of synaptic markers proteins, synaptophysin and MAP-2 immunoreactivity (IR) were significantly higher in EE treated CK-p25 Tg mice when compared to non-enriched CK-p25 Tg mice. Although NeuN levels were decreased to similar levels, several markers for synaptic plasticity and integrity were increased in enriched when compared to non-enriched CK-p25 Tg mice (FIG. 1f, g; see also FIG. 7) (*P<0.05 enriched vs. non enriched CK-p25 Tg group, n=3. Quantification (*P<0.05 non enriched CK-p25 Tg group, n=3, vs. control and enriched CK-p25 Tg mice). SVP (synaptic vesicle protein) staining is commonly used to analyze synaptic plasticity in animal models for neurodegeneration or post mortem tissue from human AD patients. Confocal images (1 μm) were scanned and subjected to three-dimensional reconstruction. The pictures are displayed as seen from the x-axis. LSMeta10 software (Zeiss; Jena, Germany) was used to calculate the mean SVP intensity. Brain sections with the strongest intensity were scanned first. All other images included in the analysis where scanned using the same microscope setting. Non-enriched CK-p25 Tg mice showed significantly reduced hippocampal SVP intensity (P<0.0001), when compared to control mice (no p25). Enriched CK-p25 Tg mice displayed significantly increased hippocampal SVP intensity when compared to non-enriched CK-p25 Tg mice (P=0.0304). Scale bar: 20 µm. py, pyramidal cell layer (FIG. 1g).

The data presented in this example indicate that EE promoted growth of new dendrites and synapses in CK-p25 Tg mice. Thus, despite the substantial loss of neurons, EE induced the refinement of the synaptic network, which causes improved learning in the CK-p25 Tg mice. Exposure of wild type mice to EE facilitated their learning ability and caused elevated levels of marker proteins for synaptic integrity and plasticity indicating dendritic branching and synaptogenesis (See also FIG. 5 and FIG. 6).

Example 2

Figure 2A:
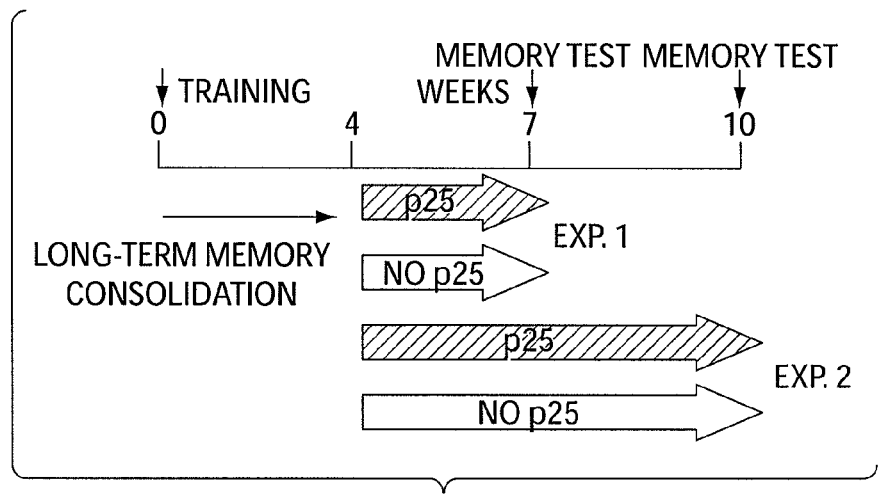
FIG. 2 shows that enrichment reestablishes the access to long-term memories. a. Experimental design I. b. the loss of consolidated long-term memories. c. Experimental design II. d. Memory test: freezing behavior. e. Representative images and plots showing NeuN staining and brain atrophy. f. Representative images of the anterior cingulate cortex region showing staining and plots of the synaptic marker protein synaptophysin (SVP). Scale bar: 20 μm. *P<0.05 vs. non enriched group, n=3. cg, cingulated cortex; M2, motor cortex 2; cc, corpus callosum.
Figure 2B:
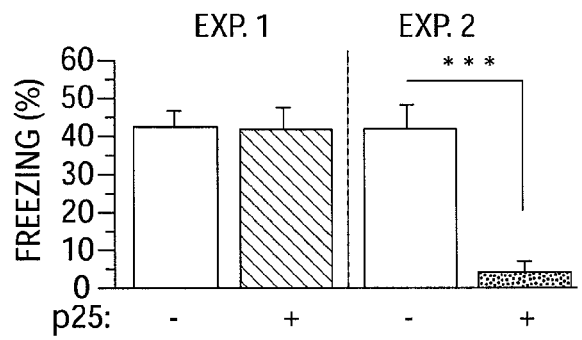
Figure 9A:
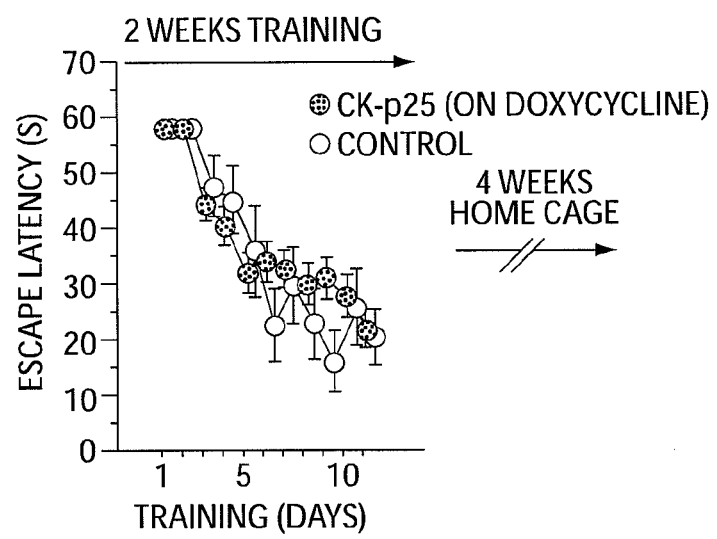
FIG. 9 shows that evidence that enrichment and sodium-butyrate injection lead to the recovery of spatial memories. a. Training of CK-p25 Tg mice in which p25 expression was repressed and control mice were trained in the water maze paradigm. b. Mean escape rate. c. Mean escape rate after EE. d. Mean escape rate after SB injection.

Experimental model for the investigation of long-term memories. To establish an experimental model that allows investigation of the fate of long-term memories, 11-month old CK-p25 Tg and control mice were trained in the fear conditioning paradigm and returned to their home cages for 4 weeks to allow the consolidation of hippocampus-independent long-term memories. Subsequently p25 was induced for either 3 (Exp. 1) or 6 weeks (Exp. 2) before the mice were subjected to the memory test. These time points were chosen because, in contrast to 6-week induction, after 3 weeks of p25 expression no overt pathology was observed (3)(FIG. 2a). In Exp. 1, CK-p25 Tg mice (n=8) showed similar freezing than control mice (n=9; P=0.863) (FIG. 2b; Exp. 1). In contrast, CK-p25 Tg mice induced for 6 weeks (n=9) showed significant reduction in freezing behavior during the memory test performed 10 weeks after the training when compared to the control group (n=16; P<0.0001), showing that the access to long-term memories has been lost. (FIG. 2b; Exp. 2). The loss of consolidated long-term memory was also evident in the water maze paradigm (FIG. 9a, b).

Figure 2C:
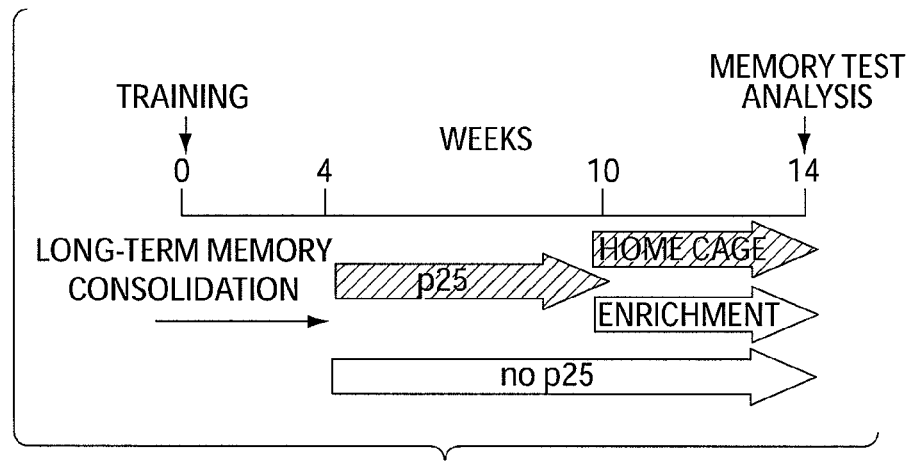
Figure 2D:
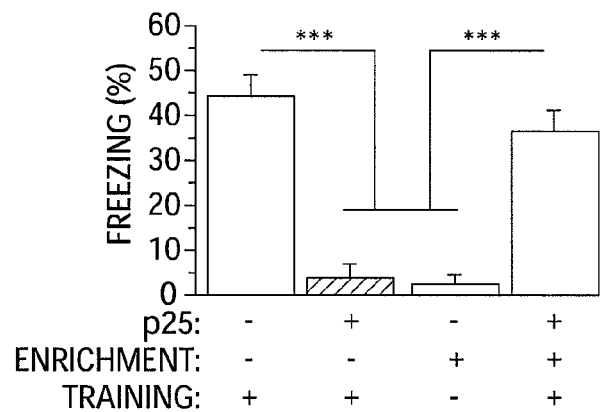

If memories became inaccessible due to synaptic and neuronal loss it might be possible to re-establish the access to such memories if sufficient refinement of the neuronal network can be achieved by the remaining neurons. To investigate if memories became inaccessible due to synaptic and neuronal loss CK-p25 Tg and control mice were trained in the fear conditioning paradigm and returned to their home cages for 4 weeks followed by 6 weeks of p25 induction. Next, the mice were either subjected to EE or kept in their home cages for an additional 4 weeks. The experiment was performed as described under (a) but after 6 weeks of p25 induction, p25 expression was repressed and one group of CK-p25 Tg mice was subjected to EE (n=13) whereas the other group was not enriched (n=9). Control groups consisted of non-enriched mice that were trained but did not express p25 (n=22) and an enriched group that did not express p25 and were not subjected to the training (n=6). (FIG. 2c). Afterwards all mice were subjected to the memory test. Whereas non-enriched CK-p25 Tg mice showed significantly impaired freezing behavior, indicating the loss of long-term memories, enriched CK-p25 Tg mice displayed much improved freezing behavior, indicating a marked recovery of long-term memories. Whereas non-enriched CK-p25 Tg mice displayed decreased freezing when compared to control mice (P<0.0001), enriched CK-p25 Tg mice performed significantly better (P<0.0001 vs. non enriched CK-p25 group) (FIG. 2d).

Figure 2E:
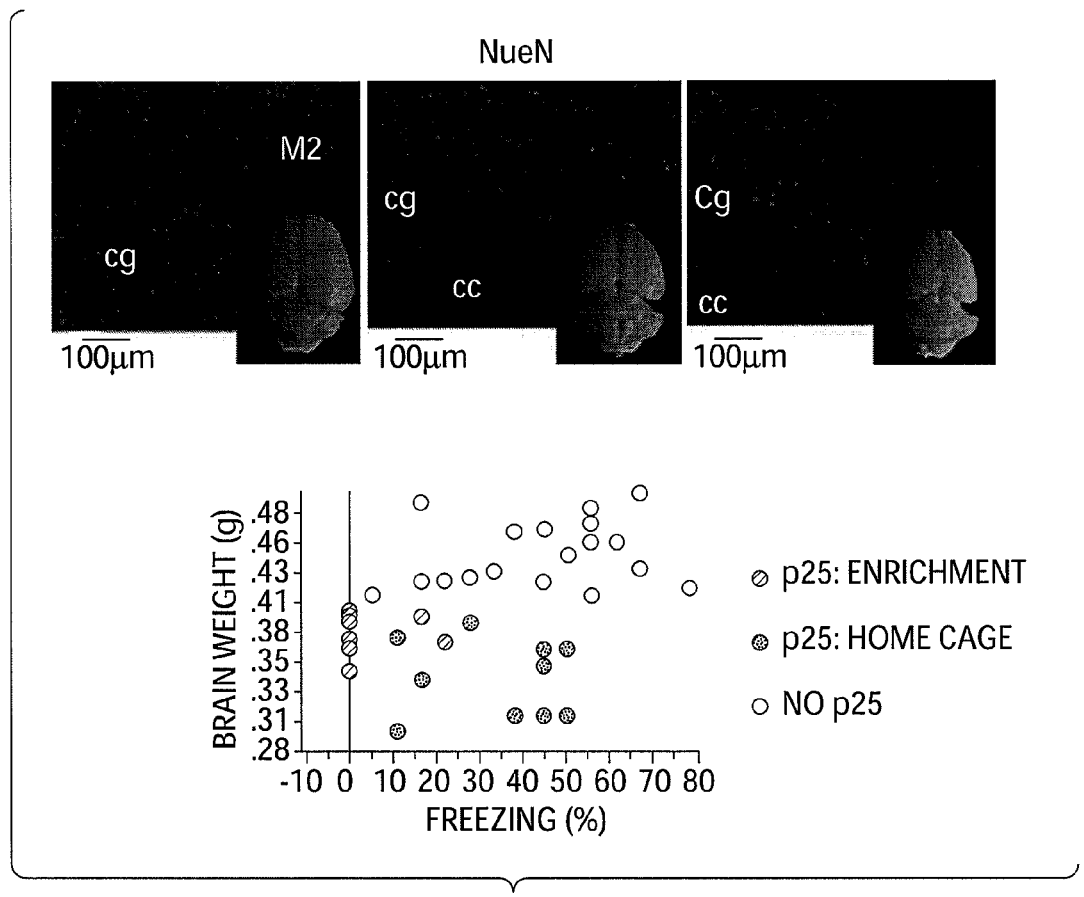

Enriched and non-enriched CK-p25 Tg mice have a similar extent of neuronal loss and brain atrophy in the anterior cingulated cortex (FIG. 2e; Right: Representative images showing NeuN staining and brain atrophy; Left: Brain weight was plotted against freezing behavior). No correlation between brain weight and freezing was found. Evidence for the recovery of long-term memories was also found by employing the water maze paradigm (FIG. 9a, c). The fact that long-term memories can be recovered by EE supports the idea that the apparent "memory loss" is really a reflection of inaccessible memories. These findings are in line with the phenomena known as "fluctuating memories" where demented patients experience temporary time periods of apparent clarity (9, 10).

Figure 2F:
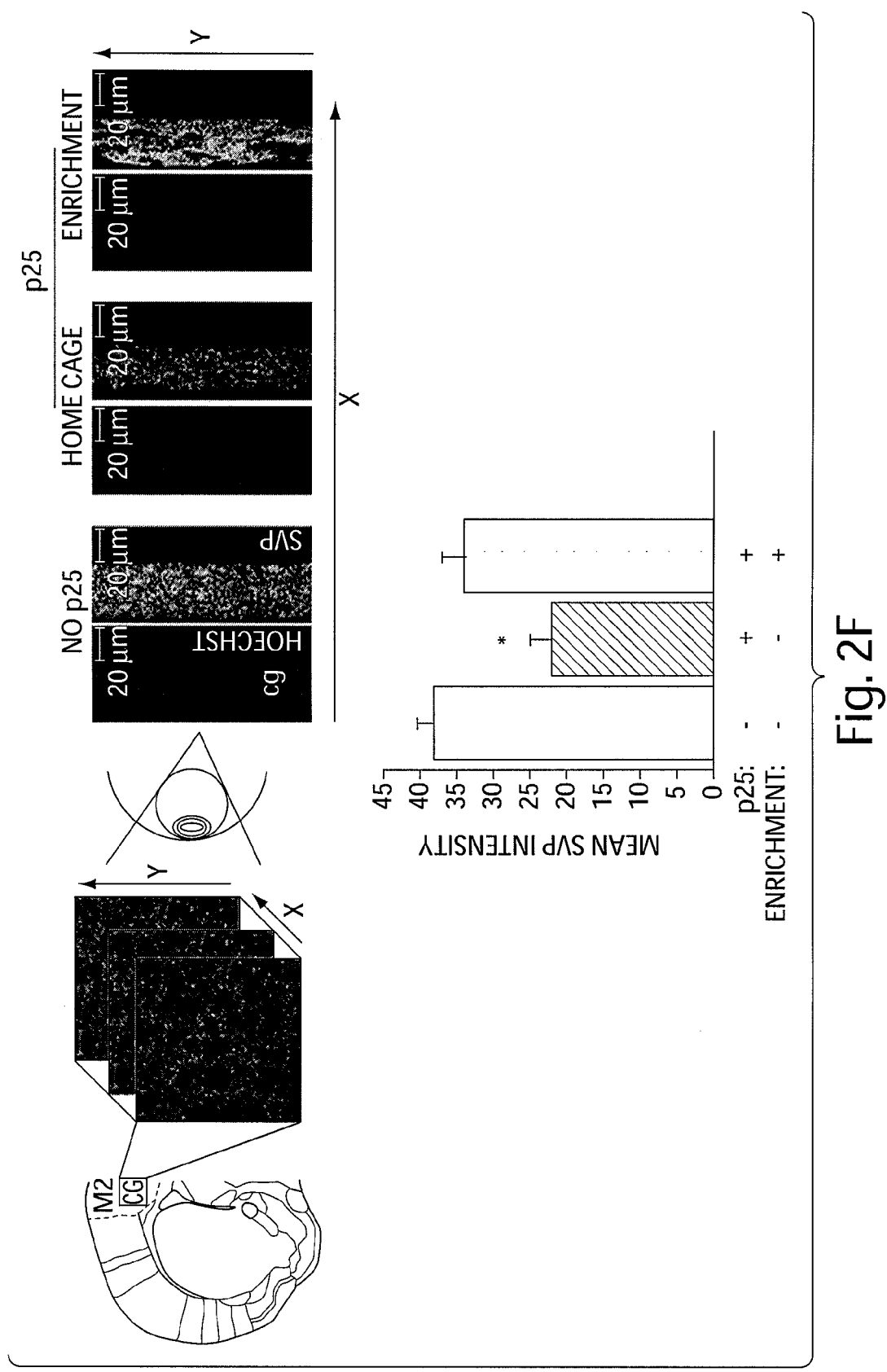
Figure 7B:
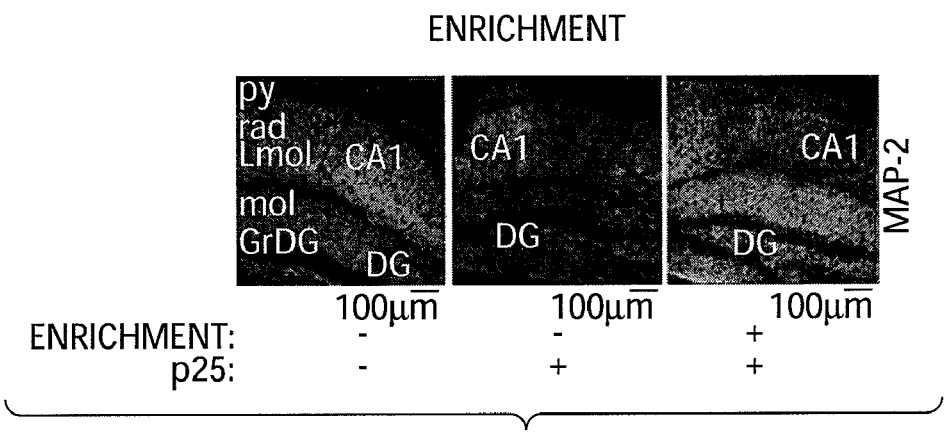
Figure 7C:
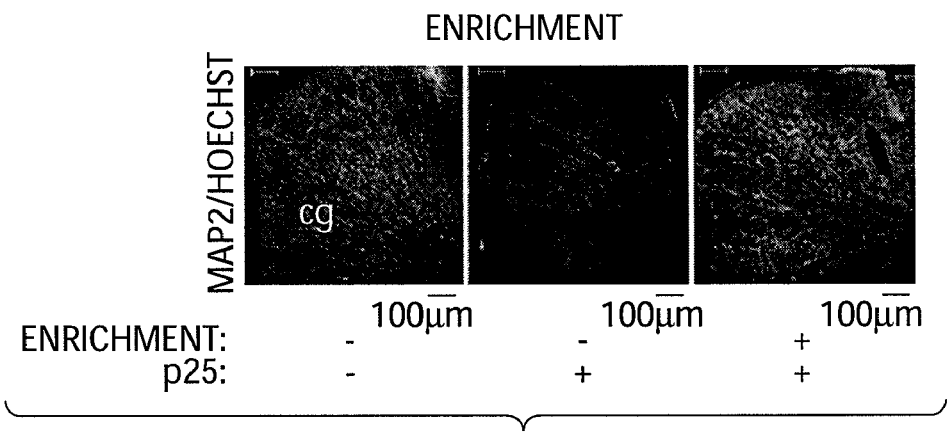

The anterior cingulate cortex (ACC) is implicated with the consolidation and encoding of long-term memories (11). CK-p25 Tg mice with no EE treatment displayed reduced synaptophysin-IR in the ACC when compared to control mice (FIG. 2f). Non-enriched CK-p25 mice showed significantly reduced SVP intensity, when compared to control mice. Enriched CK-p25 mice displayed significantly increased hippocampal SVP intensity when compared to non-enriched CK-p25 mice (P=0.0251). In contrast, cortical levels of synaptic marker proteins, synaptophysin- and MAP-2 IR were increased in enriched, relative to non-enriched CK-p25 Tg mice (FIG. 2f; FIGS. 7c, d). These data show that EE leads to the recovery of long-term memories by re-establishing the synaptic network.

Example 3

Figure 3A:
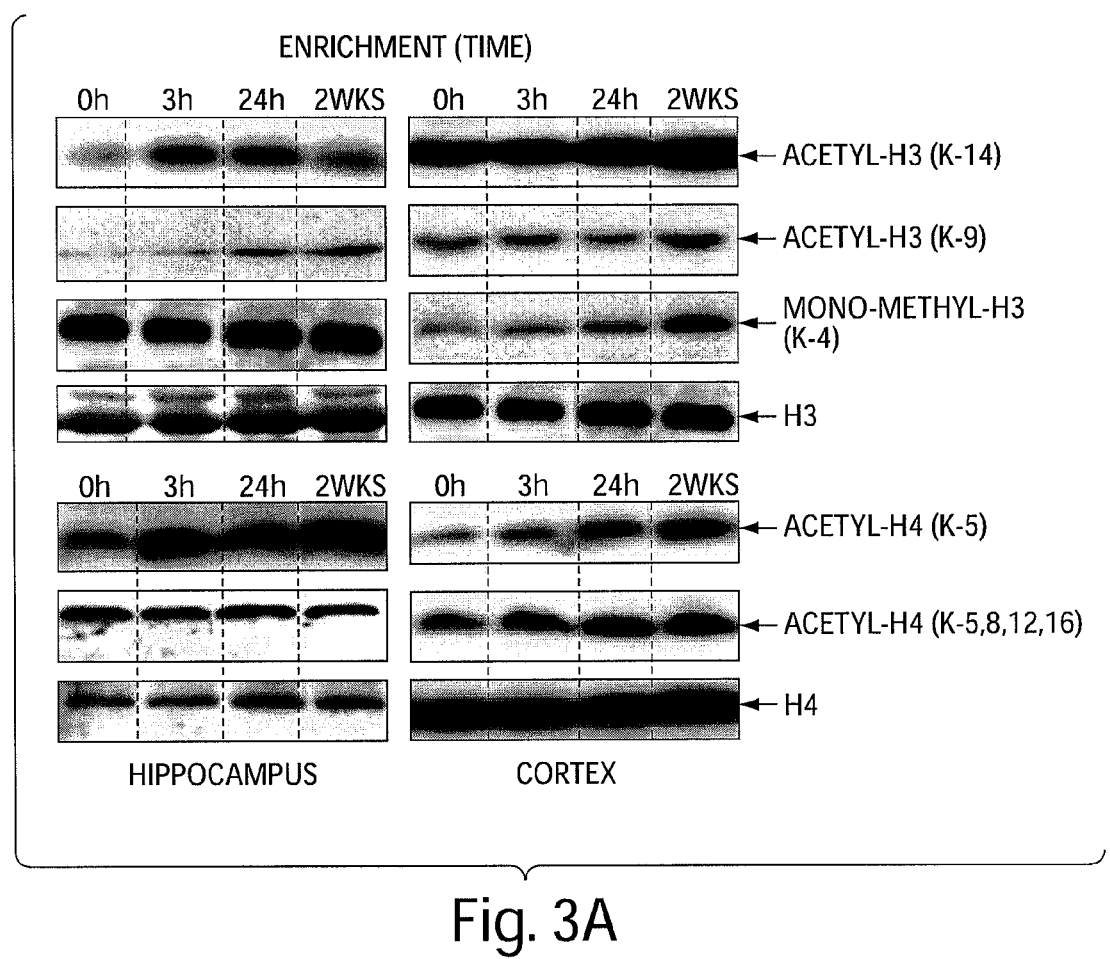
FIG. 3 shows that enrichment induces epigenetic changes and histone-deacetylase inhibitors facilitate learning behavior. a. Acetylation changes upon EE. b. Quantification of A. c.+d. C57BL/6J were injected [ip] daily with SB (1.2 g/kg) or saline for 4 weeks, which resulted in increased acetylation of H3 and H4 in hippocampal lysates. e.+f. SB injected mice showed significantly facilitated associative and spatial learning.
Figure 3B:
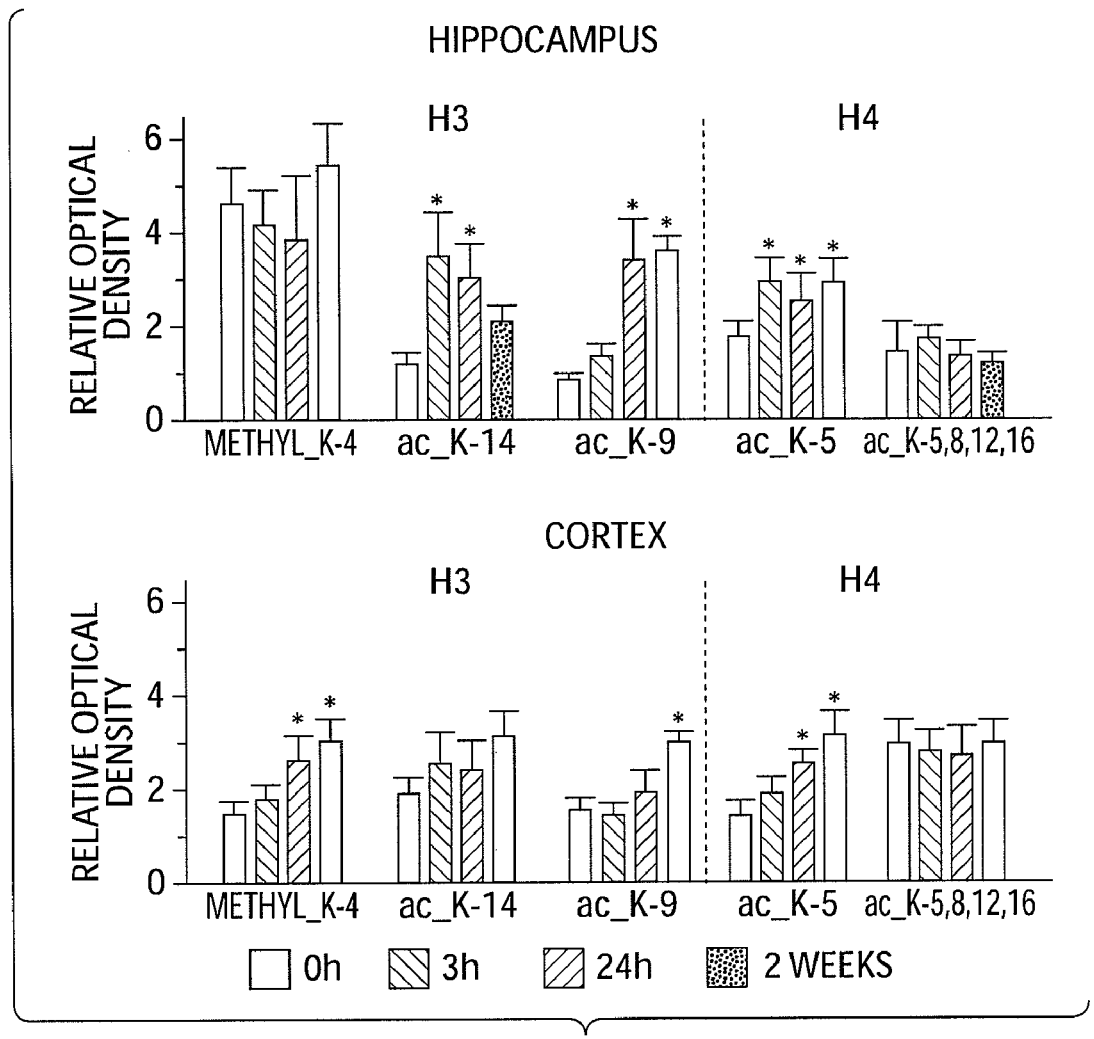
Figure 3C:
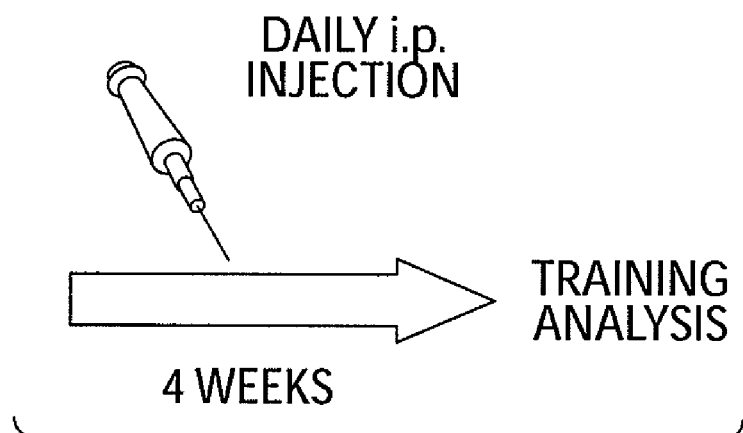
Figure 3D:
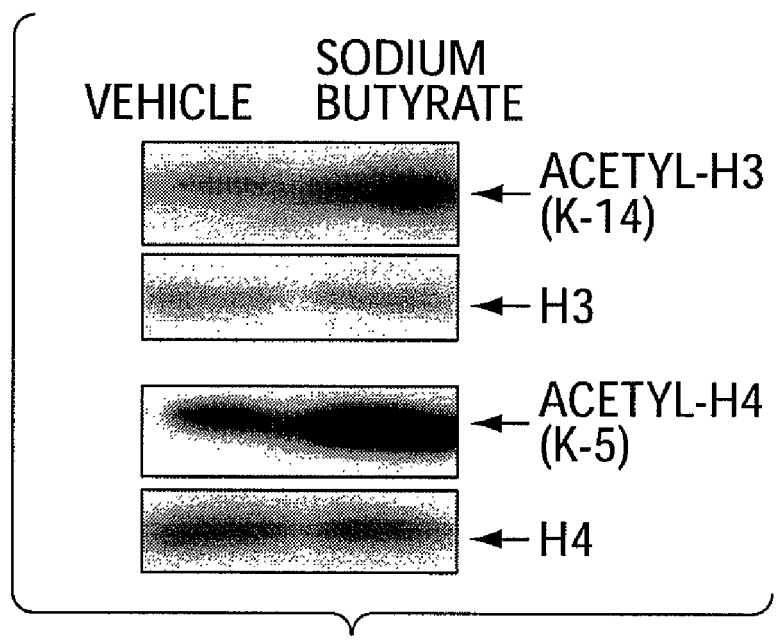
Figure 3E:
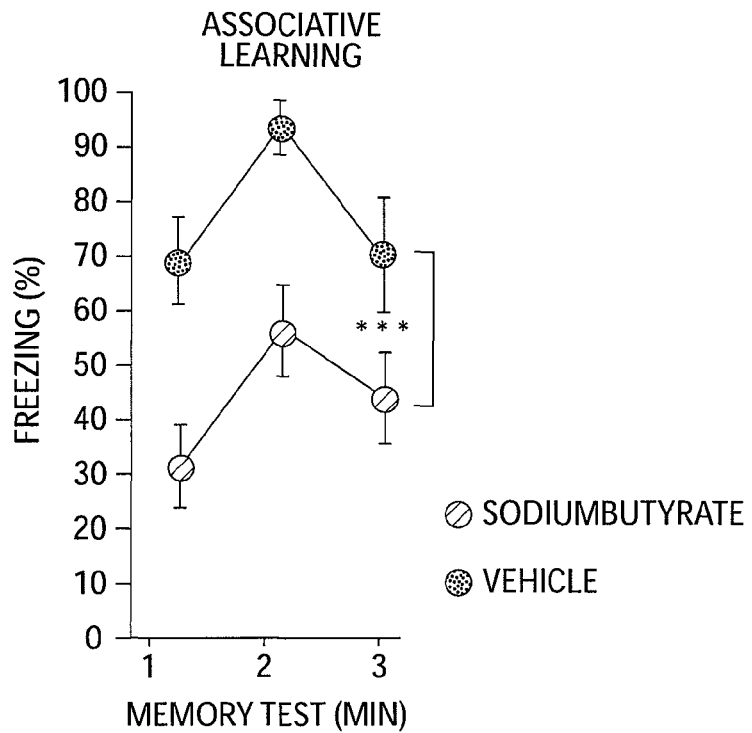
Figure 3F:
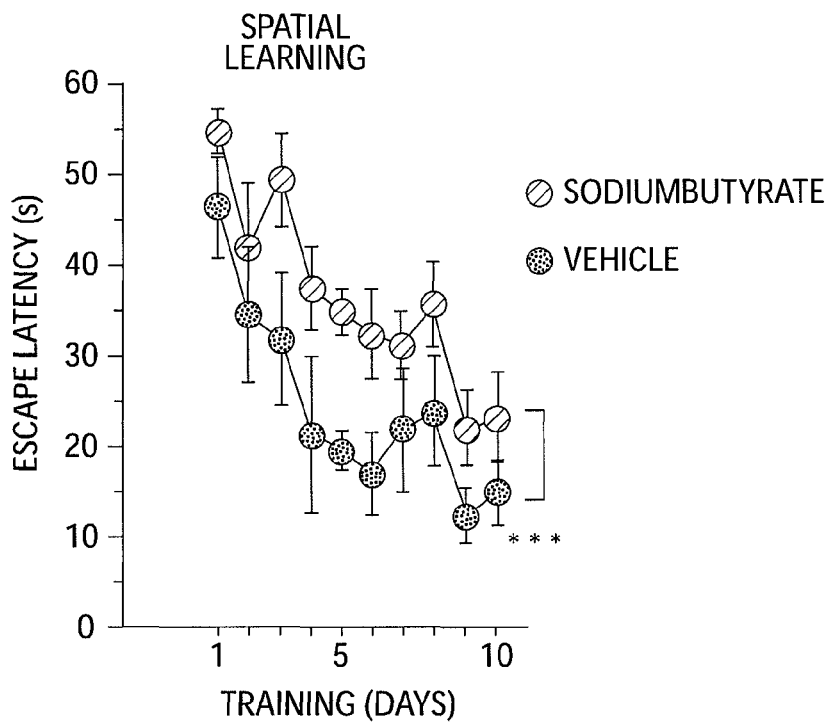
Figure 8D:
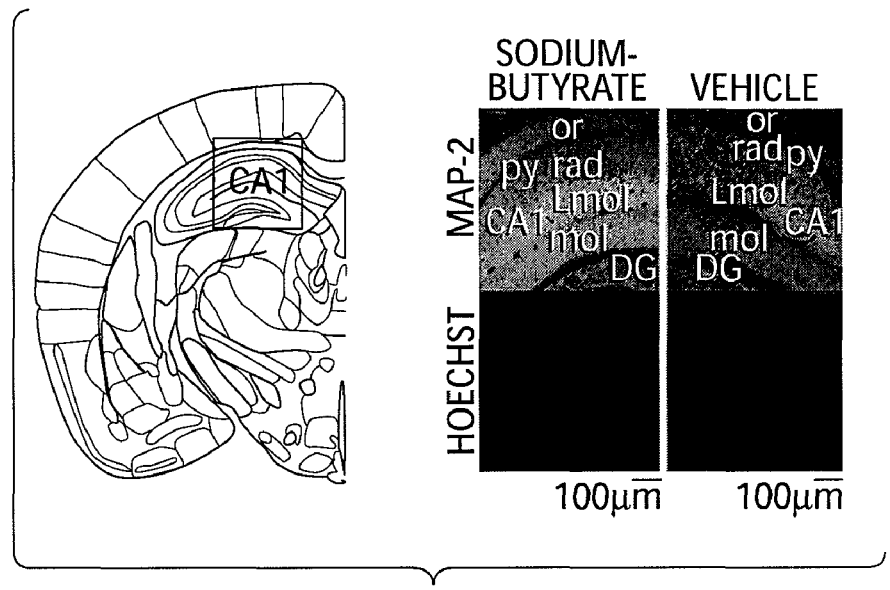
FIG. 8 shows that the effect of sodiumbutyrate injection on learning, basal anxiety, explorative behavior and brain plasticity. a. Freezing behavior during the memory test, ip administration. b. Freezing behavior during the memory test, icv administration. c. Elevated plus maze and open field test. d. Representative images showing increased MAP-2 immunoreactivity (IR) in the hippocampus. e. Representative immunoblots (n=3/group) from hippocampal lysates. f. Representative images showing increased SVP IR in the hippocampus. py, pyramidal cell layer; or, oriens; rad, stratum radiatum; Lmol, molecular layer; mol, lower molecular layer; GrDG, granula cell layer of the dentate gyrus, DG, dentate gyrus; CA1, hippocampal regions CA1; cg, cingulate cortex.
Figure 8E:
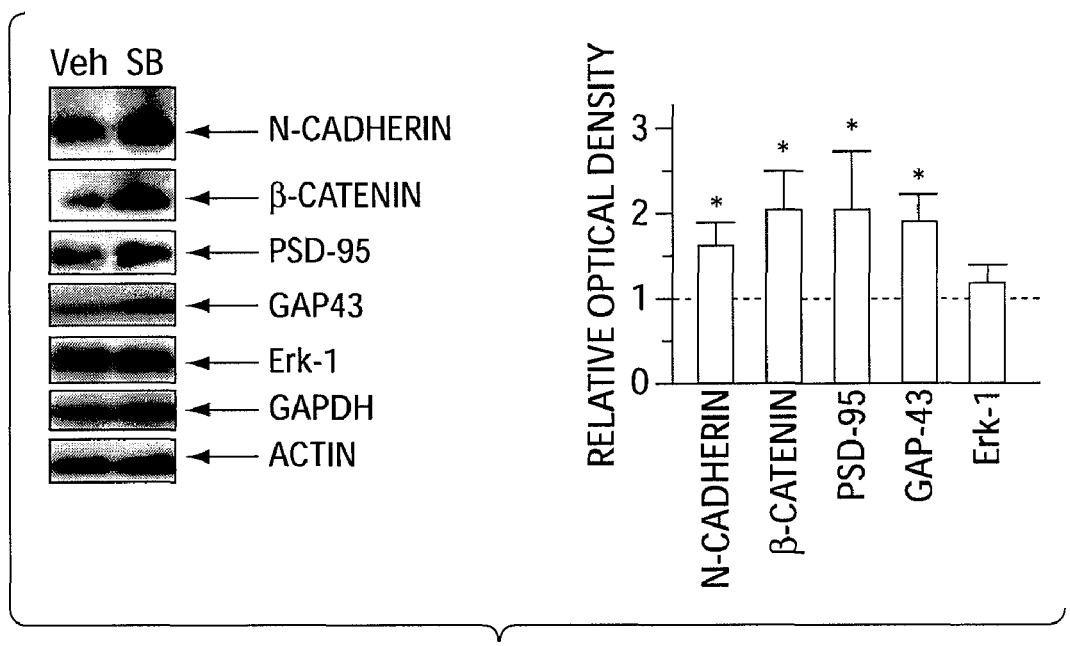
Figure 8F:
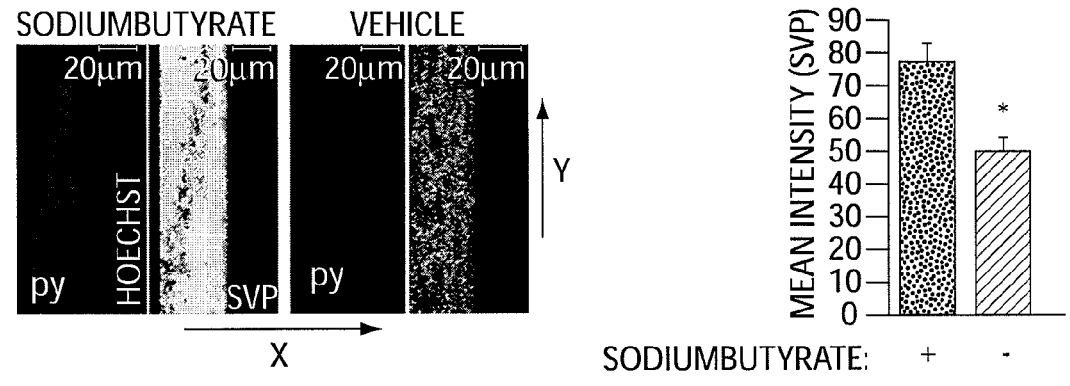

Mechanism underlying EE. Other than a few genes involved in synaptic function, relatively little is known about the mechanism underlying EE (12-14). Since histone acetylation, an epigenetic mechanism regulating gene expression via chromatin remodeling, has recently been implicated in synaptic plasticity and learning behavior (15-18), the induction of a transcriptional program by EE that leads to activation of plasticity genes was evaluated. Wild type mice were subjected to EE and hippocampal and cortical brain lysates were obtained 3, 24 h or 2 weeks later (n=3/group) by acid extraction and probed with antibodies detecting histone-tail modification that indicate active chromatin. Increases in hippocampal H3 (K-9, K14) and H4 (K-5) and in cortical H3 (K-9) and H4 (K-5) acetylation were observed. In addition increased methylation of H3 (K4) was observed in cortical lysates. No changes in H4 acetylation were observed when the Ac-H4 (K,8,12,16) antibody was used, which is likely due to the fact that H4-K16 is a marker of condensed chromatin. EE induced hippocampal and cortical histone 3 (H3) and histone 4 (H4) acetylation and methylation as soon as 3 hours after treatment (FIGS. 3a, b). In addition, intraperitoneal [ip] and intracerebroventricular [icv] injections of histone deacetylases (HDACs) inhibitors sodiumbutyrate (SB) or trichostatin (TSA) significantly facilitated associative learning in wild type mice (FIG. 8a). To investigate whether inhibition of HDACs mimics the effects of EE, SB was administered daily [ip] into wild type mice for 4 weeks (FIG. 3c). This procedure resulted in a robust increase in H3- and H4 acetylation in the hippocampus (FIG. 3d). Two days after the last injection mice were trained in the fear conditioning paradigm. When tested 24 h later, SB injected mice showed more freezing during the memory test (P<0.0001)(FIG. 3e). Similarly, when trained in the water maze paradigm SB injected mice displayed a shorter escape latency ($F_{1,\ 138}$=24.119; P<0.0001)(FIG. 3f) when compared to the vehicle group. In addition increased hippocampal MAP-2 and synaptophysin IR and elevated levels of synaptic and dendritic marker proteins in SB-injected mice was observed (FIG. 8d-f). Locomotor activity or basal anxiety was not altered in SB-injected mice (FIG. 8c).

Example 4

Figure 4A:
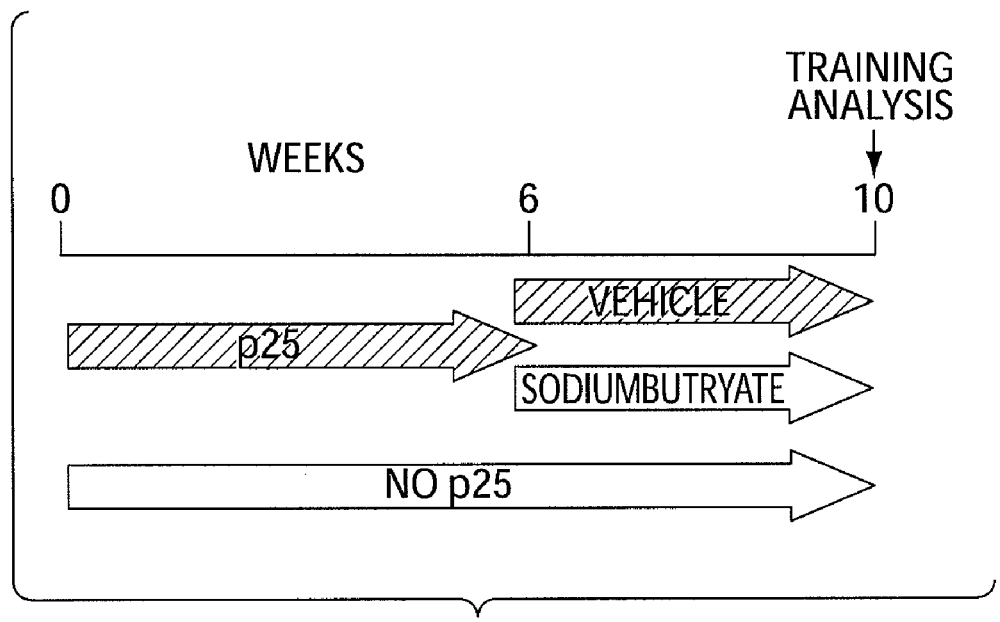
FIG. 4 shows that sodiumbutyrate facilitates learning and reestablishes the access to long-term memories in CK-p25 Tg mice. a. Experimental design. b. Freezing behavior. c. water maze paradigm. d. Representative images showing increased hippocampal SVP-IR in CK-p25 Tg mice injected with SB, when compared to vehicle-injected mice (P<0.0001). Scale bar: 20 μm. Analysis was performed as described in FIG. 1. e. Quantification of (D). f-i. Sodiumbutyrate treatment reinstates access to long-term memories in CK-p25 Tg mice. f. Experimental design. g. Freezing behavior. h. Representative images showing SVP-IR in the ACC(P<0.0001). Scale bar: 20 μm. i. Quantification of (h). py, pyramidal cell layer; cg, cingulate cortex.
Figure 4B:
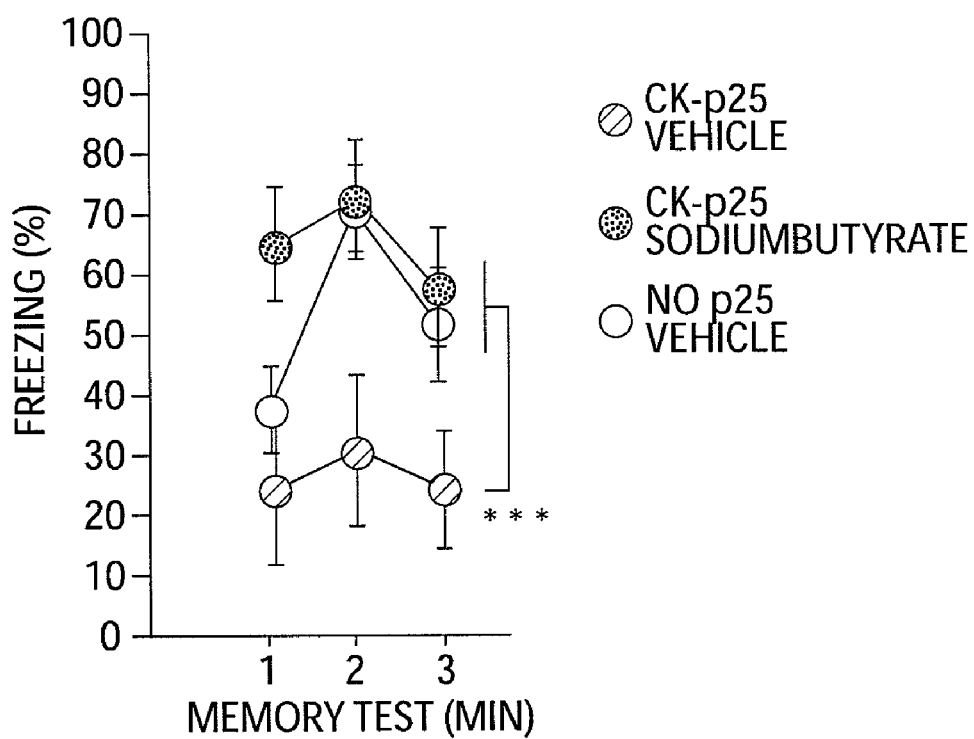
Figure 4C:
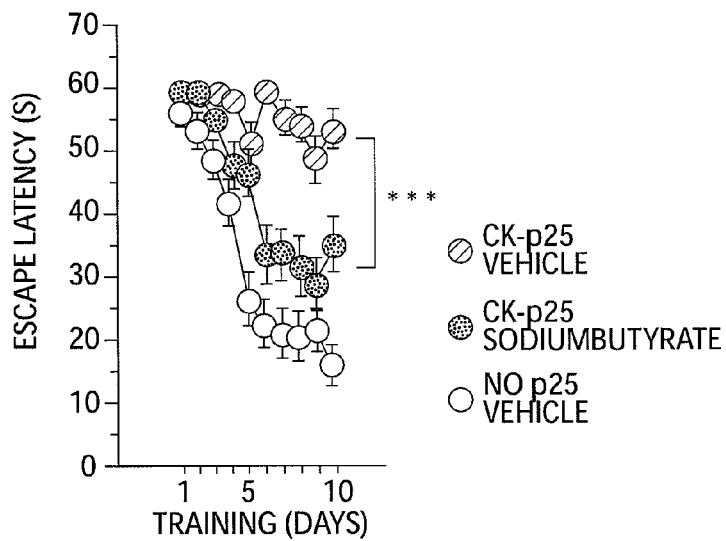
Figure 4D:
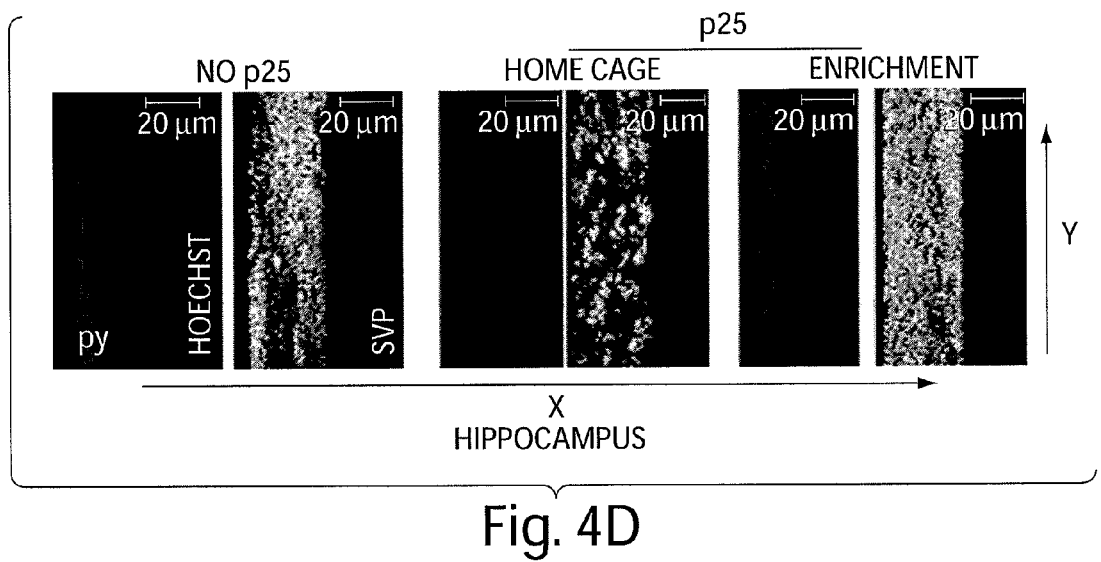
Figure 4E:
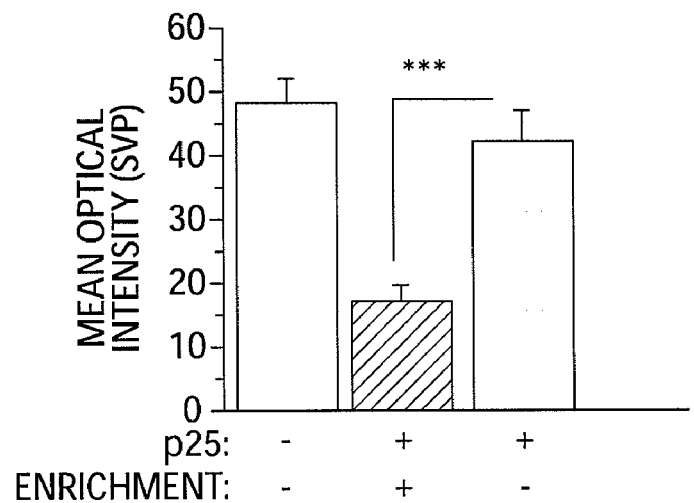
Figure 7D:
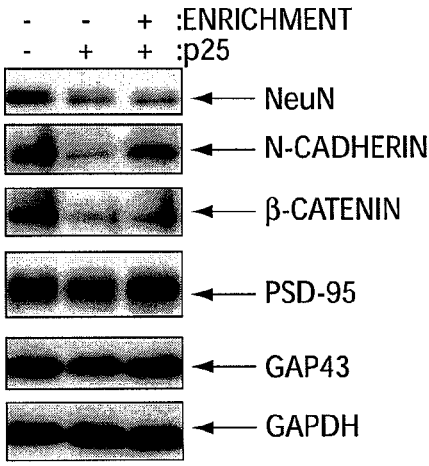
Figure 7E:
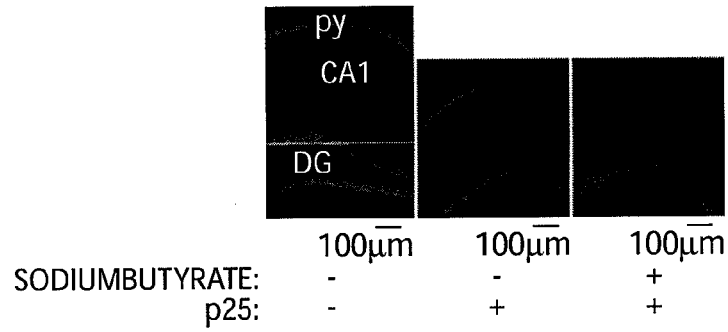
Figure 7F:
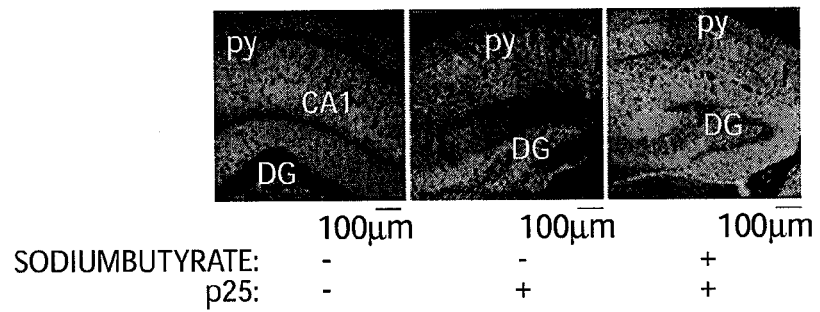

Reinstatement of learning behavior through inhibition of HDAC. Whether sustained inhibition of HDACs would reinstate learning behavior and recover access to long-term memories in CK-p25 Tg mice that had developed synaptic and neuronal loss was investigated. P25 was induced in 11 month old CK-p25 Tg mice for 6 weeks. Afterwards p25 expression was repressed and one group of CK-p25 Tg mice was subjected to daily sodiumbutyrate (SB) injection (1.2 g/kg) for 4 weeks (n=9), whereas the other group received saline injection (n=9). Subsequently all mice, including a control group that did not express p25 (n=9), were subjected to fear conditioning and water maze learning. To this end p25 expression was induced in 11-month old CK-p25 mice for 6 weeks, before one group was injected daily for 4 weeks with SB whereas the control group received saline injection (FIG. 4a). Compared to the vehicle group, SB treated CK-p25 Tg mice showed significantly enhanced associative (freezing behavior) when compared to saline (vehicle) injected CK-p25 Tg mice (P=0.009) (FIG. 4b) and spatial learning, as shown by significantly shorter escape latency, when compared to the vehicle group ($F_{1,538}$=87.484; P<0.0001) (FIG. 4c), and increased levels of synaptic marker proteins (FIG. 4d, e; FIG. 7f, h). Also, SB and vehicle-injected CK-p25 Tg mice displayed a similar extent of brain atrophy and hippocampal neuronal loss (FIG. 7e). These findings show that increased histone acetylation using the HDAC inhibitor SB can reinstate learning ability in mice exhibiting severe neurodegeneration.

Figure 4F:
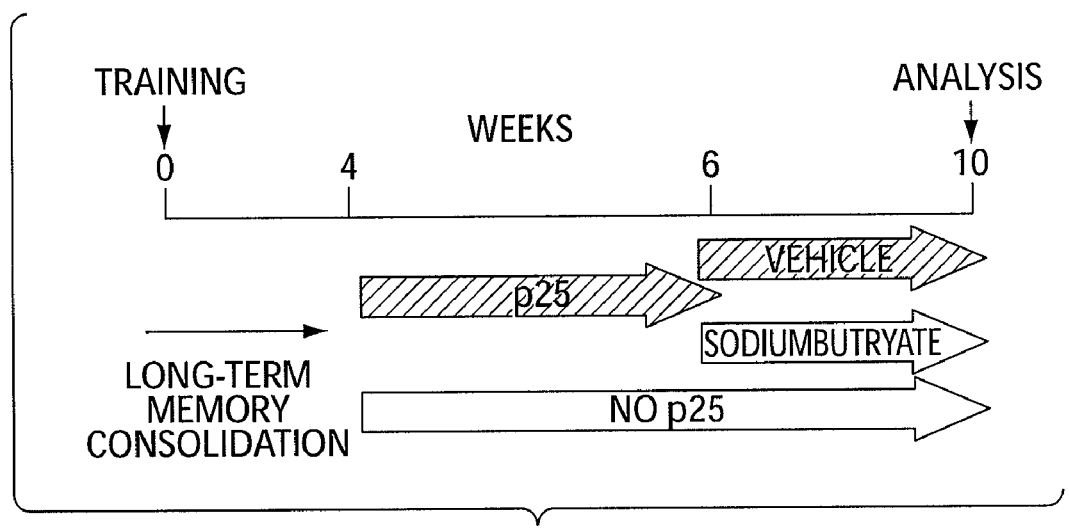
Figure 4G:
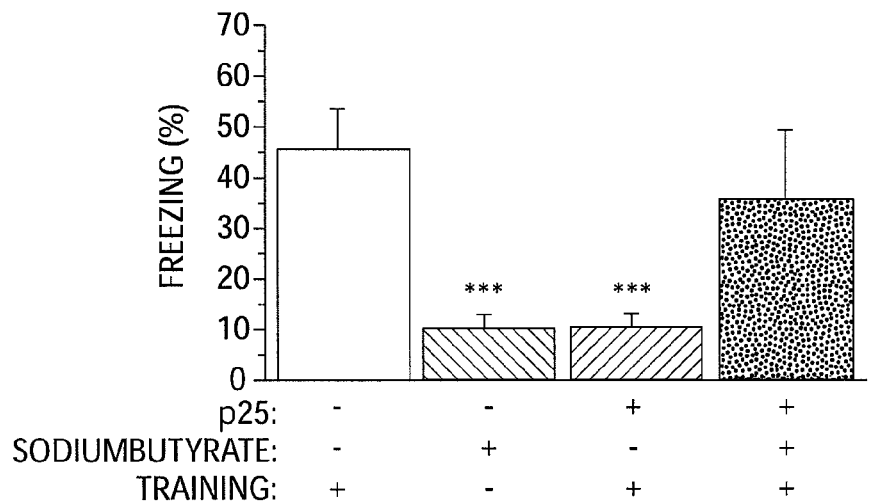
Figure 4H:
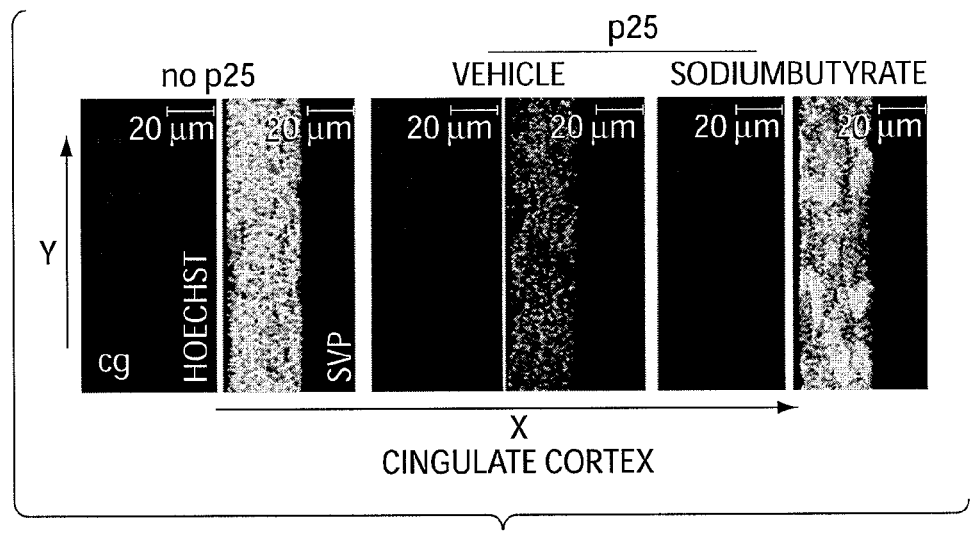
Figure 4I:
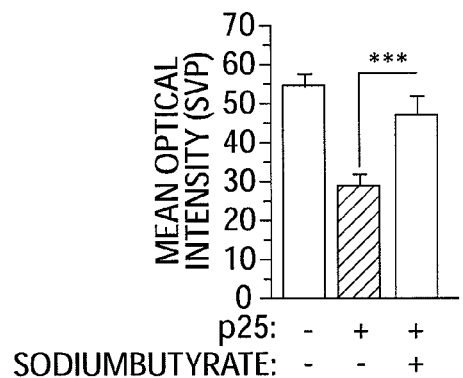
Figure 7G:
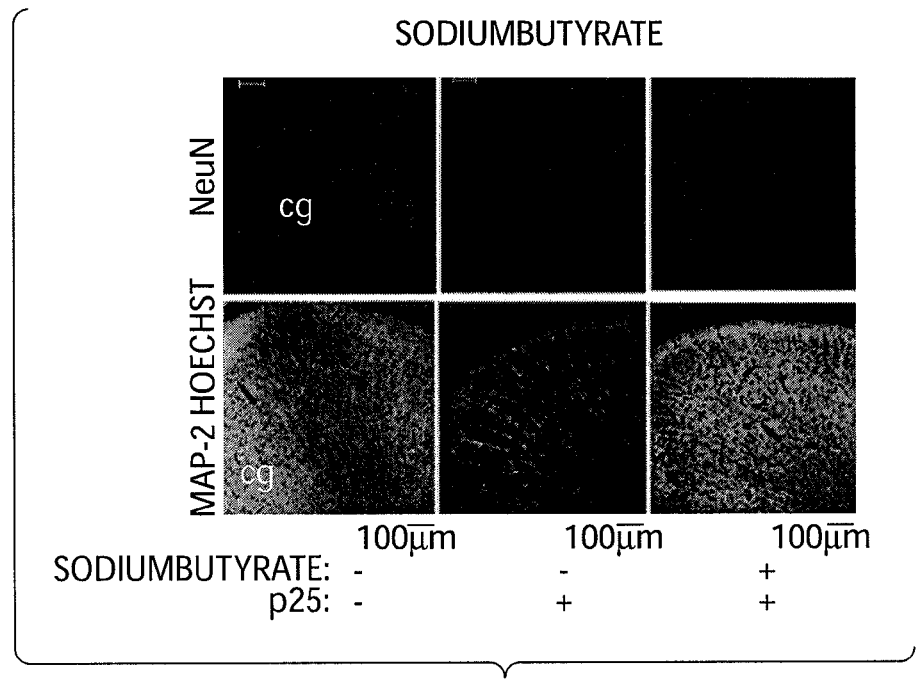

The effect of HDAC inhibition on the recovery of inaccessible long-term memories was evaluated. Eleven month old CK-p25 Tg mice were trained in the fear conditioning paradigm and returned to their home cages for 4 weeks. Subsequently p25 was induced for 6 weeks before the mice were injected with either saline (vehicle, n=12) or SB (1.2 g/kg, n=14) for 4 weeks (daily). Afterwards all mice, including a vehicle injected control groups that did not express p25 (n=15) and a group of SB-injected control mice that were not trained (n=8), were subjected the memory test. (FIG. 4f). Vehicle injected CK-p25 Tg mice showed impaired access to long-term memory as revealed by the markedly reduced freezing behavior compared to the control mice that did not express p25. When compared to the trained control group, saline-injected CK-p25 Tg mice showed a significant reduction in freezing behavior during the memory test (P<0.0001) test, suggesting the loss of consolidated long-term memories. SB-injected CK-p25 Tg mice performed significantly better than vehicle injected CK-p25 Tg mice (P=0.0496)(FIG. 4g). Despite a similar degree of brain atrophy and neuronal loss (FIG. 7g), SB-injected CK-p25 Tg mice showed significantly increased freezing and elevated levels of synaptic marker proteins when compared to the vehicle CK-p25 Tg group (FIG. 4g-i; FIG. 7g, h). Similarly, SB administration also leads to the recovery of long-term spatial memories (FIGS. 9a, d). Thus chronic injection of SB led to the recovery of memories in CK-p25 Tg mice that had developed severe neuronal loss.

Example 5

Figure 5A:
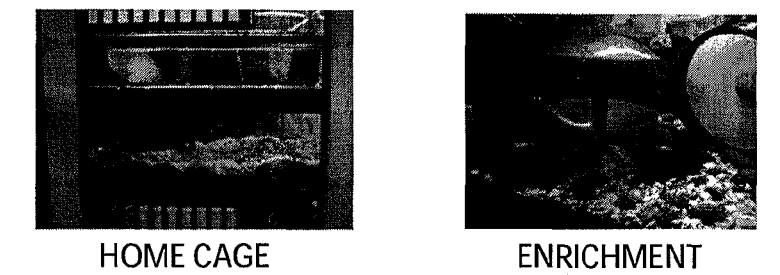
FIG. 5 shows that enrichment facilitates learning. a. Images showing a home cage and a cage used for environmental enrichment (EE). b. EE and freezing behavior. c. EE and the Morris water maze paradigm.
Figure 5B:
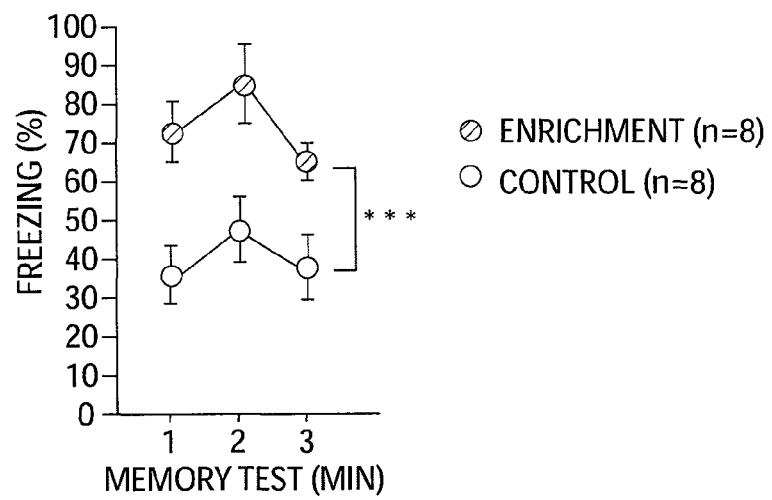
Figure 5C:
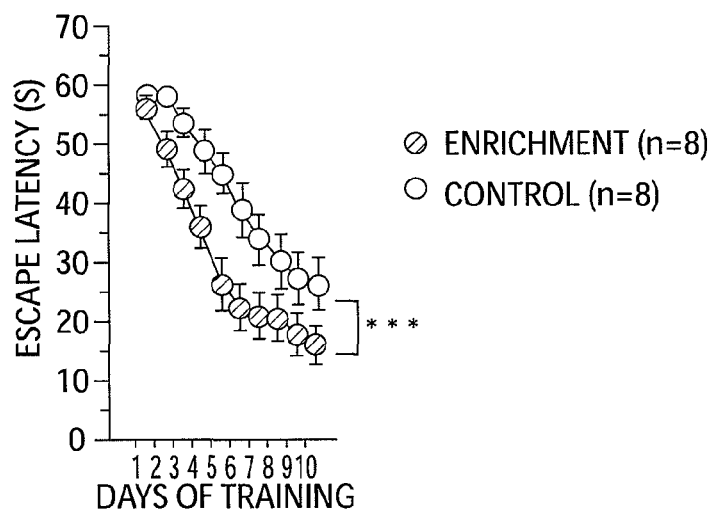

Exposure to EE facilitates learning ability in WT mice. Exposure of WT mice to EE facilitated their learning ability and caused elevated levels of marker proteins for synaptic integrity and plasticity indicating dendritic branching and synaptogenesis (6). Images showing a home cage and a cage used for environmental enrichment (EE) are depicted in FIG. 5A. For EE stimulus up to 4 mice were constantly housed in a large cage that contained various toys and running wheels (1 wheel/2 mice). All toys were changes on daily basis. C57BL6J mice (n=8/group) were subjected to EE for 2 weeks and trained in the fear conditioning paradigm. Enriched mice showed significantly more freezing behavior during the memory test performed 24 h later, when compared to the home cage group (P<0.0001), indicating facilitated associative learning (FIG. 5b). Similar results were obtained in the Morris water maze paradigm (P<0.0001 control vs. enrichment) (FIG. 5b).

Figure 6A:
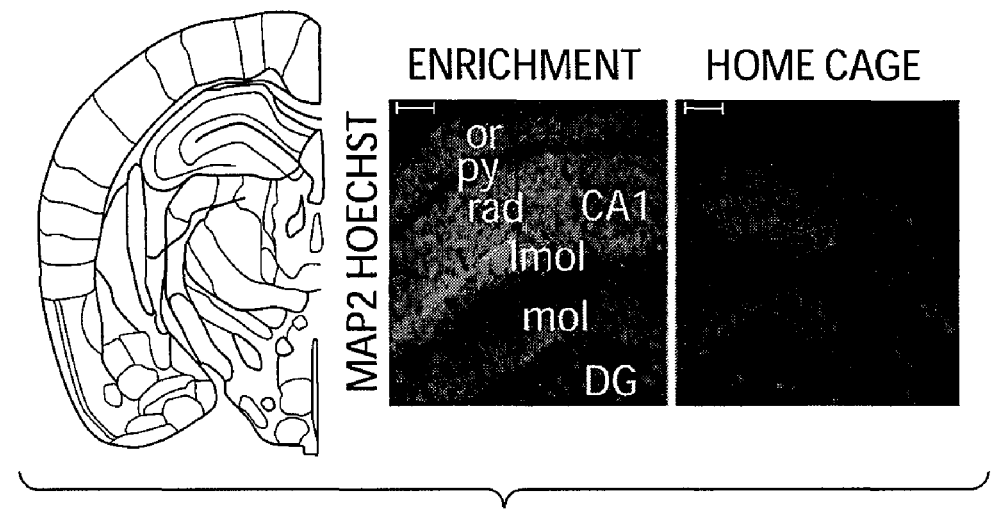
FIG. 6 shows that enrichment facilitates synaptic plasticity. a. Representative images showing MAP-2 immunoreactivity (IR) in the hippocampus and anterior cingulate cortex (b) of enriched mice. c. Representative images of the hippocampal and anterior cingulate cortex (d) region of enriched and non-enriched mice showing staining of the synaptic marker protein synaptophysin (SVP). e. Representative immunoblots from the hippocampus and cortex of enriched and non-enriched mice. **P<0.001. py, pyramidal cell layer; oriens; rad, stratum radiatum; Lmol, molecular layer; mol, lower molecular layer; GrDG, granula cell layer of the dentate gyrus, DG, dentate gyrus; CA1, hippocampal regions CA1; cg, cingulate cortex.
Figure 6B:
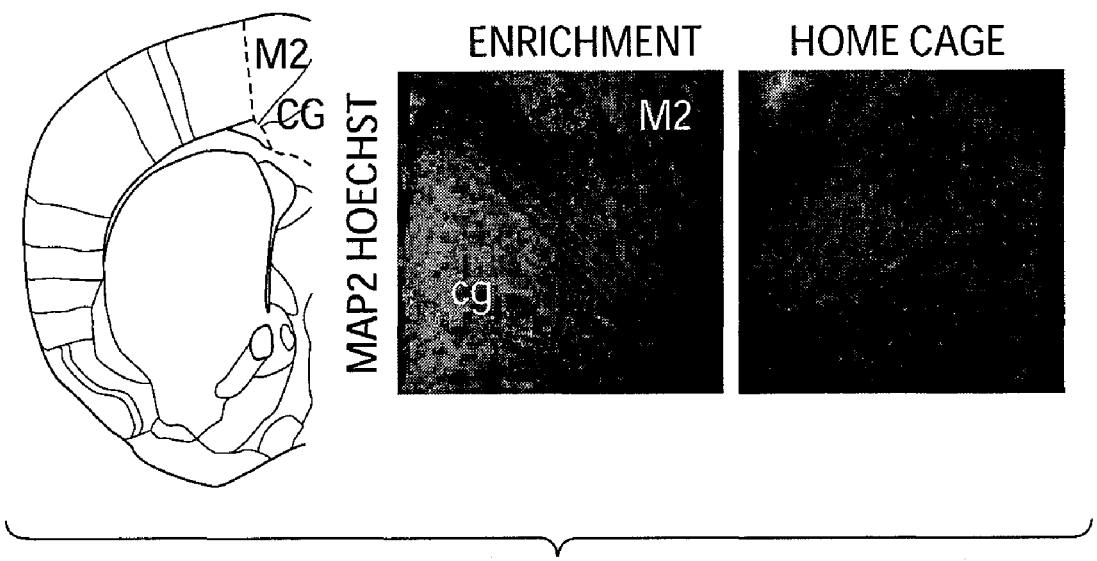
Figure 6C:
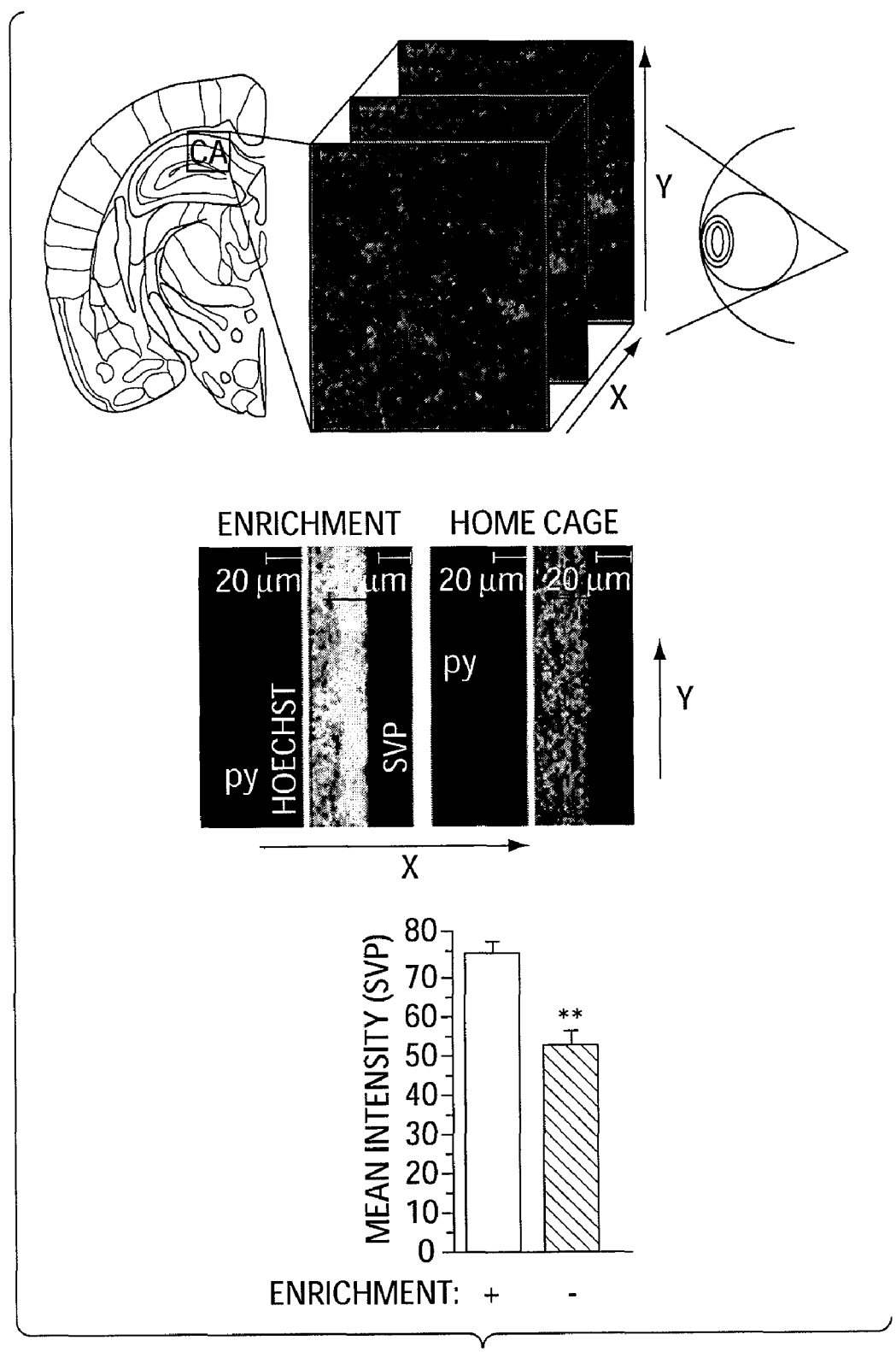
Figure 6D:
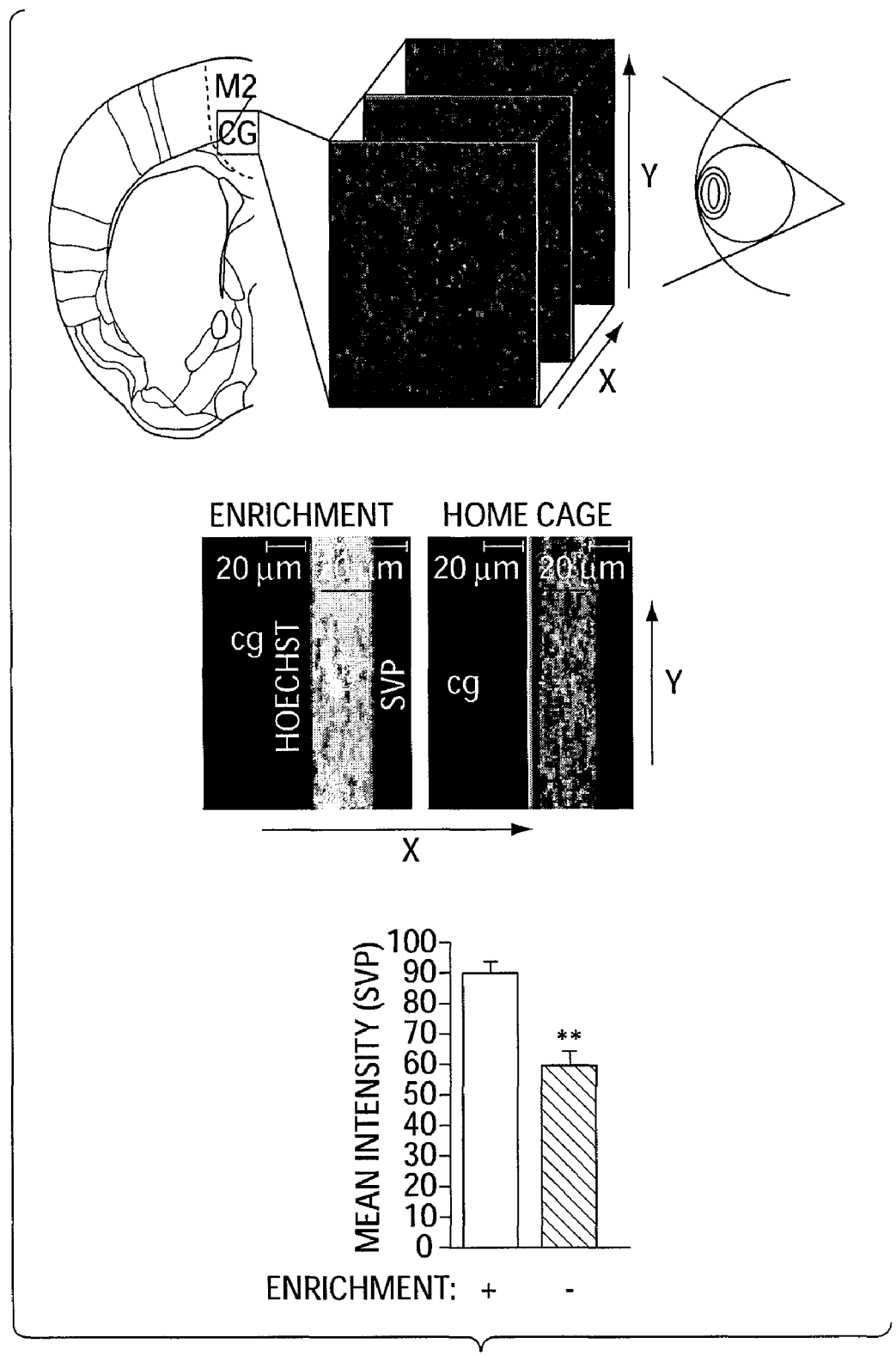
Figure 6E:
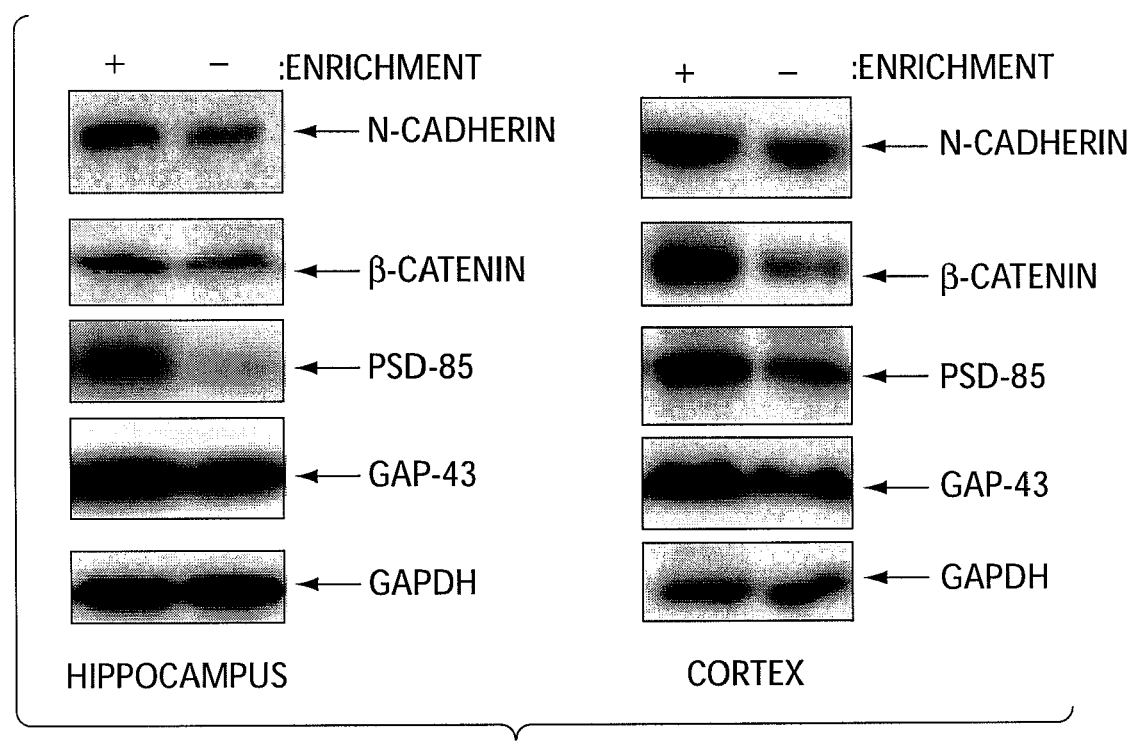

To investigate the relationship between EE and synaptic plasticity, C57BL6J mice (n=3/group) were subjected to EE for 2 weeks and subsequently used for analysis. Representative images showing increased MAP-2 immunoreactivity (IR) in the hippocampus and anterior cingulate cortex of enriched mice are shown in FIG. 6a and FIG. 6b. Representative images of the hippocampal and anterior cingulate cortex region of enriched and non-enriched mice showing staining of the synaptic marker protein synaptophysin (SVP) are shown in FIG. 6c and FIG. 6d. Confocal images (1 μm) were scanned and subjected to three-dimensional reconstruction. Pictures are displayed as seen from the x-axis. LSMeta10 software was used to calculate the mean SVP intensity. Brain sections with the strongest intensity were scanned first. All other images included in the analysis where scanned using the same microscope setting. Enriched mice displayed significantly increased hippocampal SVP (IR) when compared to non-enriched mice. Representative immunoblots from the hippocampus and cortex of enriched and non-enriched mice show that several markers for synaptic plasticity and integrity were increased in enriched mice when compared to non-enriched mice, indicating facilitated synaptic plasticity (P<0.0001)(FIG. 6e). **P<0.001. py, pyramidal cell layer; oriens; rad, stratum radiatum; Lmol, molecular layer; mol, lower molecular layer; GrDG, granula cell layer of the dentate gyrus, DG, dentate gyrus; CA1, hippocampal regions CA1; cg, cingulate cortex.

Example 6

Effects of enrichment or sodiumbutyrate treatment on plasticity factors in CK-p25 Tg mice that developed severe neurodegeneration. For EE treatment p25 was induced in 11 month old CK-p25 Tg mice for 6 weeks. Afterwards p25 expression was repressed as described in (3) and one group of CK-p25 Tg mice was subjected to EE. Representative pictures showing immunostaining for NeuN in the hippocampal region confirm similar degree of hippocampal neuronal loss in enriched and non-enriched CK-p25 Tg mice are shown in FIG. 7a. Brain sections from the same mice used in the experiment described under of FIG. 7a were immunostained for the dendritic marker protein MAP-2. MAP-2 immunoreactivity of enriched CK-p25 Tg mice increased when compared to the non-enriched group (FIG. 7b). Similar results were observed in other brain regions such as the anterior cingulated cortex (FIG. 7c). Representative immunoblots from cortical lysates of control mice, enriched and non-enriched CK-p25 Tg mice are shown in FIG. 7d. Although NeuN levels were decreased to similar levels in enriched and non-enriched CK-p25 Tg mice, several markers for synaptic plasticity and integrity were increased in enriched when compared to non-enriched CK-p25 Tg mice. *P<0.05 vs. non enriched group, n=3.

Figure 7H:
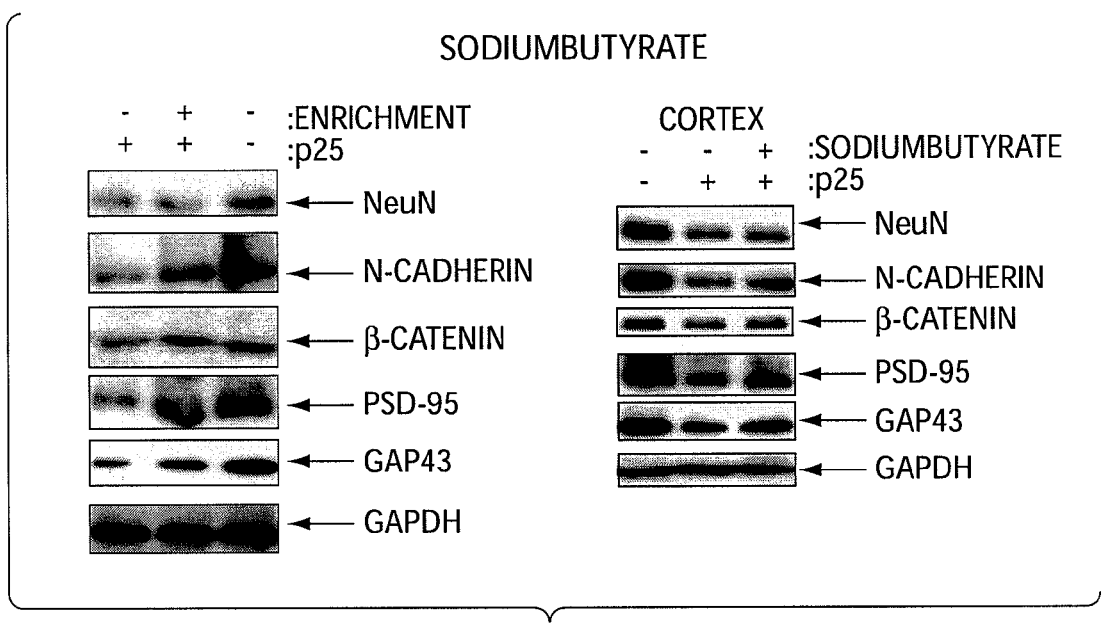

For SB treatment, p25 was induced in 11 month old CK-p25 Tg mice for 6 weeks. Afterwards p25 expression was repressed and one group of CK-p25 Tg mice was subjected to daily sodiumbutyrate (SB) injection (1.2 g/kg) for 4 weeks, whereas the other group received saline injection. Representative images showing hippocampal NeuN staining confirming that SB and vehicle injected CK-p25 mice displayed hippocampal neuronal loss to the same degree are shown in FIG. 7e. Representative images showing hippocampal MAP-2 staining are depicted in FIG. 7f. MAP-2 immunoreactivity of CK-p25 Tg mice treated with SB is increased when compared to the vehicle group. Representative images showing NeuN staining of the ACC. While SB and vehicle-injected CK-p25 Tg mice displayed similar levels of neuronal loss in the ACC (light spots, NeuN staining) MAP-IR was increased in SB treated when compared to vehicle treated CK-p25 Tg mice are shown in FIG. 7g. Representative immunoblots from the hippocampus and cortex of all groups are shown in FIG. 7h. Although NeuN levels were decreased to similar levels in SB and vehicle injected CK-p25 Tg mice, several markers for synaptic plasticity and integrity were increased in SB-injected when compared to vehicle injected CK-p25 Tg mice. *P<0.05 vs. vehicle group, n=3. py, pyramidal cell layer; rad, stratum radiatum; Lmol, molecular layer; mol, lower molecular layer; GrDG, granula cell layer of the dentate gyrus, DG, dentate gyrus; CA1, hippocampal regions CA1; cg, cingulate cortex.

Example 7

The effect of sodiumbutyrate injection on learning, basal anxiety, explorative behavior and brain plasticity. C57BL/6J mice were subjected to fear conditioning and injected intraperitoneally [ip] with 1.2 g/kg sodiumbutyrate (SB, n=8) or saline (vehicle; n=8) immediately afterwards. SB injected mice displayed significantly more freezing behavior during the memory test performed 24 h later (P<0.0001) (FIG. 8b). C57BL/6J mice were implanted with microcannulae into the lateral brain ventricles (icv) and injected with either 100 ng SB, 50 ng TSA or vehicle immediately after fear conditioning (n=8/group). SB or TSA injected mice displayed more freezing behavior than vehicle injected mice during the memory test performed 24 h later (P<0.0001) (FIG. 8b). C57BL/6J were daily injected [ip] with SB or saline (n=8/group) for 4 weeks before all mice were subjected to the elevated plus maze and open field test. No significant group difference was observed indicating that SB-treatment did not affect basal anxiety or explorative behavior (FIG. 8c). FIG. 8d shows representative images showing increased MAP-2 immunoreactivity (IR) in the hippocampus of wild type mice injected with SB for 4 weeks, when compared to vehicle injected mice. FIG. 8e shows representative immunoblots (n=3/group) from hippocampal lysates of wild type mice injected with SB or vehicle for 4 weeks. Immunoblots were quantified relative to the optical density of the vehicle-group (set to 1). Several markers for brain plasticity were increased in SB injected mice. FIG. 8f shows representative images with increased SVP IR in the hippocampus of mice injected with SB for 4 weeks, when compared to vehicle injected mice (P=0.0243). The analysis was performed as described under FIG. 1g.

Example 8

Figure 9B:
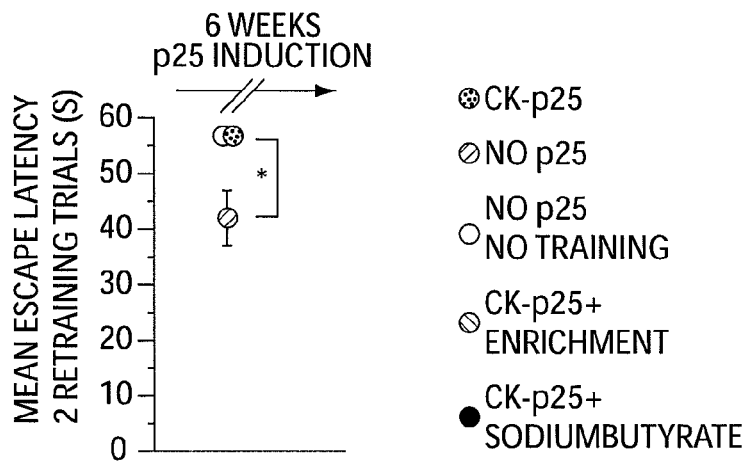
Figure 9C:
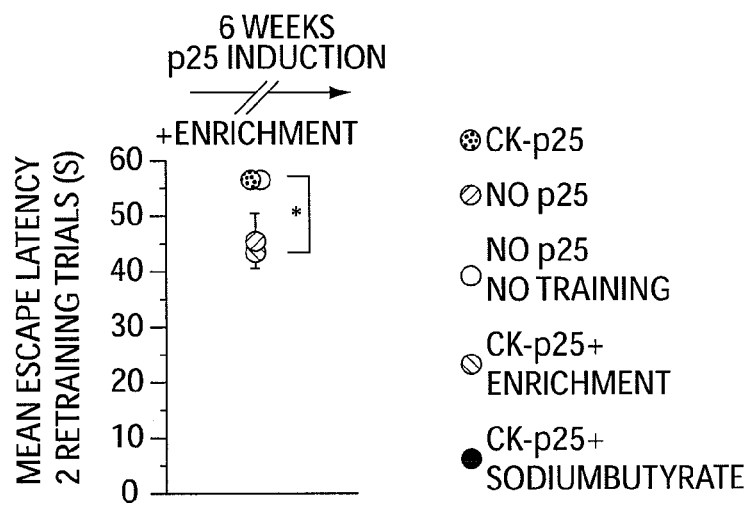
Figure 9D:
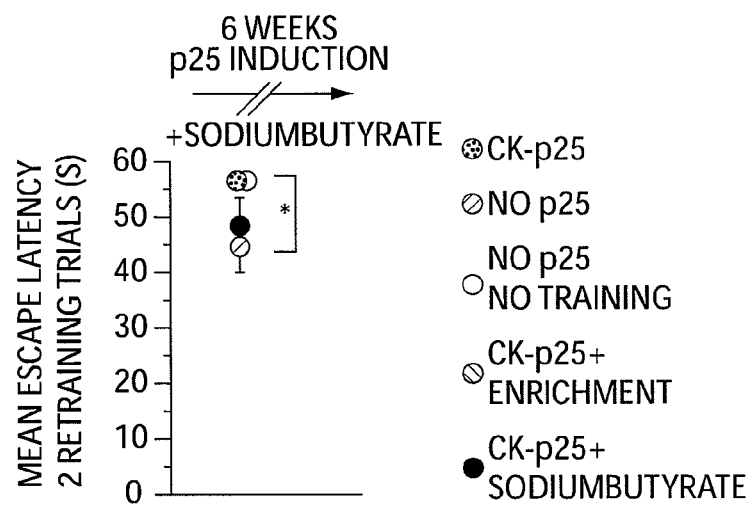

Recovery of spatial memories upon environmental enrichment and sodiumbutyrate injection. CK-p25 Tg mice in which p25 expression was repressed and control mice were trained in the water maze paradigm until all mice reliably found the hidden platform. Afterwards all mice were returned to their home cages for 4 weeks to allow the consolidation of hippocampus independent long-term memories. Afterwards p25 expression was induced for 6 weeks, followed by p25 repression. Pilot studies showed that a probe test, commonly used to analyze memory retrieval in the water maze paradigm, was not a reliable read out to analyze long-term memory retrieval. In fact, without extensive re-training even wild type mice showed no significant preference for the target quadrant when tested 10 weeks after the training in a probe test (data not shown). To measure the retrieval of long-term memory mice were instead exposed to only 2 reminder-training sessions on a single day. The mean escape latency during the reminder-training sessions was compared to control mice that did not receive the initial training. Using this approach control mice that did not receive the initial training (n=7) and showed a significantly longer escape latency than trained control mice, suggesting that this difference reflects spatial long-term memory in trained control mice. Notably, 6-week induced trained CK-p25 Tg mice (n=8) showed significantly longer escape latency than trained control mice (n=8) during the reminder-training session. These data indicate that 6 weeks of p25 expression causes loss of spatial memory (FIG. 9b). The recovery of spatial memories upon environmental enrichment was evaluated by a similar experiment, except that after 6 weeks of p25 expression mice were either subjected to EE or returned to their home cages for 4 weeks. When the memory test was performed as described above non-enriched CK-p25 Tg mice (n=8) showed significantly reduced escape latency when compared to the trained control group (n=8). However, the escape latency of enriched CK-p25 Tg mice was significantly shorter when compared to non-enriched CK-p25 Tg mice. Enriched control mice that did not receive the initial training served as a control to delineate learning from long-term memory retrieval. These data provide evidence that spatial long-term memories can recover upon EE (FIG. 9c). To evaluate the recovery of spatial memories upon SB injection, a similar experiment was performed as described above, but instead of EE, one group of CK-p25 Tg mice (n=10) received daily injection of SB, whereas the other group was injected with vehicle (n=10). Similar to the data described above, the results provide evidence that spatial long-term memories recover after neuronal loss upon injection of SB. *P<0.001 vs. CK-p25 vehicle or "no p25 no training" groups (FIG. 9d).

Example 9

Figure 10A:
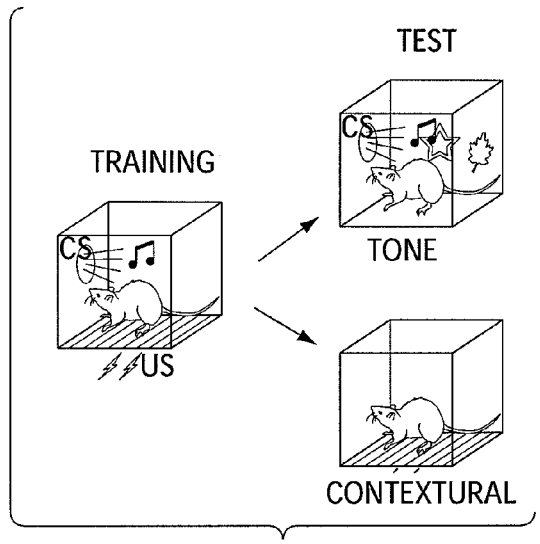
FIG. 10 shows that the over expression of HDAC2, but not that of HDAC1, impairs fear conditioning without affecting sensory-motor functions. a. Experimental design. b. Freezing behavior during the during the context- and tone-dependent memory test. c. Distance traveled during the initial 3 min exposure to the training box. d. Average activity during the training and the increased activity during electoral stimulation.
Figure 10B:
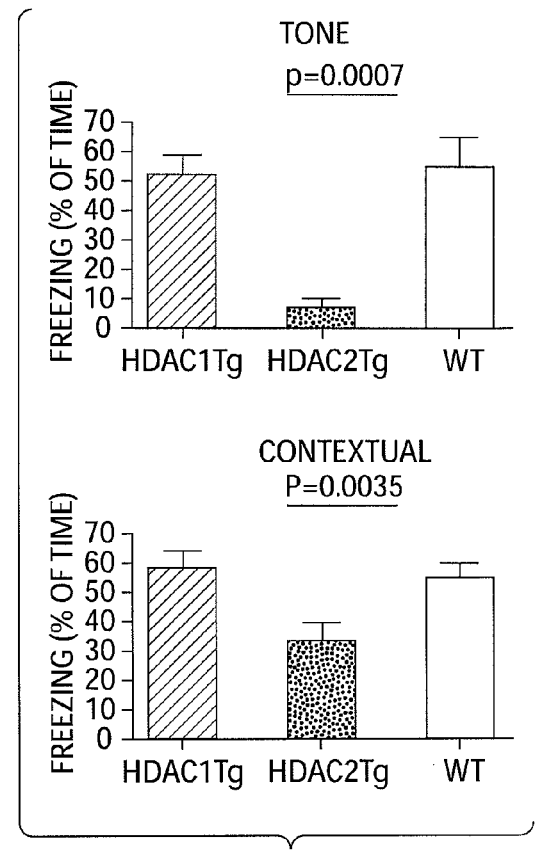
Figure 10C:
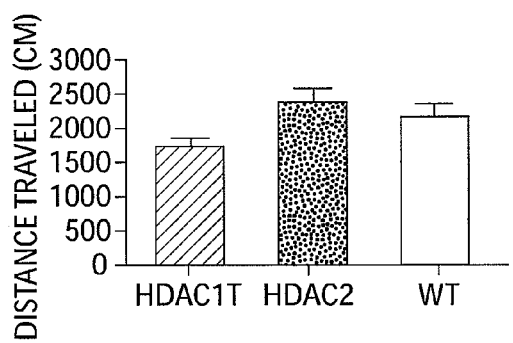
Figure 10D:
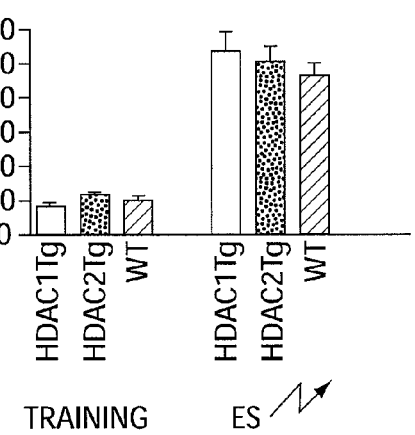

The over expression of HDAC2, but not HDAC1, impairs fear conditioning without affecting sensory-motor functions. A fear conditioning experiment is depicted in FIG. 10a was performed as previously described (24). Mice were trained in chamber for 3 minutes, following by a 30-second tone cue immediately before a 0.8 mA electoral stimulation. Mice were represented in the same chamber without tone cue after 24 hrs and the time freezing behavior appeared was recorded. Tone-induced freezing was recorded in another chamber with different decoration 24 hrs later. The freezing behavior was monitored during the context- and tone-dependent memory test of HDAC 1 transgenic mice (Tg), HDAC2 transgenic mice, and control mice (FIG. 10b; HDAC1 Tg n=17; HDA 2 Tg n=14; control, n=19). HDAC2 Tg mice showed impaired fear conditioning. During the initial 3 min exposure to the training box, no significant difference between distances traveled could be detected between HDAC1 Tg, HDAC2 Tg, and control mice (FIG. 10c). Average activity during the training procedure, and an increased activity during electoral stimulation, reflected an escape response to the electric foot shock that was applied during the training procedure. No difference could be detected between HDAC 1 Tg, HDAC2 Tg, and control mice (FIG. 10d).

Example 10

Figure 11A:
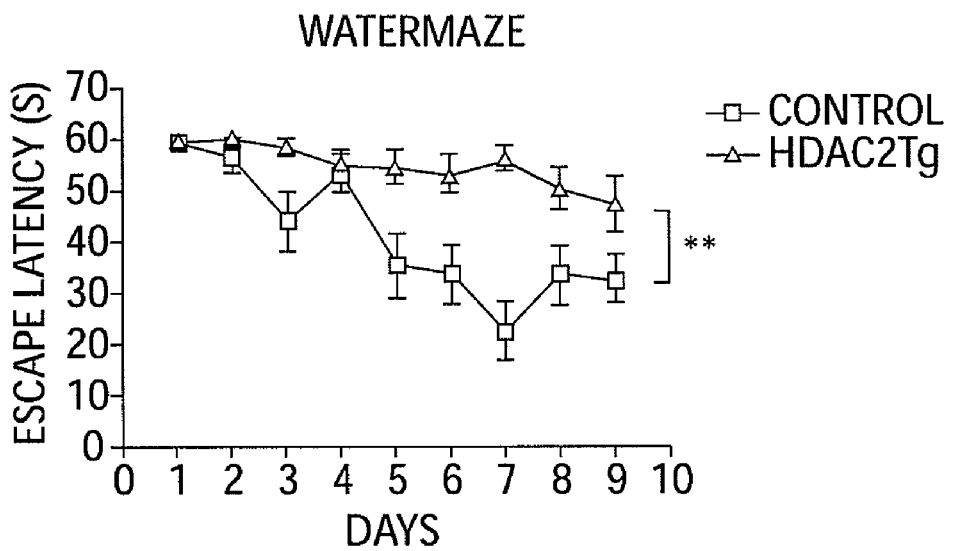
FIG. 11 shows that the over expression of HDAC2 impairs spatial learning. a. Escape latencies of control mice that were subjected to the water maze paradigm for nine consecutive days, with 2 trials everyday. b. The probe test, performed after 5 days of training trials.
Figure 11B:
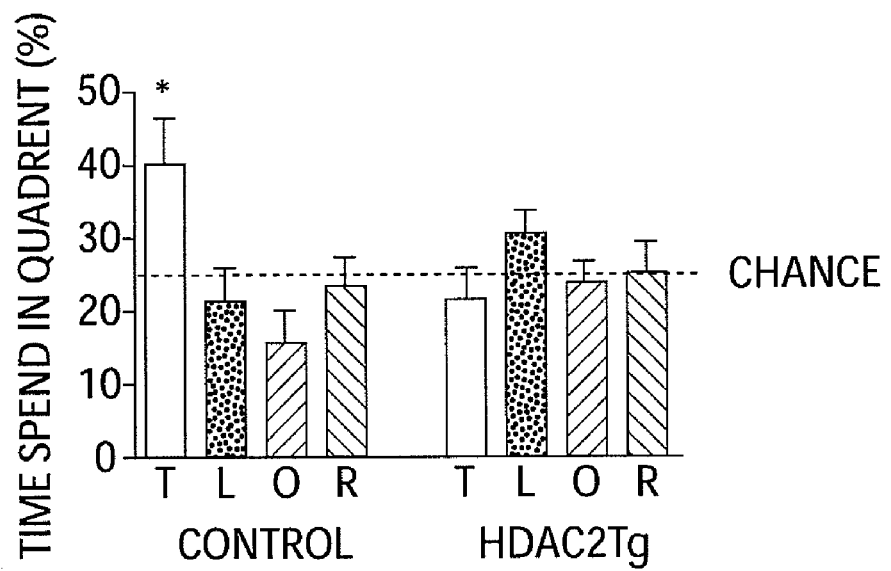

The over expression of HDAC2 impairs spatial learning. The water maze paradigm (Morris, R. G. M., Garrud, P., Rawlins, J. N. P., O'Keefe, J. 1982. Place navigation impaired in rats with hippocampal lesions. Nature, 297, 681-683) was performed in a circular tank (diameter 2 m) filled with opaque water. A platform (11×11 cm) was submerged below the water's surface in the center of the target quadrant. The swimming path of the mice was recorded by a video camera and analyzed by the Videomot 2 software (TSE). For each training session, the mice were placed into the maze subsequently from four random points of the tank. Mice were allowed to search for the platform for 60 seconds. If the mice did not find the platform within 60 seconds, they were gently guided to it. Mice were allowed to remain on the platform for 15 seconds. During the memory test (probe test), the platform was removed from the tank, and the mice were allowed to swim in the maze for 60 s. HDAC2 transgenic mice (n=8) and control mice (n=8) were subjected to the water maze paradigm for nine consecutive days, with 2 trials everyday (FIG. 11a). The hidden platform was located in the target quadrant (T). Escape latencies of control mice improved significantly faster than control HDAC2 Tg mice throughout the training ($p=0.0044$). In the probe test, performed after 5 days of training trials, control mice ($p=0.0145$) spent significantly more time in the target quadrant (T) than HDAC2 Tg mice (FIG. 11b).

Example 11

Figure 12A:
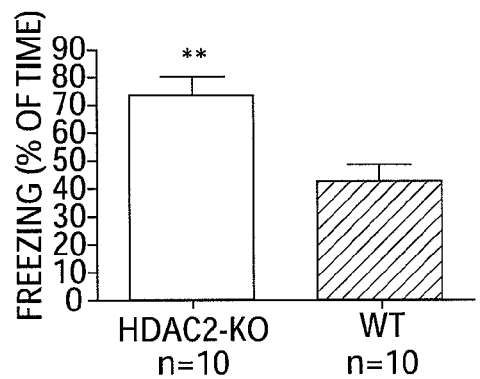
FIG. 12 shows that the HDAC2 gene knockout enhances associative learning. a. Freezing behavior of HDAC2 knockout (KO) mice and control mice during the contextual dependent memory test. b. Distance traveled during the initial 3 minutes exposure to the training box. c. The occurrence of average activity during training and increased activity during electoral stimulation.
Figure 12B:
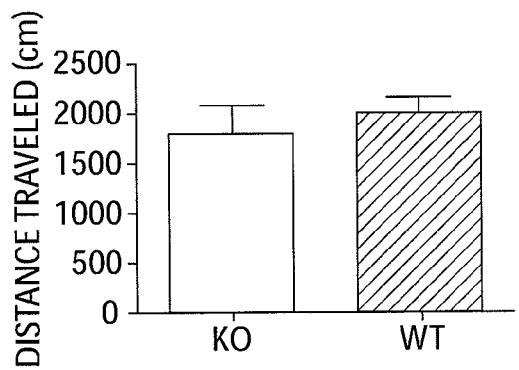
Figure 12C:
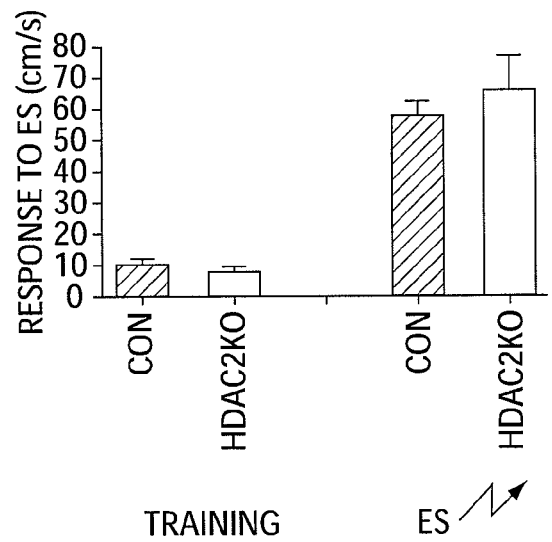

The HDAC 2 gene knockout enhances associative learning The freezing behavior of HDAC2 knockout (KO) mice and control mice (HDAC2 KO n=10; control, n=10) during the contextual dependent memory test is shown in FIG. 12a. HDAC2 KO mice showed enhanced fear conditioning. The distance traveled during the initial 3 minutes exposure to the training box (FIG. 12b). No significant difference could be detected between HDAC2 KO and control mice. Average activity during the training procedure and an increased activity during electoral stimulation reflected an escape response to the electric foot shock that was applied during the training procedure (FIG. 12c). No difference could be detected between HDAC2 KO and control mice.

Example 12

Figure 13A:
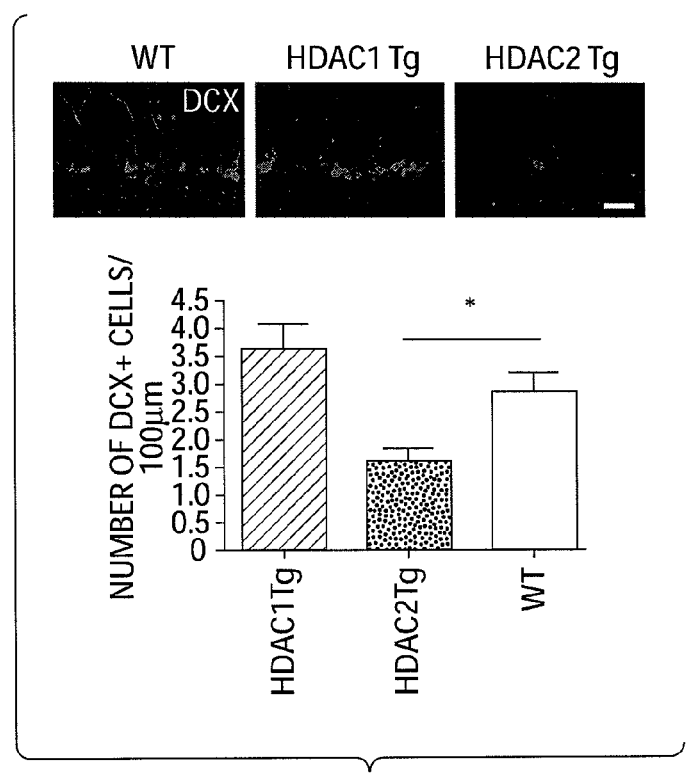
FIG. 13 shows that HDAC 2 over expression decreases newly generated neurons in dentate gyrus of adult mice. a. Representative images of hippocampal brain sections from two month-old-mice group (n=3/group) immunostained for the newborn neuron marker Doublecortin (DCX). b. Representative pictures show BrdU immunoreactivitiy (light regions) in the hippocampus dentate gyrus.
Figure 13B:
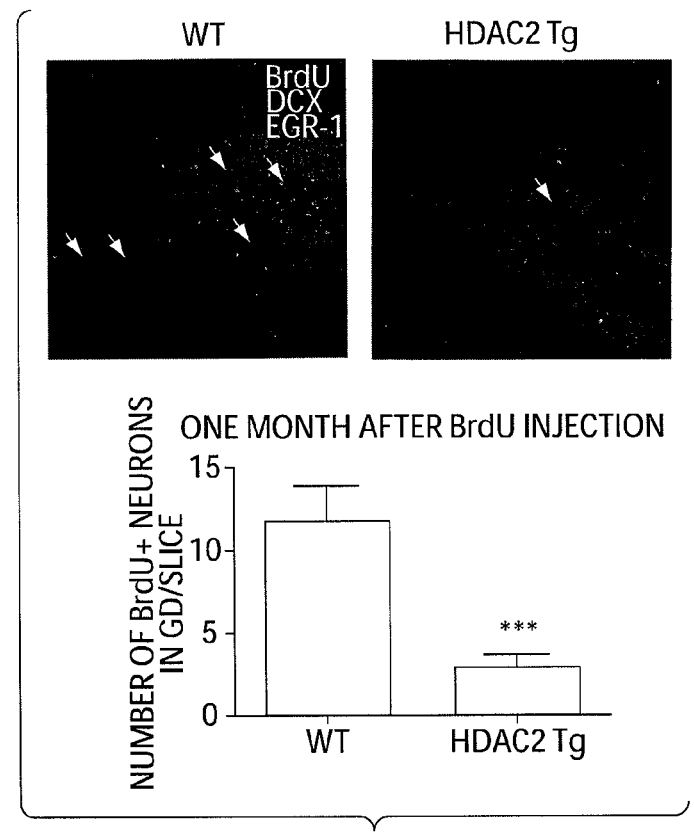

The over expression of HDAC 2 decreases newly generated neurons in dentate gyrus of adult mice. Representative images are shown of hippocampal brain sections from two month-old-mice group (n=3/group) immunostained for the newborn neuron marker Doublecortin (DCX). Representative pictures show DCX immunoreactivitiy (light regions) in the hippocampus dentate gyrus, scale bar, 40 um (FIG. 13a). Note the significant decrease in HDAC2 Tg group ($p=0.0193$). Representative pictures show BrdU immunoreactivitiy (light regions) in the hippocampus dentate gyrus (FIG. 13b). BrdU was i.p. injected into two-month-old mice groups (n=3) 30 days before analysis. Note the significant decrease in HDAC2 Tg group ($p=0.0001$).

Example 13

Figure 14A:
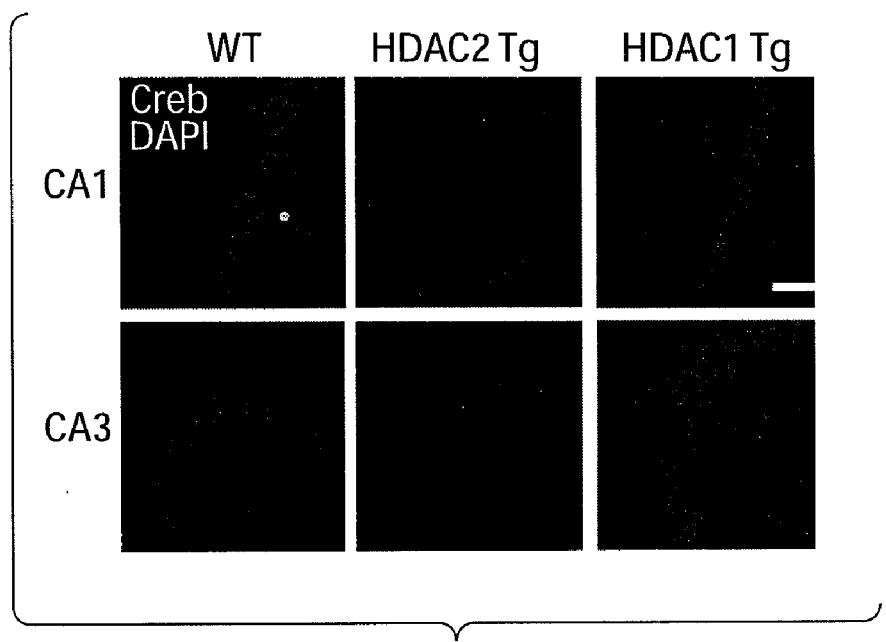
FIG. 14 HDAC 2 Tgs show reduced CREB expression in hippocampus. a. Representative images of hippocampal brain sections from two-month-old mice group immunostained for the CREB in CA1 and CA3 regions. b. Protein levels were analyzed in forebrain lysates of all experimental groups by immunoblotting.
Figure 14B:
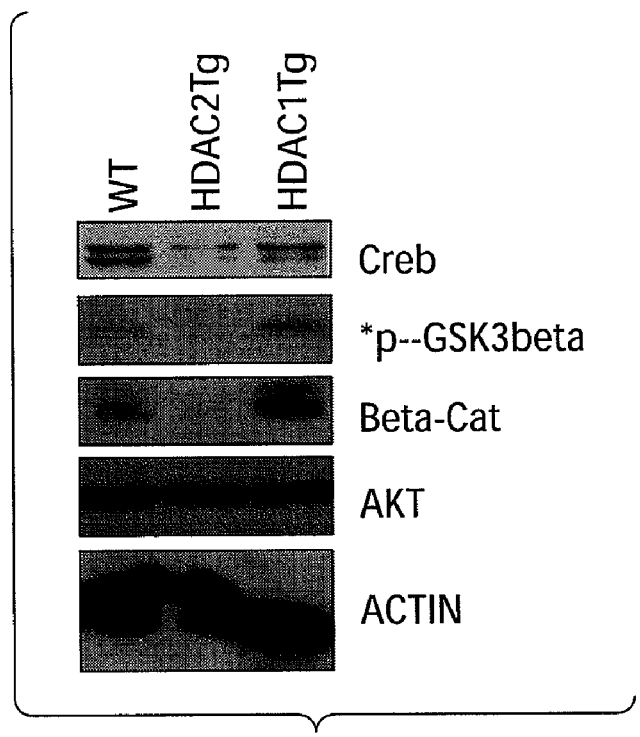

HDAC 2 Tgs show reduced CREB expression in hippocampus. Representative images of hippocampal brain sections from two-month-old mice group (n=3/group) immunostained for the CREB in CA1 and CA3 regions (FIG. 14a). Representative pictures show CREB immunoreactivitiy (light regions) in the hippocampus dentate gyrus, DAPI, blue, scale bar, 150 um. Protein levels are analyzed in forebrain lysates of all experimental groups (n=3/group) by immunoblotting (FIG. 14b).

Example 14

Figure 15:
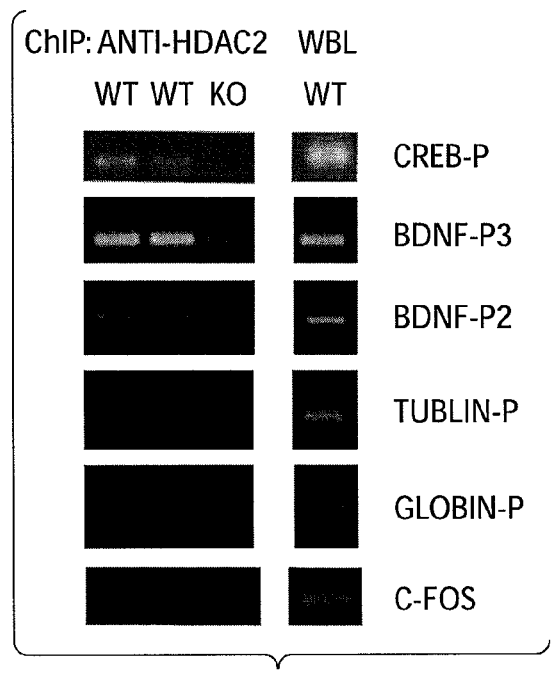
FIG. 15 shows that HDAC2 directly binds to the promoter region of specific genes and regulates gene expression. Whole brains from two-month-old experiment groups were fixed and homogenized. Lysates of all experimental groups are immune-precipitated with HDAC2 antibody and subjected to semi-quantities PCR analysis.

HDAC2 directly binds to the promoter region of specific genes and regulates gene expression. Whole brains from two-month-old experimental groups were fixed and homogenized. Lysates of all experimental groups were immune-precipitated with HDAC2 antibody and subjected to semi-quantitative PCR analysis (FIG. 15). DNA samples taken directly from lysates were prepared in 100 ng/ul (WBL). Equal volumes of ChIP samples from each group were used in PCR analysis. Primers were designed to target the promoter region of specific genes. Note that WT, but not the HDAC2 KO group, showed a strong signal in PCR amplification for the promoter region of CREB and BDNF, indicating that HDAC2 directly binds to those regions. Globin and Tubulin showed equal amounts of amplification in WT and LO group.

Example 15

Figure 16A:
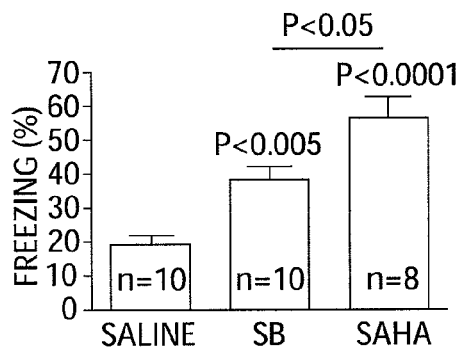
FIG. 16 shows that chronic treatment with SAHA or sodium butyrate, but not MS-275, facilitates contextual fear conditioning learning. a. After chronic treatment for 10-21 days, we found that SAHA is more potent than SB in facilitating associative learning using the contextual fear conditioning paradigm. b. Conversely, MS-275, a class 1 HDAC inhibitor, does not facilitate associative learning in mice. c. Brain lysates from SAHA and MS-275 treated mice exhibit increased acetylation of lys9lys 14 on histone 3 and lys5 on histone 4 compared to saline treated mice demonstrating that both drugs affect HDAC activity in the brain.
Figure 16B:
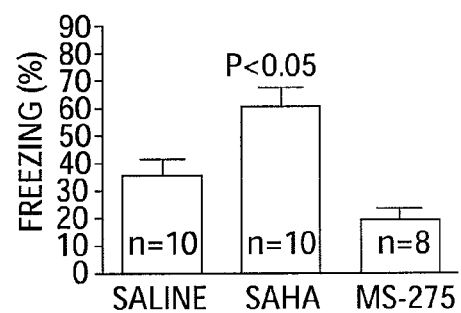
Figure 16C:
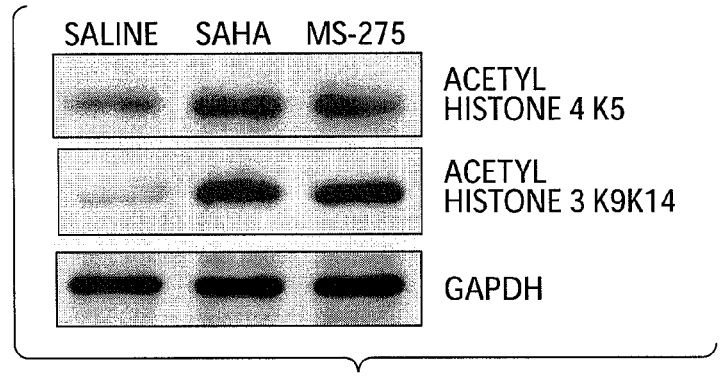

The effects of SAHA and MS-275, relative to sodium butyrate (SB), on the hippocampus dependent associative learning in wildtype mice. After chronic treatment for 10-21 days, we found that SAHA is more potent than SB in facilitating associative learning using the contextual fear conditioning paradigm (FIG. 16a). Conversely, MS-275, a class 1 HDAC inhibitor, does not facilitate associative learning in mice (FIG. 16b). Brain lysates from SAHA and MS-275 treated mice exhibit increased acetylation of lys9lys 14 on histone 3 and lys5 on histone 4 compared to saline treated mice (FIG. 16c) demonstrating that both drugs affect HDAC activity in the brain.

Example 16

Figure 17A:
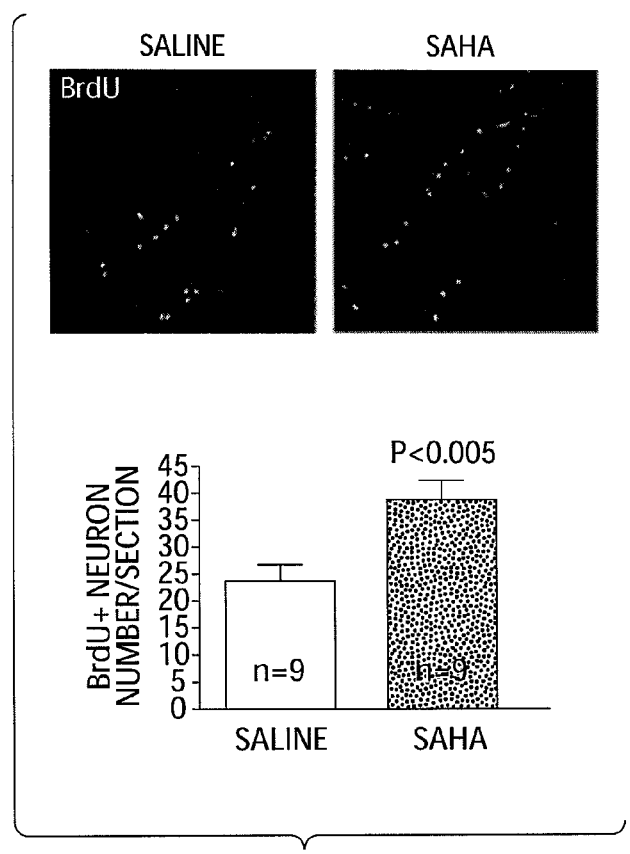
FIG. 17 shows that HDAC inhibitors regulate neuronal activity and neurogenesis in dentate gyrus. a. In agreement with its beneficial effect on associative learning, SAHA treatment increased BrdU positive cells in the subgranule zone of the dentate gyrus. b. In addition, DCX, a marker for newly generated neurons, labeled more cells in SAHA treated but not MS-275 treated dentate gyrus. These observations suggest that SAHA upregulates adult neurogenesis in the dentate gyrus. c. Furthermore, SAHA treated mice showed higher number of c-fos positive cells after fear conditioning training but MS-275 treated mice showed lower number of c-fos positive cells compared to saline treated group. d. Data is presented in bar graph format demonstrating significant enhancement by SAHA. Thus, activity induced c-fos expression may also be used to evaluate the effect of HDAC inhibitors on hippocampus dependent learning.
Figure 17B:
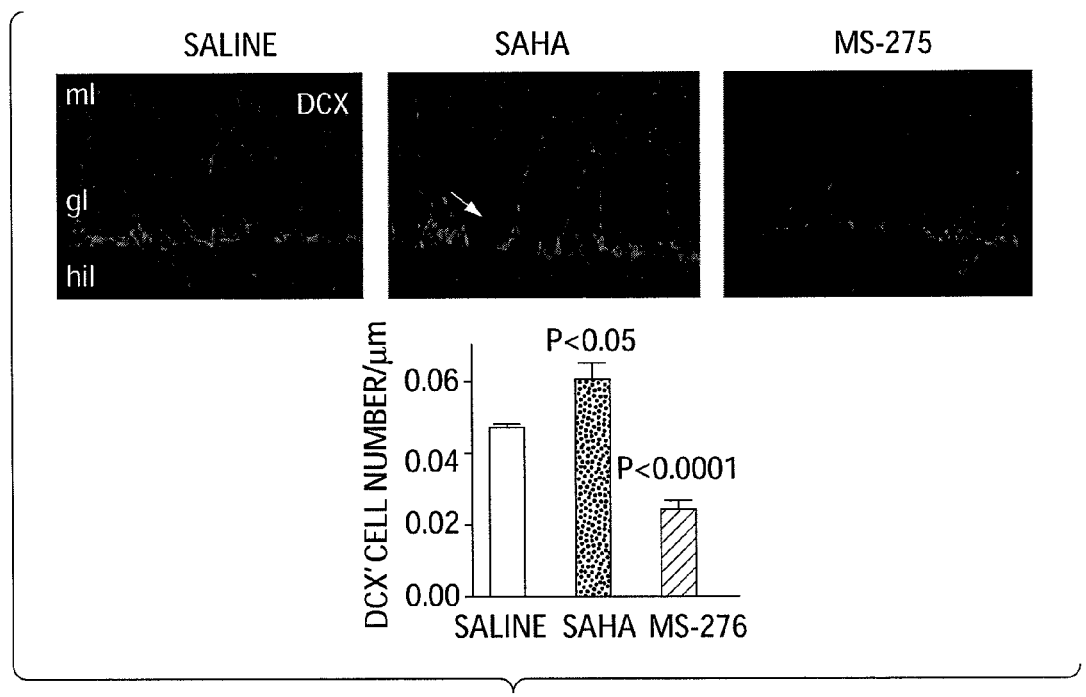
Figure 17C:
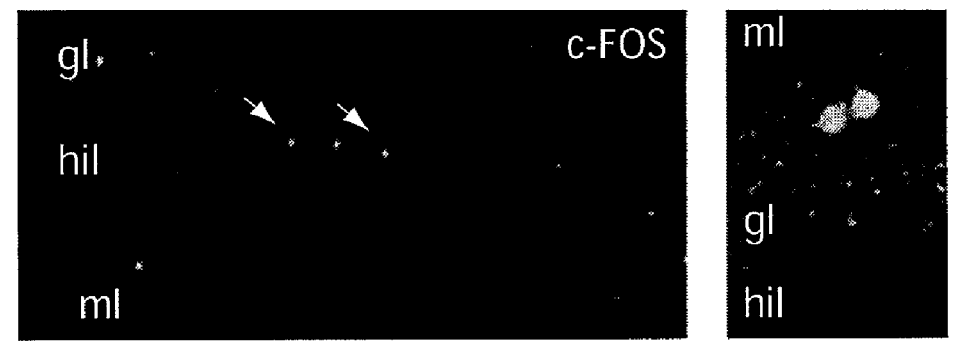
Figure 17D:
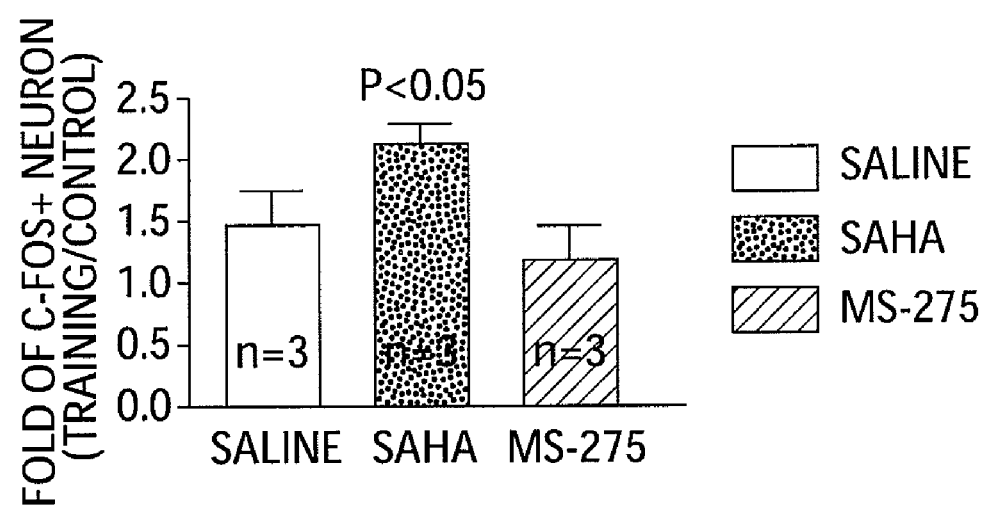

HDAC inhibitors regulate neuronal activity and neurogenesis in dentate gyrus. In agreement with its beneficial effect on associative learning, SAHA treatment increased BrdU positive cells in the subgranule zone of the dentate gyrus (FIG. 17a). In addition, DCX, a marker for newly generated neurons, labeled more cells in SAHA treated but not MS-275 treated dentate gyrus (FIG. 17b). These observations suggest that SAHA upregulates adult neurogenesis in the dentate gyrus. Furthermore, SAHA treated mice showed higher number of c-fos positive cells after fear conditioning training but MS-275 treated mice showed lower number of c-fos positive cells compared to saline treated group (FIG. 17c). Thus, activity induced c-fos expression may also be used to evaluate the effect of HDAC inhibitors on hippocampus dependent learning. FIG. 17d is a bar graph depicting the significant enhancement by SAHA.

Example 17

Figure 18A:
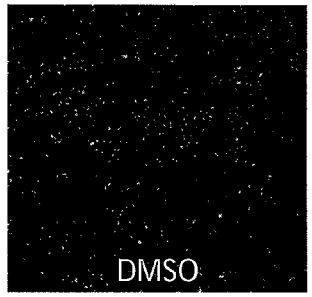
FIG. 18 are data from cell-based and biochemical assays for optimizing HDAC inhibitor potency and selectivity. Images of (a) untreated (DMSO) and (b) trichostatin A-treated rat neural progenitor cells cultured in a 384-well plate after staining with antibodies for acetylated histones (light regions). c. Comparison of the histone modification signatures of two HDAC inhibitors, trichostatin (bars on the left) and valproate (bars on the right) using a human neuroblastoma cell line and a panel of antibodies toward different histone modifications. d. Example of an in vitro deacetylase assay for HDAC inhibitor screening using recombinant, full-length, human HDAC5 (0.5 μg). HDAC5 deacetylase activity (AFU; change in arbitrary fluorescence units/min) as a function of substrate concentration. e. IC50 values (nM) of SAHA, trichostatin A and the non-hydroxamate apicidin against human HDAC3 (class I) and HDAC5 (class II). Structures of potential novel class II-selective biasing elements for HDAC inhibitor design. g. HDAC inhibition of a representative benzohydrazide (BCB-001) and triazole carboxylate (BCB-002) as measured using recombinant HDAC2 (class I) and HDAC10 (class II).
Figure 18B:
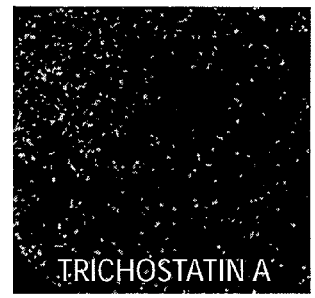
Figure 18C:
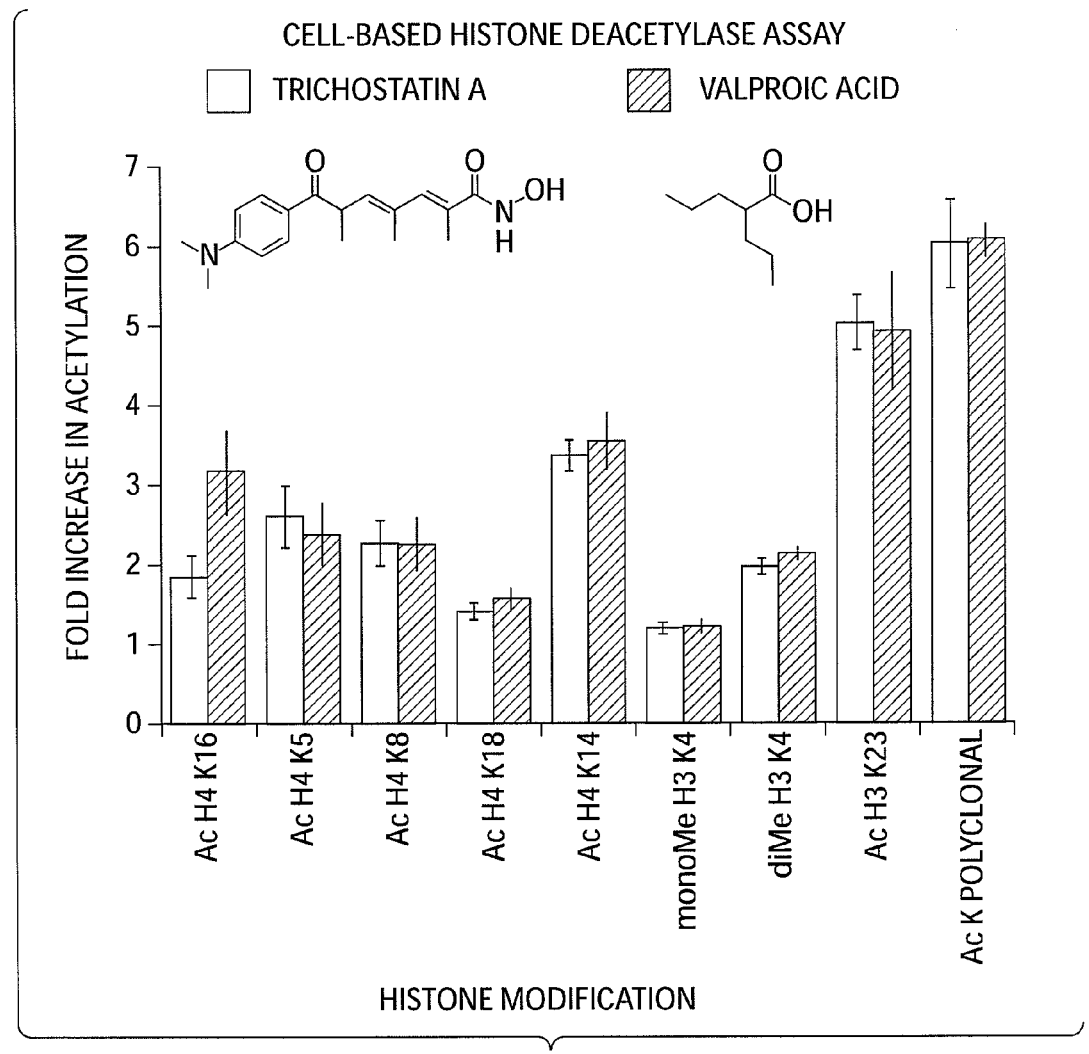
Figure 18G:
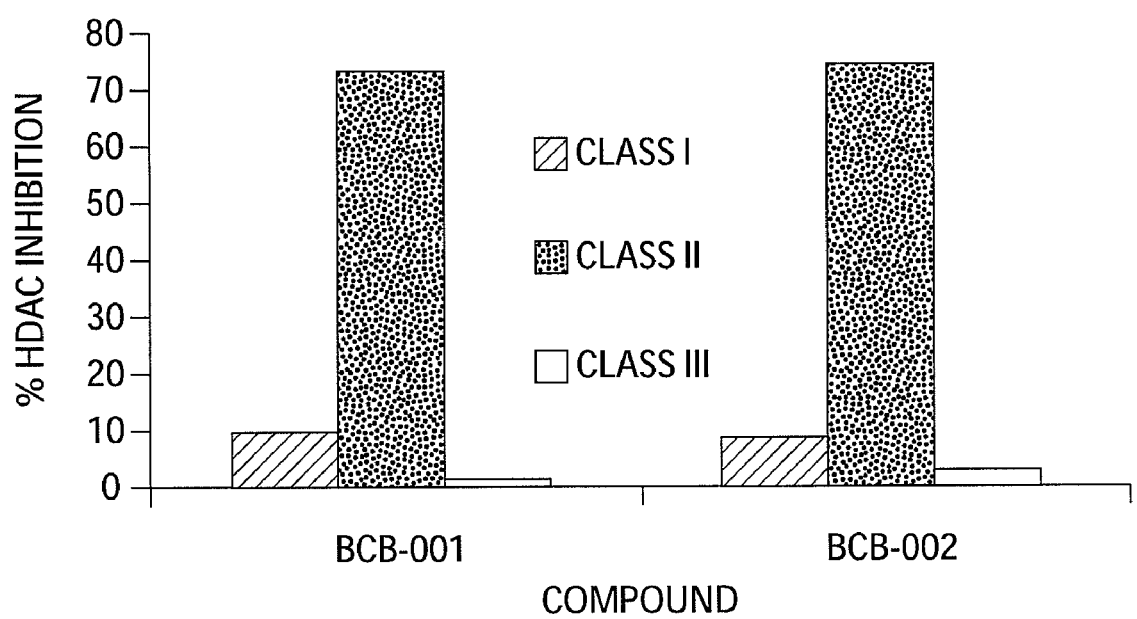

Cell-based and biochemical assays for optimizing HDAC inhibitor potency and selectivity. To assess the effects of compounds on histone acetylation as part of the proposed medicinal chemistry we have implemented an automated microscopy system that enables the rapid and quantitative assessment of chromatin modifications over a wide dynamic range and the simultaneous measurement of the effect of compounds on cell viability, morphology, and proliferation (FIGS. 18a-c). To measure the in vitro biochemical selectivity of novel HDAC inhibitors, we have optimized a 384-well plate based fluorimetric deacetylase for class I and class II HDACs (FIG. 18d) and discovered that apicidin, an ethyl ketone containing, non-hydroxamic acid, is a potent HDAC5 (class 2) inhibitor (FIG. 18e). Recombinant HDAC1-11 preparations will allow testing of the selectivity and potency of inhibitors as part of the medicinal chemistry efforts proposed here. Using additional biochemical assays of a diverse collection of over 1,500 compounds, we discovered two new biasing elements for HDAC inhibition (FIG. 18f) that show selectivity for class II HDACs (FIG. 18g).

Example 18

UW_WT-I_06 Significantly Enhances Associative Learning

The structure of UW_WT-I_06 and UW_WT-I_05 are shown in FIG. 20. Mice were injected 10 days with either 5 mg/kg of MS275 or 25 mg/kg of UW_WT-I_06 or UW_WT-I_05 before training and memory tests as described above. UW_WT-I_06 was discovered to significantly enhance associative learning. These compounds show strong inhibitory activity toward HDAC 1, 2, and 10 with UW_WT-I_06 also inhibiting HDAC 6 and 8. The results are shown in FIG. 21.

1. Andorfer, C. et al. Cell-cycle reentry and cell death in transgenic mice expressing nonmutant human tau isoforms. *J neurosci* 25, 5446-5454 (2005).
2. Santacruz, K. et al. Tau suppression in a neurodegenerative mouse model improves memory function. *Science* 309, 476-481 (2005).
3. Fischer, A., Sananbenesi, F., Pang, P. T., Lu, B. & Tsai, L. H. Opposing roles of transient and prolonged expression of p25 in synaptic plasticity and hippocampus-dependent memory. *Neuron* 48, 825-838 (2005).
4. Cruz, J. C. & Tsai, L. H. Jekyll and Hyde kinase: roles for Cdk5 in brain development and disease. *Curr Opin Neurobiol.* 14, 390-394 (2004).
5. Cruz, J. C., Tseng, H. C., Goldman, J. A., Shih, H. & Tsai, L. H. Aberrant Cdk5 activation by p25 triggers pathological events leading to neurodegeneration and neurofibrillary tangles. *Neuron* 40, 471-83 (2003).
6. Nithianantharajah, J. & Hannan, A. J. Enriched environments, experience-dependent plasticity and disorders of the nervous system. *Nat Rev Neurosci* 7, 697-709 (2006).
7. Kim, J. J. & Fanselow, M. S. Modality-specific retrograde amnesia of fear. *Science* 256, 675-7 (1992).
8. Gilmore, E. C. & Herrup, K. Neocortical cell migration: GABAergic neurons and cells in layers I and VI move in a cyclin-dependent kinase 5-independent manner. *J Neurosci* 21, 9690-700 (2001).
9. Bradshaw, J., Saling, M., Hopwood, M., Anderson, V. & Brodtmann, A. Fluctuating cognition in dementia with Lewy bodies and Alzheimer's disease is qualitatively distinct. *J Neurol Neurosurg Psychiatry* 75, 382-387 (2004).
10. Palop, J. J., Chin, J. & Mucke, L. A network dysfunction perspective on neurodegenerative diseases. *Nature* 443, 768-773 (2006).
11. Frankland, P. W., Bontempi, B., Talton, L. E., Kaczmarek, L. & Silva, A. J. The involvement of the anterior cingulate cortex in remote contextual fear memory. *Science* 304, 881-883 (2004).
12. Need, A. C. & Giese, K. P. Handling and environmental enrichment do not rescue learning and memory impairments in alphaCamKII(T286A) mutant mice. *Genes Brain Behav.* 2, 132-139 (2003).
13. Tang, Y. P., Wang, H. S., Feng, M., Kyin, Y. Z. & Tsien, J. Z. Differential effects of enrichment on learning and memory function in NR2B transgenic mice. *Neuropharmacology*, 779-790 (2001).
14. Rampon, C. et al. Effects of environmental enrichment on gene expression in the brain. *Proc Natl Acad Sci USA* 97, 12880-12884 (2000).
15. Levenson, J. M. et al. Regulation of histone acetylation during memory formation in the hippocampus. *J Biol. Chem.* 279, 40545-40559 (2004).
16. Kumar, A. et al. Chromatin remodeling is a key mechanism underlying cocaine-induced plasticity in striatum. *Neuron* 48, 303-314 (2005).
17. Alarcon, J. M. et al. Chromatin acetylation, memory, and LTP are impaired in CBP+/−mice: a model for the cognitive deficit in Rubinstein-Taybi syndrome and its amelioration. *Neuron* 42, 947-959 (2004).
18. Korzus, E., Rosenfeld, M. G. & Mayford, M. CBP histone acetyltransferase activity is a critical component of memory consolidation. *neuron* 42, 961-972 (2004).
19. Voss, H. U. et al. Possible axonal regrowth in late recovery from the minimally conscious state. *J Clin Invest.* 116, 2005-2011 (2006).
20. van Praag, H., Kempermann, G. & Gage, F. H. Neuronal consequences of environmental enrichment. *Nat Rev Neurosci* 1, 191-198 (2000).
21. Horn, D., Ruppin, E., Usher, M. & Hermann, M. Neural network modeling of Alzheimer's Disease. *Neural Computation* 5, 736-749 (1993).
22. Ruppin, E., Reggia, J. A. & Horn, D. Pathogenesis of schizophrenic delusions and hallucinations: a neural model. *Schizophr Bull* 22, 105-123 (1996).
23. Horn, D., Levy, N. & Ruppin, E. Neuronal-based synaptic compensation: a computational study in Alzheimer's disease. *Neuroal comput* 8, 1227-1243 (1996).
24. Fischer, A., Sananbenesi, F., Schrick, C., Spiess, J. & Radulovic, J. Cyclin-dependent kinase 5 is required for associative learning. *J Neurosci* 22, 3700-7. (2002).
25. Frey R R, Wada C K, Garland R B, Curtin M L, Michaelides M R, Li J, Pease L J, Glaser K B, Marcotte P A, Bouska J J, Murphy S S, Davidsen S K. Trifluoromethyl ketones as inhibitors of histone deacetylase. Bioorg Med Chem Lett 2002; 12:3443-3447.
26. Wada C K, Frey R R, Ji Z, Curtin M L, Garland R B, Holms J H, Li J, Pease L J, Guo J, Glaser K B, Marcotte P A, Richardson P L, Murphy S S, Bouska J J, Tapang P, Magoc T J, Albert D H, Davidsen S K, Michaelides M R. Alpha-keto amides as inhibitors of histone deacetylase. Bioorg Med Chem Lett 2003; 13:3331-3335.
27. Haggarty S J, Wong J C, Koeller K M, Butcher R A, Schreiber S L. Multidimensional chemical genetic analysis of diversity-oriented synthesis-derived deacetylase inhibitors using cell-based assays. Chem Biol 2003a; 10:383-396.

All references, patents and patent publications that are recited in this application are incorporated in their entirety herein by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for recapturing a memory comprising increasing histone acetylation in an amount effective to re-establish access to a memory in a subject having memory loss, wherein increasing histone acetylation is accomplished by administering a therapeutically effective amount of HDAC2 inhibitor to the subject, and wherein the HDAC2 inhibitor comprises a compound selected from the group consisting of:

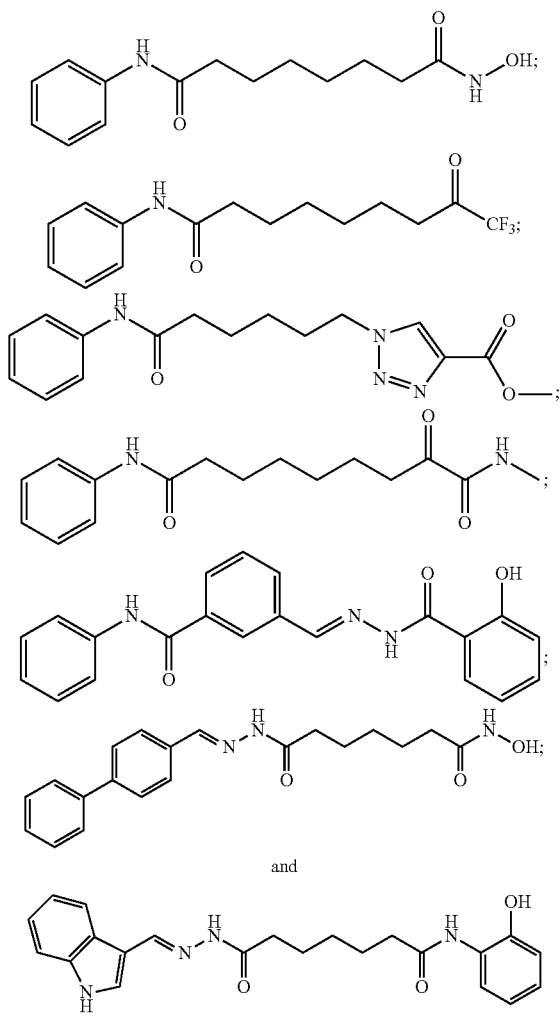

and or pharmaceutically acceptable salts thereof.

2. A method for recapturing a memory comprising increasing histone acetylation in an amount effective to re-establish access to a memory in a subject having memory loss by administering an inhibitor of HDAC2 to said subject, does not inhibit HDAC1, and further comprising altering the methylation level of one or more genes.

3. The method of claim 2, further comprising administering a DNA methylation inhibitor.

4. The method of claim 3, wherein the DNA methylation inhibitor is selected from the group consisting of 5-azacytidine, 5-aza-2'deoxycytidine, 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine, and procainamide, Zebularine, and (−)-egallocatechin-3-gallate.

5. A method for recapturing a memory comprising increasing histone acetylation in an amount effective to re-establish access to a memory in a human subject having chronic memory loss, wherein increasing histone acetylation is accomplished chronically by administering a therapeutically effective amount to recapture a memory of a HDAC inhibitor to the subject, and wherein the HDAC inhibitor is an inhibitor of HDAC2, and wherein the HDAC inhibitor does not inhibit HDAC1.

6. The method of claim 5, wherein a synaptic network in the subject is re-established.

7. The method of claim 6, wherein re-establishing the synaptic network comprises an increase in the number of active brain synapses.

8. The method of claim 5, wherein histone acetylation comprises acetylation of H3 or H4.

9. The method of claim 5, wherein the subject has Alzheimer's disease.

10. The method of claim 5, wherein long-term memory of the subject is impaired.

11. The method of claim 10, wherein the long-term memory impairment is age related.

12. The method of claim 10, wherein the long-term memory impairment is injury related.

13. The method of claim 5, further comprising monitoring the subject to identify recapture of a memory that was previously lost.

14. The method of claim 5 wherein the HDAC inhibitor is an siRNA.

15. A method for recapturing a memory comprising increasing histone acetylation in an amount effective to re-establish access to a memory in a human subject having Alzheimer's disease, wherein increasing histone acetylation is accomplished chronically by administering a therapeutically effective amount to recapture a memory of a HDAC2 inhibitor to the subject, wherein the HDAC2 inhibitor does not inhibit HDAC 3, 5, 7, 9 or 11.

* * * * *